US012377166B2

(12) United States Patent
Zhang et al.

(10) Patent No.: US 12,377,166 B2
(45) Date of Patent: Aug. 5, 2025

(54) IRON OXIDE NANOPARTICLE FOR TARGETED CHEMO-IMMUNOTHERAPY

(71) Applicant: University of Washington, Seattle, WA (US)

(72) Inventors: Miqin Zhang, Seattle, WA (US); Qingxin Mu, Seattle, WA (US); Guanyou Lin, Seattle, WA (US)

(73) Assignee: University of Washington, Seattle, WA (US)

( * ) Notice: Subject to any disclaimer, the term of this patent is extended or adjusted under 35 U.S.C. 154(b) by 137 days.

(21) Appl. No.: 17/821,794

(22) Filed: Aug. 23, 2022

(65) Prior Publication Data
US 2023/0067643 A1 Mar. 2, 2023

Related U.S. Application Data

(60) Provisional application No. 63/237,477, filed on Aug. 26, 2021.

(51) Int. Cl.
| | |
|---|---|
| *A61K 47/69* | (2017.01) |
| *A61K 47/60* | (2017.01) |
| *A61P 35/00* | (2006.01) |
| *A61P 35/04* | (2006.01) |

(52) U.S. Cl.
CPC .......... *A61K 47/6929* (2017.08); *A61K 47/60* (2017.08); *A61K 47/6923* (2017.08); *A61P 35/00* (2018.01); *A61P 35/04* (2018.01)

(58) Field of Classification Search
CPC ................ A61K 47/6929; A61K 47/60; A61K 47/6923; A61P 35/00
See application file for complete search history.

(56) References Cited

U.S. PATENT DOCUMENTS

| | | | |
|---|---|---|---|
| 2002/0001566 A1* | 1/2002 | Rajopadhye ....... | A61K 49/0002 424/1.65 |
| 2018/0296850 A1* | 10/2018 | Wang ................ | A61P 35/00 |
| 2019/0111133 A1* | 4/2019 | Karathanasis ..... | A61K 41/0028 |
| 2020/0179295 A1 | 6/2020 | Kharlampieva | |
| 2021/0038736 A1 | 2/2021 | Berkland | |

FOREIGN PATENT DOCUMENTS

| | | |
|---|---|---|
| CN | 107375952 | 11/2017 |
| CN | 108815523 | 11/2018 |
| CN | 109331190 | 2/2019 |
| CN | 110960695 | 4/2020 |
| CN | 111407746 | 7/2020 |
| CN | 111450081 | 7/2020 |
| WO | 2019016425 | 1/2019 |

OTHER PUBLICATIONS

Chaturvedi, A., and S.K. Pierce, "How location governs Toll like receptor signaling," Traffic 10(6):621-628, 2009.
Villiers, C. L., et al., "Analysis of the toxicity of gold nano particles on the immune system: effect on dendritic cell functions," Journal of Nanoparticle Research 12(1):55-60, 2010.
Lövgren, T., et al., "Enhanced stimulation of human tumor-specific T cells by dendritic cells matured in the presence of Interferon-γ and multiple toll-like receptor agonists," Cancer Immunology, Immunotherapy 66(10):1333-1344, 2017.
Yang, L., et al., "Size dependent biodistribution and toxicokinetics of iron oxide magnetic nanoparticles in mice," Nanoscale 7(2):625-636, 2015.
Blanco, E., et al., "Principles of nanoparticle design for overcoming biological barriers to drug delivery," Nature Biotechnology 33(9):941-951, 2015.
Sturgill, M. G., et al., "Hepatic Enzyme Induction with Phenobarbital and Doxorubicin Metabolism and Myelotoxicity in the Rabbit," Cancer Investigation 18(3):197-205, 2000.
Zhang, Y.-N., et al., "Nanoparticle-liver interactions: Cellular uptake and hepatobiliary elimination," Journal of Controlled Release (2016) 240:332-348.
Carvalho, F. S., et al., "Doxorubicin-Induced Cardiotoxicity: From Bioenergetic Failure and Cell Death to Cardiomyopathy," Medicinal Research Reviews 34(1):106-135, 2014.
Salaun, B., et al., "TLR3 Can Directly Trigger Apoptosis in Human Cancer Cells," The Journal of Immunology 176(8):4894-4901, 2006.
Galon, J., and Bruni, D., "Approaches to treat immune hot, altered and cold tumours with combination immunotherapies," Nature Reviews: Drug Discovery 18(3):197-218, 2019.
Schmid, P., et al., "Atezolizumab and Nab-Paclitaxel in Advanced Triple-Negative Breast Cancer," The New England Journal of Medicine 379(22):2108-2121, 2018.
Kalimutho, M., et al., "Targeted Therapies for Triple-Negative Breast Cancer: Combating a Stubborn Disease," Trends In Pharmacological Sciences 36(12):822-846, 2015.
Mittapalli, R. K., et al., "Paclitaxel-Hyaluronic Nano-Conjugates Prolong Overall Survival in a Preclinical Brain Metastases of Breast Cancer Model," Molecular Cancer Therapeutics 12(11):2389-2399, 2013.
Wang, S., et al., "Hyaluronic acid-coated PEI-PLGA nanoparticles mediated co-delivery of doxorubicin and miR-542-3p for triple negative breast cancer therapy," Nanomedicine: Nanotechnology, Biology, and Medicine 12(2):411-420, 2016.

(Continued)

*Primary Examiner* — Robert A Wax
*Assistant Examiner* — William Craigo
(74) *Attorney, Agent, or Firm* — CHRISTENSEN O'CONNOR JOHNSON KINDNESS PLLC

(57) ABSTRACT

Multifunctional nanoparticle for targeted therapeutic drug delivery, comprising (a) an iron oxide core having silica-polyethylene glycol coupled thereto to provide an iron oxide coated core, (b) a cytotoxic agent reversibly associated with the coated core; (c) an immunomodulating agent reversibly associate with the coated core; and (d) a tumor targeting agent associated with the coated core. Methods for using the nanoparticle to treat cancers and methods for making the nanoparticle.

20 Claims, 39 Drawing Sheets
Specification includes a Sequence Listing.

(56) References Cited

OTHER PUBLICATIONS

Deng, X., et al., "Hyaluronic acid-chitosan nanoparticles for co-delivery of MiR-34a and doxorubicin in therapy against triple negative breast cancer," Biomaterials 35(14):4333-4344, 2014.

Misra, A. C., et al., "CXCR4-Targeted Nanocarriers for Triple Negative Breast Cancers," Biomacromolecules 16(8):2412-2417, 2015.

Sussman, D., et al., "SGN-LIV1A: A Novel Antibody-Drug Conjugate Targeting LIV-1 for the Treatment of Metastatic Breast Cancer," Molecular Cancer Therapeutics 13(12):2991-3000, 2014.

Hansel, T. T., et al., "The safety and side effects of monoclonal antibodies," Nature Reviews Drug Discovery 9(4):325-338, 2010.

Kennel, S. J., et al., "CD44 expression on murine tissues," Journal of Cell Science 104(2):373-382, 1993.

Bodey, B., et al., "Over-Expression of Endoglin (CDI05): A Marker of Breast Carcinoma-Induced Neo-Vascularizationn," Anticancer Research 18(5A):3621-3628, 1998.

Dales, J. P., et al., "CD105 Expression Is a Marker of High Metastatic Risk and Poor Outcome in Breast Carcinomas," American Journal of Clinical Pathology 119(3):374-380, 2003.

Shao, K., et al., "Nanoparticle-Based Immunotherapy for Cancer," ACS Nano 9(1):16-30, 2015.

Bauleth-Ramos, T., et al., "Nutlin-3a and Cytokine Co-loaded Spermine-Modified Acetalated Dextran Nanoparticles for Cancer Chemo-Immunotherapy," Advanced Functional Materials 27(42), 1703303, 2017, 14 pages.

Liu, Y., et al., "Dual pH-responsive multifunctional nanoparticles for targeted treatment of breast cancer by combining immunotherapy and chemotherapy," Acta Biomaterialia 66:310-324, 2018.

Wang, T., et al., "Selective targeting of tumor cells and tumor associated macrophages separately by twin-like core-shell nanoparticles for enhanced tumor-localized chemoimmunotherapy," Nanoscale 11(29):13934-13946, 2019.

Zhang, P., et al., "Polyelectrolyte Multilayers Assembled Entirely from Immune Signals on Gold Nanoparticle Templates Promote Antigen-Specific T Cell Response," ACS Nano 9(6):6465-6477, 2015.

Trad, M., et al., "T Lymphocyte Inhibition by Tumor-Infiltrating Dendritic Cells Involves Ectonucleotidase CD39 but Not Arginase-1," BioMed Research International vol. 2015, 891236, 10 pages.

Dehshahri, A., et al., "Enhanced Delivery of Plasmid Encoding Interleukin-12 Gene by Diethylene Triamine Penta-Acetic Acid (DTPA)-Conjugated PEI Nanoparticles," Applied Biochemistry and Biotechnology 179(2):251-269, 2016.

Sheikhsaran, F., et al., "Tetraiodothyroacetic acid-conjugated polyethylenimine for integrinreceptor mediated delivery of the plasmid encoding IL-12 gene," Colloids and Surfaces B: Biointerfaces 150:426-436, 2017.

Tao, K., et al., "Imagable 4T1 model for the study of late stage breast cancer," BMC Cancer (2008) 8(1):228, 19 pages.

Bao, L., et al., "Increased Expression of P-Glycoprotein Is Associated with Doxorubicin Chemoresistance in the Metastatic 4T1 Breast Cancer Model," The American Journal of Pathology 178(2): 838-852, 2011.

Mu, Q., et al., "Gemcitabine and chlorotoxin conjugated iron oxide nanoparticles for glioblastoma therapy," Journal of Materials Chemistry B 4(1):32-36, 2016.

Riemer, J., et al., "Colorimetric ferrozine-based assay for the quantitation of iron in cultured cells," Analytical Biochemistry 331(2):370-375, 2004.

Madaan, A., et al., "A stepwise procedure for isolation of murine bone marrow and generation of dendritic cells," Journal of Biological Methods 1(1):1-6, 2014.

Lu, J., et al., "Breast Cancer Metastasis: Challenges and Opportunities," Cancer Research 69(12):4951-4953, 2009.

Yao, H., et al., "Triple-negative breast cancer: is there a treatment on the horizon?," Oncotarget 8(1):1913-1924, 2017.

Uno, T., et al., "Eradication of established tumors in mice by a combination antibody-based therapy," Nature Medicine 12(6):693-698, 2006.

Oner, G., et al., "Triple-negative breast cancer—Role of immunology: A systemic review," The Breast Journal 26(5):995-999, 2020.

Irby, D., et al., "Lipid-Drug Conjugate for Enhancing Drug Delivery," Molecular Pharmaceutics 14(5):1325-1338, 2017.

Zhao, M., et al., "Abraxane, the Nanoparticle Formulation of Paclitaxel Can Induce Drug Resistance by Up-Regulation of P-gp," PloS One 10(7), e0131429, 2015, 19 pages.

Kuai, R., et al., "Designer vaccine nanodiscs for personalized cancer immunotherapy," Nature Materieals 16(4):489-498, 2017.

Fan, Y., et al., "Immunogenic Cell Death Amplified by Co-localized Adjuvant Delivery for Cancer Immunotherapy," Nano Letters 17(12):7387-7393, 2017.

Shi, S. X., et al., "Tumor Vasculature Targeting and Imaging in Living Mice with Reduced Graphene Oxide," Biomaterials 34(12):3002-3009, 2013.

Tewey, K., et al., "Adriamycin-Induced DNA Damage Mediated by Mammalian DNA Topoisomerase II," Science 226(4673):466-468, 1984.

Okada, H., et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma," Journal of Clinical Oncology 29(3):330-336.

Fang, C., et al., "Functionalized Nanoparticles with Long-Term Stability in Biological Media," Small 5(14):1637-1641, 2009.

Matsumoto, et al., "Subcellular Localization of Toll-Like Receptor 3 in Human Dendritic Cells," The Journal of Immunology 171(6), 3154-3162, 2003.

Lane, P., et al., "Temperature Dependence Studies of Adriamycin Uptake and Cytotoxicity," Cancer Research 47(15):4038-4042, 1987.

Tanaka, H., et al., "Classification of Chemotherapeutic Agents Based on Their Differential In vitro Effects on Dendritic Cells," Cancer Research 69(17):6978-6986, 2009.

Salem, M. L., et al., "The TLR3 agonist poly(I:C) targets CD8+ T cells and augments their antigen-specific responses upon their adoptive transfer into naïve recipient mice," Vaccine 27(4):549-557, 2009.

Siegel, R. L., et al., "Cancer Statistics, 2020," CA: A Cancer Journal for Clinicians 70(1):7-30, 2020.

Jones, S. E., "Metastatic Breast Cancer: The Treatment Challenge," Clinical Breast Cancer 8(3):224-233, 2008.

Foulkes, W. D., et al., "Triple-Negative Breast Cancer," New England Journal of Medicine 363(20):1938-1948, 2010.

Bandyopadhyay, A., et al., "Doxorubicin in Combination with a Small TGFβ Inhibitor. A Potential Novel Therapy for Metastatic Breast Cancer in Mouse Models," PLoS One 5(4):e10365, 2010.

Filatenkov, A., et al., "Treatment of 4T1 Metastatic Breast Cancer with Combined Hypofractionated Irradiation and Autologous T-Cell Infusion," Radiation Research 182(2):163-169, 2014.

Lopez, J. S., and U. Banerji, "Combine and conquer: challenges for targeted therapy combinations in early phase trials," Nature Reviews. Clinical oncology 14(1):57-66, 2017.

Liang, J., et al., "Nanoparticle-enhanced chemo-immunotherapy to trigger robust antitumor immunity," Science Advances (2020) 6 (35), eabc3646, 15 pages.

Mu, Q., et al., "Nanoparticles for imaging and treatment of metastatic breast cancer," Expert Opinion on Drug Delivery 14(1):123-136, 2017.

Mitchell, M. J., et al., "Engineering and physical sciences in oncology: challenges and opportunities," Nature Reviews: Cancer 17(11):659-675, 2017.

Wilhelm, S., et al., "Analysis of nanoparticle delivery to tumours," Nature Reviews: Materials 1(5):1-12, 2016.

Larrañeta, E., et al., "Hydrogels for Hydrophobic Drug Delivery. Classification, Synthesis and Applications," Journal of Functional Biomaterials 9(13):1-20, 2018.

Mo, Z. C., et al., "A high-density lipoprotein-mediated drug delivery system," Advanced Drug Delivery Reviews 106:132-147, 2016.

Xue, P., et al., "Hydrophobic drug self-delivery systems as a versatile nanoplatform for cancer therapy: A review," Colloids Surfaces B: Biointerfaces 180,:202-211, 2019.

(56) References Cited

OTHER PUBLICATIONS

Yang, G., et al., "Bioinspired Core-Shell Nanoparticles for Hydrophobic Drug Delivery," Angewandte Chemie International Edition 58(40):14357-14364, 2019.
Gradishar, W. J., "Albumin-bound paclitaxel: a next-generation taxane," Expert Opinion on Pharmacotherapy 7(8):1041-1053, 2006.
Villano, J. L., et al., "Abraxaner® induced life-threatening toxicities with metastatic breast cancer and hepatic insufficiency," Invest New Drugs 24(5):455-456, 2006.
Lee, H., et al., "Efficacy and safety of nanoparticlealbumin-bound paclitaxel compared with solvent-based taxanes for metastatic breast cancer: A meta-analysis," Scientific Reports 10, 530, 2020, 9 pages.
Yoon, H.Y., et al., "Engineering nanoparticle strategies for effective cancer immunotherapy," Biomaterials 178:597-607, 2018.
Oberli, M. A., et al., "Lipid Nanoparticle Assisted mRNA Delivery for Potent Cancer Immunotherapy," Nano Letters 17(3):, 1326-1335, 2017.
Wang, D., et al., "Acid-Activatable Versatile Micelleplexes for PD-L1 Blockade-Enhanced Cancer Photodynamic Immunotherapy," Nano Letters 16(9):5503-5513, 2016.
Li, S.-Y., et al., "Restoring anti-tumor functions of T cells via nanoparticle-mediated immune checkpoint modulation," Journal of Controlled Release 231:17-28, 2016.
Stephan, M. T., et al., "Therapeutic cell engineering with surface-conjugated synthetic nanoparticles," Nature Medicine 16(9), 1035-1042, 2010.
Yuan, H., et al., "Multivalent bi-specific nanobioconjugate engager for targeted cancer immunotherapy," Nature Nanotechnology 12(8), 763-771. 2017.
Yazdi, M. H., et al., "The Preventive Oral Supplementation of a Selenium Nanoparticle-enriched Probiotic Increases the Immune Response and Lifespan of 4T1 Breast Cancer Bearing Mice," Arzneimittelforschung 62(11):525-531, 2012.
Lizotte, P. H., et al., "In situ vaccination with cowpea mosaic virus nanoparticles suppresses metastatic cancer," Nature Nanotechnology 11(3):295-303, 2016.
De Koker, S., et al., "Engineering Polymer Hydrogel Nanoparticles for Lymph Node-Targeted Delivery," Angewandte Chemie International Edition 55(4):1334-1339, 2016.
Schmid, D., et al., "T cell-targeting nanoparticles focus delivery of immunotherapy to improve antitumor immunity," Nature Commun ication (2017) 8, 1747, 2017, 12 pages.
Lin, G., et al., "Inorganic Nanomaterial-Mediated Gene Therapy in Combination with Other Antitumor Treatment Modalities," Advanced Functional Materials, 31, 2007096, 2021, 34 pages.
Bi, X., et al., "Endoglin," Journal of Chongqing Medical University 32(3)232-235, 2007.
Chen, F., et al., "In Vivo Tumor Targeting and Image-Guided Drug Delivery with Antibody-Conjugated, Radiolabeled Mesoporous Silica Nanoparticles," ACS Nano 7(10):9027-9039, 2013.
Hong, H., et al., "Positron emission tomography imaging of CD105 expression during tumor angiogenesis," European Journal of Nuclear Medicine and Molecular Imaging 38(7):1335-1343, 2011.
Tsujie, M., et al., "Effective anti-angiogenic therapy of established tumors in mice by naked anti-human endoglin (CD105) antibody: Differences in growth rate and therapeutic response between tumors growing at different sites," International Journal of Oncology 29(5):1087-1094, 2006.
Uneda, S., et al., "Anti-endoglin monoclonal antibodies are effective for suppressing metastasis and the primary tumors by targeting tumor vasculature," International Journal of Cancer 125(6):1446-1453, 2009.
Dennis, J. W., "Effects of Swainsonine and Polyinosinic:Polycytidylic Acid on Murine Tumor Cell Growth and Metastasis," Cancer Research 46(10):5131-5136, 1986.
Schmidt, K. N., et al., "APC-Independent Activation of NK Cells by the Toll-Like Receptor 3 Agonist Double-Stranded RNA," The Journal of Immunology 172(1):138-143, 2004.
Wesch, D., et al., "Direct Costimulatory Effect of TLR3 Ligand Poly(I:C) on Human γδ T Lymphocytes," The Journal of Immunology 176(3):1348-1354, 2006.
Hirabayashi, K., et al., "Inhibition of Cancer Cell Growth by Polyinosinic-Polycytidylic Acid/Cationic Liposome Complex: A New Biological Activity," Cancer Research 59(17):4325-4333, 1999.
Ramasamy, T., et al., "Layer-by-layer assembly of liposomal nanoparticles with PEGylated polyelectrolytes enhances systemic delivery of multiple anticancer drugs," Acta Biomaterialia 10(12):5116-5127, 2014.
Correa, S., et al., "Engineering nanolayered particles for modular drug delivery," Journal of Controlled Release 240:364-386, 2016.
Zhang, Y., et al., "Co-delivery of doxorubicin and curcumin by pH-sensitive prodrug nanoparticle for combination therapy of cancer," Scientific Reports 6, 21225, 12 pages, 2016.
Hernández-Gil, J., et al., "An Iron Oxide Nanocarrier Loaded with a Pt(IV) Prodrug and Immunostimulatory dsRNA for Combining Complementary Cancer Killing Effects," Advanced Healthcare Materials 4(7):1034-1042, 2015.
Cheng, Y. S., and Xu, F., "Anticancer function of polyinosinic-polycytidylic acid," Cancer Biology & Therapy 10(12):1219-1223, 2010.
Medzhitov, R., "Toll-Like Receptors and Innate Immunity," Nature Reviews: Immunology 1(2):135-145, 2001.
Tugues, S., et al., "New insights into IL-12-mediated tumor suppression," Cell Death and Differentiation 22(2):237-246, 2015.
Fernandez, N. C., et al., "Dendritic cells directly trigger NK cell functions: Cross-talk relevant in innate anti-tumor immune responses in vivo," Nature Medicine 5(4):405-411, 1999.
Lin, G., et al., "A highly selective iron oxide-based imaging nanoparticle for long-term monitoring of drug-induced tumor cell apoptosis," Biomaterials Science 9(2):471,-481 2021.
Jeon, H., et al., "Methionine deprivation suppresses triple-negative breast cancer metastasis in vitro and in vivo," Oncotarget 7(41):67223-67234, 2016.
Knockenhauer, K. E., and T.U. Schwartz, "The Nuclear Pore Complex as a Flexible and DynamicGate," Cell 164(6):1162-1171, 2016.
Cobaleda-Siles, M., et al., "An Iron Oxide Nanocarrier for dsRNA to Target Lymph Nodes and Strongly Activate Cells of the Immune System," Small 10(24):5054-5067, 2014.
Momparler, R. L., et al., "Effect of Adriamycin on DNA, RNA, and Protein Synthesis in Cell-free Systems and IntactCells," Cancer Research 36(8):2891-2895, 1976.
Zhang, Y., et al., "Establishment of a murine breast tumor model by subcutaneous or orthotopic implantation," Oncology Letters 15(5):6233-6240, 2018.
Li, C.-W., et al., "Eradication of Triple-Negative Breast Cancer Cells by Targeting Glycosylated PD-L1," Cancer Cell 33(2):187-201, 2018.
Ruan, S. B., et al., "Targeting delivery and deep penetration using multistage nanoparticles for triple-negative breast cancer," RSC Advances 5(79):64303-64317, 2015.
Park, J., et al., "Ultra-large-scale syntheses of monodisperse nanocrystals," Nature Materials 3(12): 891-895, 2004.
Mu, Q., et al., "Iron oxide nanoparticle targeted chemoimmunotherapy for triple negative breast cancer," Materials Today 50:149-169, 2021.
Zhu, G., et al., "Albumin/vaccine nanocomplexes that assemble in vivo for combination cancer immunotherapy," Nature Communications 8(1), 1954, 2017, 15 pages.
Acharya, S., et al., "Targeted epidermal growth factor receptor nanoparticle bioconjugates for breast cancer therapy," Biomaterials 30:5737-5750, 2009.
Alexis, F., et al., "Nanoparticle Technologies for Cancer Therapy," Handbook of Experimental Pharmacology 197:55-86, 2010.
Ashrafizadeh, M., et al., "Nanoparticles Targeting STATs in Cancer Therapy," Cells 8, 1158, 2019, 27 pages.
Brannon-Peppas, L., and J.O. Blanchette, "Nanoparticle and targeted systems for cancer therapy," Advanced Drug Delivery Reviews 56:1649-1659, 2004.

(56) References Cited

OTHER PUBLICATIONS

Gurunathan, S., et al., "Nanoparticle-Mediated Combination Therapy: Two-in-One Approach for Cancer," International Journal of Molecular Sciences 19, 3264, 2018, 37 pages.

Hu, C., et al., "Coadministration of iRGD with Multistage Responsive Nanoparticles Enhanced Tumor Targeting and Penetration Abilities for Breast Cancer Therapym," ACS Applied Materials & Interfaces, 10:22571-22579, 2018.

Liz-Marzan, L.M., et al., "Synthesis of Nanosized Gold-Silica Core-Shell Particles," Langmuir 12:4329-4335, 1996.

Medina, M.A., et al., "Triple-Negative Breast Cancer: A Review of Conventional and Advanced Therapeutic Strategies," International Journal of Environmental Research and Public Health 17, 2078, 2020, 32 pages.

Mustafa, S., et al., "Surface properties of the mixed oxides of iron and silica," Colloids and Surfaces A: Physicochemical and Engineering Aspects 205:273-282, 2002.

Pawar, A., and P. Prabhu, "Nanosoldiers: A promising strategy to combat triple negative breast cancer," Biomedicine & Pharmacotherapy 110:319-341, 2019.

Schärtl, W., "Current directions in core-shell nanoparticle design," Nanoscale 2:829-843, 2010.

Singh, D.D., and D.K. Yadav, "TNBC: Potential Targeting of Multiple Receptors for a Therapeutic Breakthrough, Nanomedicine, and Immunotherapy," Biomedicines 9, 876, 2021, 26 pages.

Thakur, V., and R.V. Kutty, "Recent advances in nanotheranostics for triple negative breast cancer treatment," Journal of Experimental & Clinical Cancer Research 38:430 2019, 22 pages.

Tietze, R., et al., "Magnetic nanoparticle-baseddrugdeliveryforcancertherapy," Biochemical and Biophysical Research Communications 468:463-470, 2015.

Wang, R., et al., "Surface-Functionalized Modified Copper Sulfide Nanoparticles Enhance Checkpoint Blockade Tumor Immunotherapy by Photothermal Therapy and Antigen Capturing," ACS Applied Materials & Interfaces 11:13964-13972, 2019.

Wei, J. et al., "Multifunctional polymeric micelle-based chemo-immunotherapy with immune checkpoint blockade for efficient treatment of orthotopic and metastatic breast cancer," Acta Pharmaceutica Sinica B 9(4):819-831, 2019.

Zheng, D.-W., et al., "Highly Integrated Nano-Platform for Breaking the Barrier between Chemotherapy and Immunotherapy," Nano Letters 16:4341-4347, 2016.

* cited by examiner

IRON OXIDE NANOPARTICLE FOR TARGETED CHEMO-IMMUNOTHERAPY

CROSS-REFERENCE TO RELATED APPLICATION

This application claims the benefit of U.S. Patent Application No. 63/237,477, filed Aug. 26, 2021, expressly incorporated herein by reference in its entirety.

STATEMENT OF GOVERNMENT LICENSE RIGHTS

This invention was made with government support under R01EB026890 awarded by the National Institutes of Health. The government has certain rights in the invention.

STATEMENT REGARDING SEQUENCE LISTING

The sequence listing associated with this application is provided in XML format and is hereby incorporated by reference into the specification. The name of the XML file containing the sequence listing is 3915-P1220USUW_Seq_List_20220818.xml. The XML file is 1.87 KB; was created on Aug. 18, 2022, and is being submitted via Patent Center with the filing of the specification.

BACKGROUND

Breast cancer is the second leading cause of cancer-related deaths among women in the U.S. An estimated 1 in 8 women will develop breast cancer in their lifetime. Treating stage IV or metastatic breast cancer is a formidable challenge because of its developed resistance to therapeutics and aggressive proliferation; it can quickly metastasize and spread into multiple organs. Despite the advances in developing multi-agent treatment approaches, the survival rate for metastatic breast cancer remains low (<25%). The treatment for triple negative breast cancer (TNBC) poses additional challenges as they lack epidermal growth factor receptor 2 (HER-2), estrogen receptors (ER), or progesterone receptors (PR), and thus do not respond to hormonal therapy available in the clinic.

The current treatment options for TNBC commonly starts with surgery to remove the bulk of the tumor mass followed by adjuvant therapy with combinatory therapy such as multi-agent chemotherapy, multi-immune agent therapy, radio-immunotherapy, and chemo-immuno-therapy. Recently, the combination of multiple treatments has emerged as a promising approach aimed to circumvent drug resistance and improve outcomes. Among these combinatorial therapies, combined chemo- and immunotherapy has received much attention because of the remarkable progress made in clinical cancer immunotherapy and large accumulation of knowledge in the clinical practice of chemotherapy. However, two major obstacles impede the clinical translation of this combined therapy. First, the two therapeutic agents do not work synchronously or take effect on a cancer cell at the same time even if they are administered together due to the difference in pharmacokinetic profile. Second, there is a safety concern of the severe systemic immune responses incurred as a result of off-target cytotoxicity. Nanotechnology has recently shown promise to seamlessly integrate chemo- and immuno-therapeutic agents in a single nanoparticle (NP) formulation which allows the multiple agents to reach target cells simultaneously and act synchronously. Incorporation of a targeting ligand into such a NP formulation may further improve its safety and therapeutic efficacy by reducing systemic toxicity and required effective dosage of therapeutics. Surface modification can also be employed to optimize the pharmacokinetic profile. Thus, a nanotechnology-based approach may substantially improve the efficacy of cancer therapeutics.

Although conceptually viable, the implement of this nanomedicine-based approach has proven to be non-trivial, primarily because of the difficulty in delivering efficacious amounts of therapeutic agents to tumor cells and making drug-loaded NPs sufficiently small. Large-size NPs (>100 nm) can be quickly eliminated by the reticuloendothelial system (RES) before they can reach target sites and yet large-size NPs are less effective in drug delivery than smaller NPs. Anticancer drugs used in the clinic for treating breast cancer such as paclitaxel (PTX) and doxorubicin (Dox) are hydrophobic, and it is a challenge to make NPs sufficiently small when the NPs are loaded with hydrophobic drugs that are incompatible with aqueous biological solutions. In the past decade, a number of NP formulations have been developed to deliver hydrophobic chemotherapeutics (e.g., PTX or Dox). Only Abraxane, a formulation of PTX-loaded NPs, with a size of 130 nm, was approved for the clinic. Yet, the use of Abraxane is limited to patients with advanced breast cancer because of its severe systemic toxicity (e.g., hepatic insufficiency, high grade neuropathy and neutropenia) which is attributable to its large size and non-specificity to targets, uncontrollable dissociation of the non-covalently bound PTX so that a higher drug dosage is needed to achieve sufficient potency. On the other hand, nanomedicine-based immunotherapy can effectively harness the immune system against tumors mostly by targeted delivery of antigen/adjuvant and immune checkpoint modulators or direct cell surface modifications. Lipidic, polymeric and protein-based nanoparticles have served as promising carriers for delivering strong immunostimulants such as CpG and ovalbumin as well as immune checkpoint inhibitors targeting PDL1/PD1 and CTLA-4. Moreover, liposomes and polystyrene NPs have been conjugated onto the surfaces of T cells, hematopoietic stem cells and antigen-presenting cells to treat antigen-expressing tumor cells. Some NPs have immune-stimulating properties inherently and can activate host immune systems against cancer. Nevertheless, the majority of these organic NPs have a size typically in the range of 150-300 nm. Clearly, it would be even more difficult to make small NPs (<100 nm) that carry both chemo- and immune-therapeutic agents for TNBC. Further, most polymer-based NPs suffer from unpredictable size variation when loaded with therapeutic cargos or when placed in a physiological environment, which results in an inconsistent pharmaceutical profile and therapeutic results.

Despite the advances in the developments of suitable nanoparticle therapeutics and in view of their shortcomings, a need exists for improved nanoparticle therapeutic and methods for their use in treating cancers. The present disclosure seeks to fulfill this need and provides further related advantages.

SUMMARY

In one aspect, the disclosure provides a multifunctional nanoparticle for targeted therapeutic drug delivery. In certain embodiments, the nanoparticle comprises:

(a) an iron oxide core having silica-polyethylene glycol coupled thereto to provide an iron oxide coated core;

(b) a cytotoxic agent reversibly associated with the coated core;
(c) an immunomodulating agent reversibly associated with the coated core; and
(d) a tumor targeting agent associated with the coated core.

In another aspect, the present disclosure provides pharmaceutical compositions that include the nanoparticles of the invention in combination with a pharmaceutically acceptable carrier (e.g., dextrose or saline solution for injection).

In further aspects, the present disclosure provides methods for treating breast cancer in a subject, methods for inhibiting breast cancer tumor growth in a subject, and methods for inhibiting breast cancer metastasis in a subject. In the methods, an effective amount of the nanoparticle is administered to the subject in need thereof.

In another aspect of the disclosure, methods for making a multifunctional nanoparticle are provided. In certain embodiments, the method comprises:
(a) forming a layer of silica-polyethylene glycol surrounding an iron oxide core to provide a coated iron oxide core;
(b) associating a tumor targeting agent to the coated core;
(c) forming a first layer of a cytotoxic agent surrounding the coated core; and
(d) forming a second layer of an immunomodulating agent surrounding the first layer to provide a nanoparticle comprising a tumor targeting agent, a cytotoxic agent, and an immunomodulating agent.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 2A shows zeta-potential of IONP-DOX-EBP as a function of Fe/DOX ratio. FIG. 2B shows zeta-potential of IONP-DOX-Poly IC-EBP as a function of Fe/Poly IC ratio (Fe/DOX ratio was 10:11) (HEPES, pH 7.4). FIG. 2C shows hydrodynamic size of IONP-DOX-Poly IC-EBP as a function of Fe/Poly IC ratio (Fe/DOX ratio was 10:11). FIG. 2D shows TEM and FIG. 2E shows AFM micrographs of IONP-DOX-Poly IC-EBP (Fe/DOX/Poly IC ratio was 10:11:16). Scale bars represent 50 nm. FIG. 2F shows histogram of diameters of IONP-DOX-Poly IC-EBP evaluated from AFM images. FIG. 2G shows UV-Vis spectra of DOX, EBP, Poly IC, IONP, IONP-DOX-EBP and IONP-DOX-Poly IC-EBP in PBS buffer (pH 7.4). Arrows indicate the peaks for Poly IC (left) and DOX (right). FIG. 2H shows agarose gel electrophoresis analysis of unbound Poly IC from IONP-DOX-EBP/Poly IC mixtures. Lower panel displays the relative intensities of the gel bands of the upper panel, evaluated with by ImageJ. FIG. 2I compares cumulative release of DOX from IONP-DOX-Poly IC-EBP under different pH conditions at 37° C.

FIG. 3A shows CLSM images of cells with membrane and nuclei stained green and blue, respectively. The excitation state fluorescence of DOX (red) was imaged (Ex: 495 nm; Em: 580-654 nm). Scale bar: 100 μm. FIG. 3B shows flow cytometry analysis of DOX uptake into 4T1 cells treated with various agents, performed 2 h after incubation (Ex: 488 nm; Em: 585 nm with 42 nm bandwidth). FIG. 3C shows mean fluorescence intensity (MFI) of DOX from flow cytometry analysis. *$P<0.005$, $P<0.0001$ by one-way ANOVA with Turkey's post-hoc test. FIG. 3D shows normalized MFI of DOX at 37° C. and 4° C. quantified by flow cytometry. $P<0\ 0.001$, ****$P<0.0001$, Student's unpaired t-test. FIG. 3E shows viability of 4T1 cells incubated with various agents ([Fe]≈0.9×[DOX]), assessed by Alarma Blue assay. FIG. 3F compares flow cytometry analysis of cell apoptosis induced by i: medium control; ii: IONPs; iii: DOX; iv: IONP-DOX-Poly IC-EBP. DOX concentration was 1 μg/mL equivalent ([Fe]≈0.9 μg/mL) and incubation time was 48 h.

FIG. 4A shows confocal fluorescence microscopy imaging of cellular uptake of free DOX, IONP-DOX-EBP and IONP-DOX-Poly IC-EBP into BMDCs. Cell nuclei were stained with DAPI. DOX was imaged at Ex: 495 nm and Em: 580-654 nm. NPs were labeled with Cy5 (red) and imaged at Ex: 652 nm and Em: 665-745 nm. FIGS. 4B and 4C show flow cytometry study of DC maturation. BMDCs were incubated with Poly IC, IONP-DOX-EBP or IONP-DOX-Poly IC-EBP for 24 h and the expression of CD86 (4B) and CD80 (4C) were evaluated. FIGS. 4D and 4E show mean fluorescence intensities of anti-CD86 and anti-CD80 antibodies, respectively, derived from 4B and 4C. FIG. 4F shows production of IL-12 by BMDCs in cellular supernatants 24 h after incubation with Poly IC, IONP-DOX-EBP or IONP-DOX-Poly IC-EBP, quantified by ELISA. FIG. 4G shows toxicity of Poly IC, IONP-DOX-EBP and IONP-DOX-Poly IC-EBP on BMDCs after 24 h incubation, assessed by the Alamar Blue viability assay. $P<0.01$, *$P<0.005$, ****$P<0.0001$ by one-way ANOVA with Turkey's post-hoc test.

FIG. 5A is a schematic illustration of activation of immune response by IONP-DOX-Poly IC-EBP. FIG. 5B compares production of IL-12 in mouse serum by intravenous (I.V.) injection of DOX (5 mg/kg), Poly IC (18 mg/kg), or IONP-DOX-Poly IC-EBP (DOX 10 mg/kg, Poly IC 18 mg/kg), assessed by ELISA. Serum was collected before injection and 1.5, 6.5, and 24 h post-injection. *$P<0.05$, $P<0.01$, **$P<0.0001$ by two-way ANOVA with Turkey's post-hoc test. FIG. 5C shows flow cytometry analysis of single cell suspensions processed from tumor and spleen of mice treated with IONP-DOX, Poly IC, or IONP-DOX-Poly IC-EBP (DOX 10 mg/kg and Poly IC 18 mg/kg equivalent). Mice were euthanized three days after treatments. Single cell suspensions of tumors and spleens were stained with anti-CD8, CD25, CD69 antibodies for analysis.

FIG. 6A shows in vivo MRI of two cross sections (upper and lower panels, respectively) of abdomen of the same mouse before, and 1 and 24 h after administration of IONP-DOX-Poly IC-EBP. Red arrows and dashed circles indicate tumor, yellow and green dashed circles indicate kidney or spleen, respectively. FIG. 6B shows relative MR intensity in tumor, kidney and spleen in mice, acquired pre-injection, 1 h and 1 d post-injection. FIG. 6C shows live IVIS images of mice bearing 4T1-luc tumors and treated with IONP-DOX-Poly IC-EBP-Cy5.5. The images were acquired before I.V. administration and 1 h to 6 days post-administration.

FIG. 7A compares biodistribution of NPs (labeled with Cy5.5) quantified by measuring Cy5.5 fluorescence intensity in various organs. $P<0.01$, **$P<0.0001$ by two-way ANOVA with Turkey's post-hoc test. FIG. 7B compares pharmacokinetics of IONP-DOX-Poly IC-EBP assessed by quantifying DOX fluorescence intensities. DOX: Ex, 500 nm; Em, 600 nm. Fluorescence intensity of DOX at 1 h was normalized to 1.

FIG. 8A shows confocal fluorescence microscopy images of tissues sections of various organs/tumors. Red: cell membrane (WGA-AF647). Blue: cell nucleus (DAPI). Green: DOX (Ex: 495 nm; Em: 600-650 nm). Scale bar: 75 µm. FIG. 8B shows H&E-stained tissue sections of heart, liver, spleen, lung, kidney and tumor from mice treated with the same conditions in 8A.

FIG. 9A shows a schedule of tumor inoculation, treatment regimen, and monitoring. FIG. 9B shows tumor size as a function of time over the 28-day period shown in a., starting from tumor inoculation (day 0), for mice treated with eight agents (n=4/per agent). $P<0.01$, *$P<0.005$ by two-way ANOVA with Turkey's post-hoc test. Each mouse was administered three times by I.V. injection and the tumor volume was measured every three days, both following the schedule shown in 9A. The agents administered include PBS, IONPs, DOX (5 and 10 mg/kg), Poly IC (18 mg/kg), IONP-DOX-EBP (DOX 10 mg/kg), IONP-DOX-Poly IC (DOX 10 mg/kg, Poly IC 18 mg/kg), and IONP-DOX-Poly IC-EBP (DOX 10 mg/kg, Poly IC 18 mg/kg). Black dashed arrow indicates tumor growth curve (also black dashed) with free 10 mg/kg DOX treatment. FIG. 9C shows live IVIS images of mice bearing 4T1-luc tumors 48 h after intravascular administration of various agents: (i) PBS, (ii) IONPs, (iii) DOX 5 mg/kg, (iv) DOX 10 mg/kg, (v) Poly IC (18 mg/kg), (vi) IONP-DOX-EBP (DOX 10 mg/kg), (vii) IONP-DOX-Poly IC (DOX 10 mg/kg, Poly IC 18 mg/kg), and (viii) IONP-DOX-Poly IC-EBP (DOX 10 mg/kg, Poly IC 18 mg/kg). FIG. 9D show confocal fluorescence microscopic images of tumor tissue sections harvested from mice treated with various agents shown in 9A. Tumor tissue sections were stained with Annexin V (green) for apoptotic cells and propidium iodide (red) for nuclei. Scale bar=100 µm.

FIG. 10A is an illustration of primary breast tumor and potential metastatic sites in a mouse. FIG. 10B is a schedule of tumor inoculation, treatment regimen, and monitoring. FIG. 10C shows sizes of 4T1-luc tumors of mice under various treatments: PBS, DOX (5 mg/kg each injection) and IONP-DOX-Poly IC-EBP (DOX 10 mg/kg, Poly IC 18 mg/kg each injection) injected intravenously. Five injections were given following the schedule shown in b. *$p<0.05$ between IONP-DOX-Poly IC-EBP and untreated groups, by two-way ANOVA with Turkey's post-hoc test. FIG. 10D shows body weights of mice from all groups (n=6) as a function of time. FIG. 10E shows Kaplan-Meier survival curves of mice treated with various agents. FIG. 10F shows representative fluorescence images of mice from treatment groups: PBS, DOX, and IONP-DOX-Poly IC-EBP. Arrows indicate primary tumor and possible metastatic sites. a: primary tumor, b: liver, c: kidney(s).

DETAILED DESCRIPTION

Triple negative breast cancer is difficult to treat effectively, due to its aggressiveness, drug resistance, and lack of the receptors required for hormonal therapy, particularly at the metastatic stage. The present disclosure provides a multifunctional nanoparticle formulation containing an iron oxide core that can deliver doxorubicin, a cytotoxic agent, and polyinosinic:polycytidylic acid (Poly IC), a TLR3 agonist, in a targeted and simultaneous fashion to both breast cancer and dendritic cells. Endoglin-binding peptide (EBP) is used to target both TNBC cells and vasculature epithelia. The nanoparticle demonstrates favorable physicochemical properties and a tumor-specific targeting profile. The nanoparticle induces tumor apoptosis through multiple mechanisms including direct tumor cell killing, dendritic cell-initiated innate and T cell-mediated adaptive immune responses. The nanoparticle markedly inhibits tumor growth and metastasis and substantially extends survival in an aggressive and drug-resistant metastatic mouse model of triple negative breast cancer (TNBC). The multifunctional nanoparticle formulation described herein is a platform for substantially improving the therapeutic efficacy for treating metastatic TNBC.

Figure 1A:
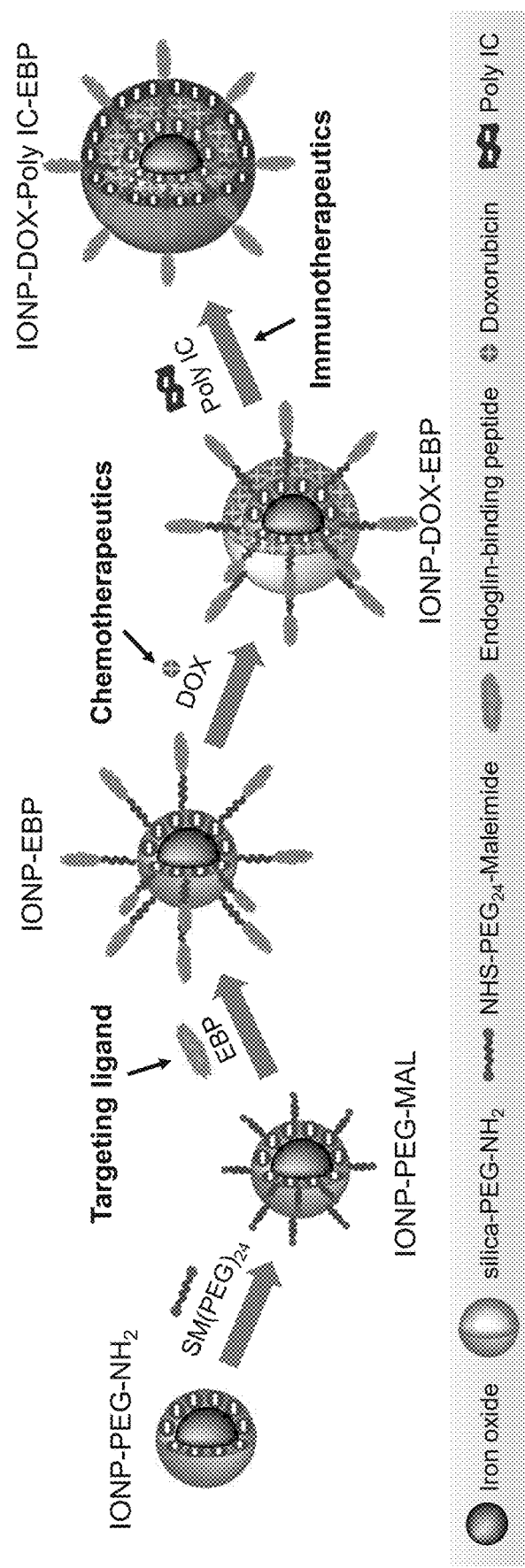
FIG. 1A is a schematic illustration of a representative multifunctional nanoparticle of the disclosure (EBP-modified and DOX/Poly IC loaded nanocarrier) and its preparation.

In one aspect, the disclosure provides a multifunctional nanoparticle for targeted therapeutic drug delivery. A schematic illustration of a representative nanoparticle of the invention and method for its preparation is shown in FIG. 1A.

In one embodiment, the nanoparticle comprises:
(a) an iron oxide core having silica-polyethylene glycol coupled thereto to provide an iron oxide coated core;
(b) a cytotoxic agent reversibly associated with the coated core;
(c) an immunomodulating agent reversibly associated with the coated core; and
(d) a tumor targeting agent associated with the coated core.

As used herein, the term "silica-polyethylene glycol" refers to a siloxane-crosslinked polyethylene coating. The preparation of the siloxane-crosslinked polyethylene coating is described below.

In the nanoparticle described herein, the cytotoxic agent and immunomodulating agent are reversibly associated with the nanoparticle's coated core. As used herein, the term "reversibly associated" refers to the delivery (i.e., release) of the cytotoxic agent and immunomodulatory agent from the nanoparticle once the nanoparticle arrives at the site of cytotoxic agent delivery (e.g., a targeted site such as a lysosome where the lysosome's environment results in release of at least a portion of the cytotoxic agent and at least a portion of immunomodulatory agent from the nanoparticle). The nanoparticle selectively delivers the cytotoxic agent and immunomodulatory agent and does not release the cytotoxic agent or the immunomodulatory agent prematurely, such as in the blood stream (circulatory system).

In certain embodiments of the nanoparticle described herein, the cytotoxic agent forms a first layer surrounding the coated core.

In certain embodiments of the nanoparticle described herein, the immunomodulating agent forms a second layer surrounding the first layer.

In certain embodiments, the cytotoxic agent is a chemotherapeutic drug. In certain of these embodiments, chemotherapeutic drug has a net charge of equal or more than +1 at physiological pH. Representative suitable cytotoxic agents include doxorubicin, daunorubicin, epirubicin, idarubicin, irinotecan, topotecan, mitoxantrone, vinblastine, and cisplatin. In certain embodiments, the cytotoxic agent is doxorubicin.

The nanoparticle described herein includes an immunomodulating agent. Suitable immunomodulating agents include agonists of any receptor in innate or adaptive immune response, other immunomodulators, or other immunomodulating agents, such as checkpoint inhibitors (anti-PD-L1 and anti-CTLA-4), cytokines, agonists, and adjuvants. In certain of these embodiments, the immunomodulating agent is a Toll-like receptor 3 (TLR3) agonist, a Toll-like receptor 7 (TLR7) agonist, or a Toll-like receptor 8 (TLR8) agonist. In certain embodiments, the immunomodulating agent is a Toll-like receptor 3 (TLR3) agonist. In certain of these embodiments, the immunomodulating agent is polyinosinic:polycytidylic acid (PolyIC).

The nanoparticle described herein includes a tumor targeting agent. Suitable tumor targeting agents include tumor target ligands or peptides against triple negative breast cancer, tumor target ligands against tumor vasculature endothelia cells, such as Arg-Gly-Asp (RGD) peptide, Asn-Gly-Arg (NGR) peptide, anti-VEGFR (2C3), Pegaptanib, tumor target ligand folic acid against folate receptor, and transferrin against transferrin receptors overexpressed by breast and other types of cancer. In certain embodiments, the tumor targeting agent is endoglin-binding peptide (EBP).

In certain embodiments of the nanoparticle described herein, the cytotoxic agent is doxorubicin, the immunomodulating agent is polyinosinic:polycytidylic acid (PolyIC), and the tumor targeting agent is endoglin-binding peptide (EBP).

In certain embodiments of the nanoparticle described herein, the ratio of iron/cytotoxic agent ranges between 10:1 and 1:10 (w/w); the ratio of iron/immunomodulating agent ranges between 10:1 and 1:10 (w/w); and the ratio of iron/targeting agent ranges between 10:1 and 1:10 (w/w).

In another embodiment of the nanoparticle described herein, the nanoparticle consists of:
(a) an iron oxide core having silica-polyethylene glycol coupled thereto to provide an iron oxide coated core;
(b) a cytotoxic agent reversibly associated with the coated core;
(c) an immunomodulating agent reversibly associated with the coated core; and
(d) a tumor targeting agent associated with the coated core.

In a further embodiment of the nanoparticle described herein, the nanoparticle consists essentially of:
(a) an iron oxide core having silica-polyethylene glycol coupled thereto to provide an iron oxide coated core;
(b) a cytotoxic agent reversibly associated with the coated core;
(c) an immunomodulating agent reversibly associated with the coated core; and
(d) a tumor targeting agent associated with the coated core.

For this embodiment, the nanoparticle described herein does not include a component that would materially change the nature of the nanoparticle. For example, would not include a therapeutic agent other than a cytotoxic agent as described herein, an immunomodulating agent other than as described herein, a tumor targeting agent other than as described herein, or any other nanoparticle component.

In another aspect, the present disclosure provides pharmaceutical compositions that include the nanoparticles of the invention in combination with a pharmaceutically acceptable carrier (e.g., dextrose or saline solution for injection).

In another aspect, the present disclosure provides a method for treating breast cancer in a subject. In the method, a therapeutically effective amount of a nanoparticle as described herein is administered to a subject in need thereof. In certain embodiments, the breast cancer is subtype of breast cancer expressing a receptor selected from estrogen positive, progesterone-positive, and human epidermal growth factor receptor 2 (HER2)-positive. In certain embodiments, the breast cancer is triple negative breast cancer (TNBC). In certain embodiments, the breast cancer is metastatic breast cancer.

In certain embodiments, administering a therapeutically effective amount of the nanoparticle results in direct tumor cell killing. In other embodiments, administering a therapeutically effective amount of the nanoparticle results in dendritic cell-initiated innate and/or T cell-mediated adaptive immune response. In further embodiments, administering a therapeutically effective amount of the nanoparticle results in direct tumor cell killing and dendritic cell-initiated innate and/or T cell-mediated adaptive immune response.

It will be appreciated that altering the tumor targeting agent to target other cancer cells, other cancers can be treated (e.g., ovarian, liver, prostate, and kidney cancers, and lymphomas, melanomas, and sarcomas). Accordingly, the present disclosure provides methods for treating other cancers targetable with suitable targeting agents.

In another aspect of the disclosure, methods for inhibiting breast cancer tumor growth in a subject is provided. In the method, an amount of a nanoparticle as described herein effective to inhibit tumor growth is administered to a subject in need thereof.

In a further aspect, the disclosure provides methods for inhibiting breast cancer metastasis in a subject. In the method, an amount of a nanoparticle as described herein effective to inhibit metastasis is administered to a subject in need thereof.

In certain embodiments of the above methods, the breast cancer is triple negative breast cancer (TNBC).

In certain embodiments of the methods, the nanoparticle may be administered to the subject systemically (e.g., intravenous administration).

In a further aspect of the disclosure, methods for making a multifunctional nanoparticle as described herein are provided. In certain embodiments, the method comprises:
(a) forming a layer of silica-polyethylene glycol surrounding an iron oxide core to provide a coated iron oxide core;
(b) associating a tumor targeting agent to the coated core;
(c) forming a first layer of a cytotoxic agent surrounding the coated core; and
(d) forming a second layer of an immunomodulating agent surrounding the first layer to provide a nanoparticle comprising a tumor targeting agent, a cytotoxic agent, and an immunomodulating agent.

In certain embodiments, the coated core has a negative surface charge (i.e., the silica-polyethylene glycol coated core has a negative surface charge).

In certain embodiments, the first layer has a positive surface charge.

In certain embodiments, the second layer has a negative surface charge.

In certain embodiments, the method is a layer-by-layer method. In certain embodiments of these embodiments, the method is a layer-by-layer method in the order of negatively charged silica-polyethylene glycol coating followed by a positively charged cytotoxic agent, then negatively charged immunomodulating agent. The tumor targeting agent may be conjugated before, after or between any of the steps.

The following is a description of the design, preparation, characterization, and properties of representative multifunctional nanoparticles of the disclosure.

The present disclosure provides a multifunctional NP that is capable of targeted delivery of chemo- and immuno-therapeutics simultaneously to tumor microenvironment for treating TNBC. The NP has an ultra-small (8 nm) iron oxide core coated with a layer of negatively charged silica-polyethylene glycol (PEG) as a robust shape-defining template for subsequent conjugations to conserve size with tumor and vasculature target ligand, an endoglin-binding peptide (EBP), a chemotherapeutic drug doxorubicin (DOX) and an immunomodulating agent polyinosinic:polycytidylic acid (Poly IC). EBP is a small 12-mer histidine-rich peptide with high affinity to endoglin, a transmembrane glycoprotein highly expressed in both vasculature epithelia and TNBC tumors. DOX, an anti-cancer drug approved by the FDA for clinical use, acts as a cytotoxic agent that induces apoptosis of breast cancer cells. Poly IC is a virus-mimic double-stranded RNA (dsRNA) that activates both innate and adoptive immune systems to eliminate cancer cells through activating Toll-like receptor 3 (TLR3). Poly IC is safe and well-tolerated by patients. Layer-by-layer assembly (LBL) has drawn significant attention in the field of drug delivery due to its modular tunability, drug loading versatility and capability of controlled drug release. A typical LBL usually requires multiple polyelectrolyte layers for drug protection and assembly stability, which could lead to the aforementioned limitations of oversize and unpredictable pharmaceutical profile. The unique configuration of the NP formation described herein rests on the direct deposition of the alternating layers between the positively charged DOX and the negatively charged Poly IC onto the surface of the negatively charged IONPs without the assistance of additional polyelectrolytes. The NP exhibits physicochemical properties tunable by varying the DOX:Poly IC ratio, small size (53 nm) with high-level colloidal stability and a pH responsive drug release profile. In addition, the iron oxide core provides superparamagnetism that enables magnetic resonance imaging (MRI) while the siloxane-crosslinked PEG coating provides negative charges for loading the positively charged DOX and then the negatively charged Poly IC. Systemic injection of the NP demonstrates a safe and favorable pharmaceutical profile, and the NP targeted-delivers chemo- and immuno-therapeutic agents simultaneously to breast cancer cells and enables a combined chemo-immuno-therapy in a synchronous fashion. The NP described herein inhibits tumor growth and metastasis and extends the survival in both xenografted and orthotopic mouse models of drug-resistant and metastatic breast cancer.

Design of NP for Chemo- and Immune-Therapy

A multifunctional NP that contains a tumor target peptide, a chemo drug, and an immune therapeutic agent, and can elicit anti-cancer immune responses (FIG. 1A). FIG. 1A illustrates the structure and synthesis process of this NP. Iron oxide NPs (IONPs) of 8 nm diameter with siloxane-crosslinked PEG coating were conjugated with a tumor-target ligand (EBP, N-terminal cysteine modified) through an NHS-PEG$_{24}$-maleimide heterobifunctional linker. Negatively charged IONPs are then alternatively loaded with the positively-charged DOX and the negatively-charged Poly IC through a layer-by-layer assembling process. The quantity of DOX loaded is controlled by the thickness of each DOX layer and the number of the layers of DOX and Poly IC.

Figure 1B:
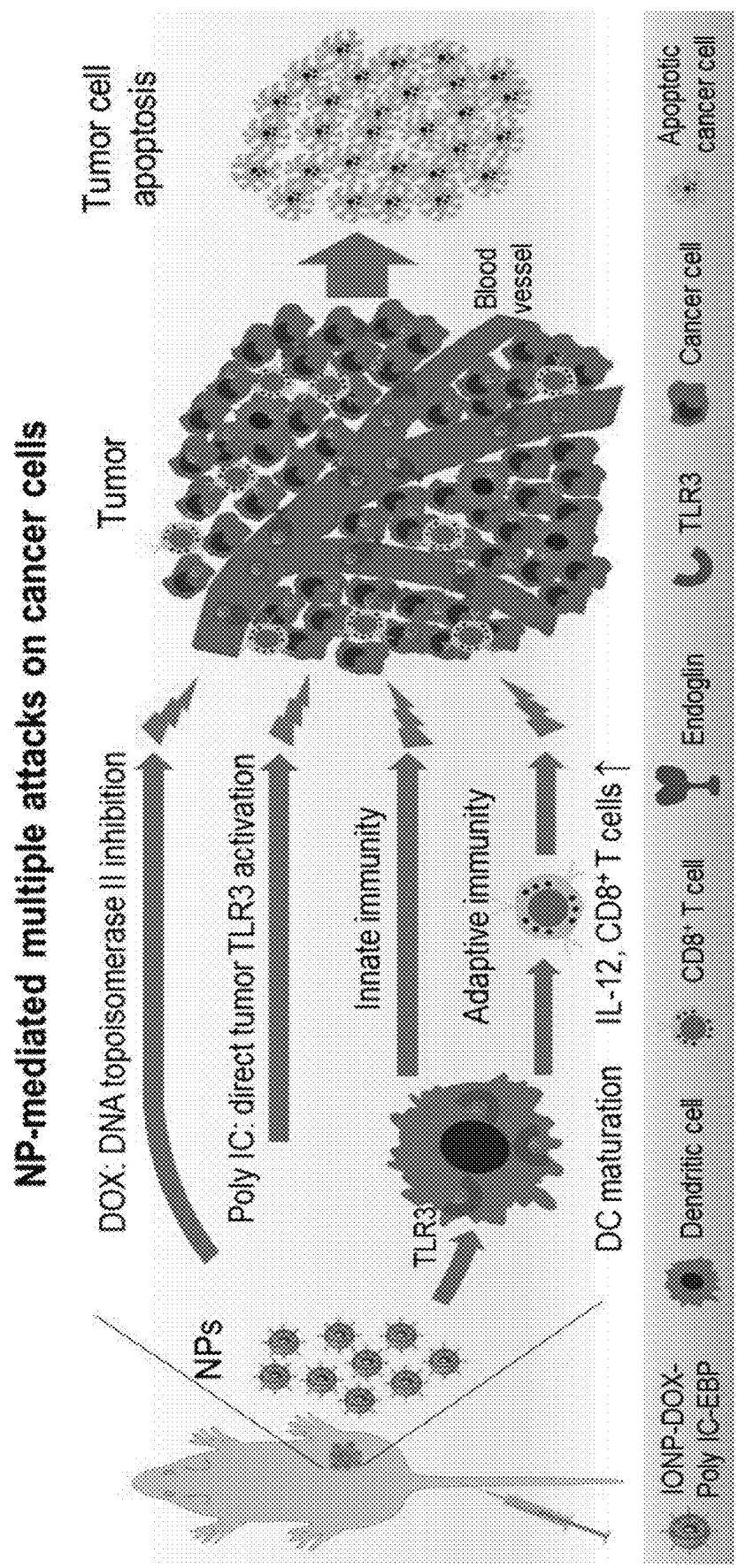
FIG. 1B is a schematic illustration of mechanisms of targeted and combined chemo-immunotherapy for TNBC: Tumor vasculature-targeted delivery of DOX (DNA topoisomerase II inhibition) and Poly IC (activation of TLR3 on tumor cell surface) for direct cancer cell killing; activation of host immune system by NPs through dendritic cell (DC) maturation and secretion of cytokines (e.g., IL-12, etc.), and subsequent activation of anti-cancer adaptive (activation of cytotoxic T cells) and innate (activation of NK cells) immune responses. Combined chemotherapeutic and immunological responses gain maximum possible cancer cell killing.

FIG. 1B shows the possible interactions of the NPs with the tumor microenvironment. The EBP mediates the delivery of the NP loaded with DOX and Poly IC to tumor cells and tumor-infiltrating dendritic cells (DCs) by targeting the tumor vasculature. Once the NP gets into tumor cells, the reduced pH in endosomes (pH 5-6) or lysosomes (pH 4-5) triggers the release of DOX and Poly IC, and consequently induces tumor apoptosis. On the other hand, Poly IC on NPs may also interact with DCs and enter the cells to activate anti-tumor immune response. As antigen-presenting cells, DCs are a player in the initiation and regulation of immune responses. DCs express TLR3 receptors for Poly IC ligand. Upon binding the TLR3 with Poly IC or NP-Poly IC, the maturation of DCs is stimulated to induce the expression of co-stimulatory molecules (CD80 and CD86) and produces cytokines such as IL-12. IL-12 is a potent inducer of anti-tumor immunity through activation of antigen-specific naïve T cells in preclinical models. Furthermore, mature DCs also activate cytotoxic natural killer (NK) cells for tumor cell destruction. Therefore, the designed NP will interact with both tumor and immune system after systemic administration to trigger direct and indirect cancer killing mechanisms in vivo and achieve improved therapeutic outcomes compared to other single-agent treatments.

Physicochemical Properties of NPs

Figure 2A:
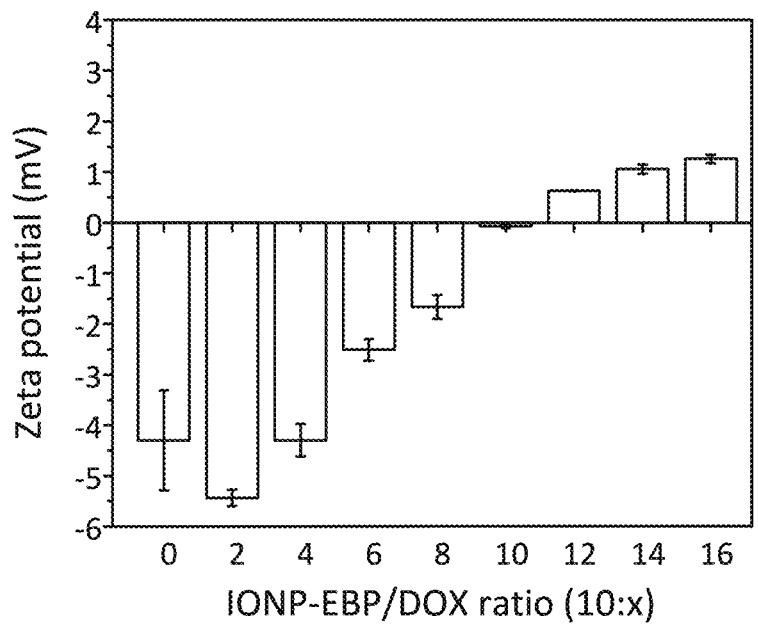
FIGS. 2A-2I show the characterization of a representative multifunctional nanoparticle of the disclosure: DOX and Poly IC loading onto EBP-conjugated IONPs.
Figure 2B:
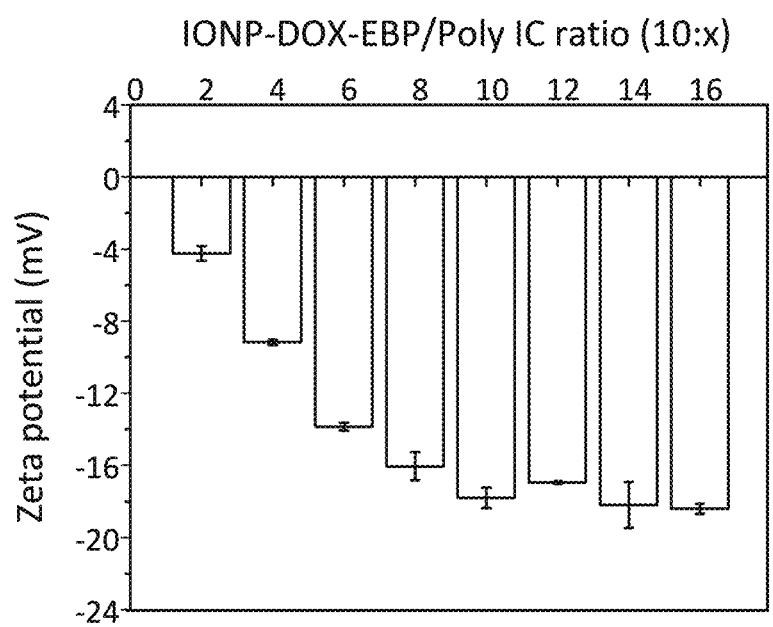
Figure 2C:
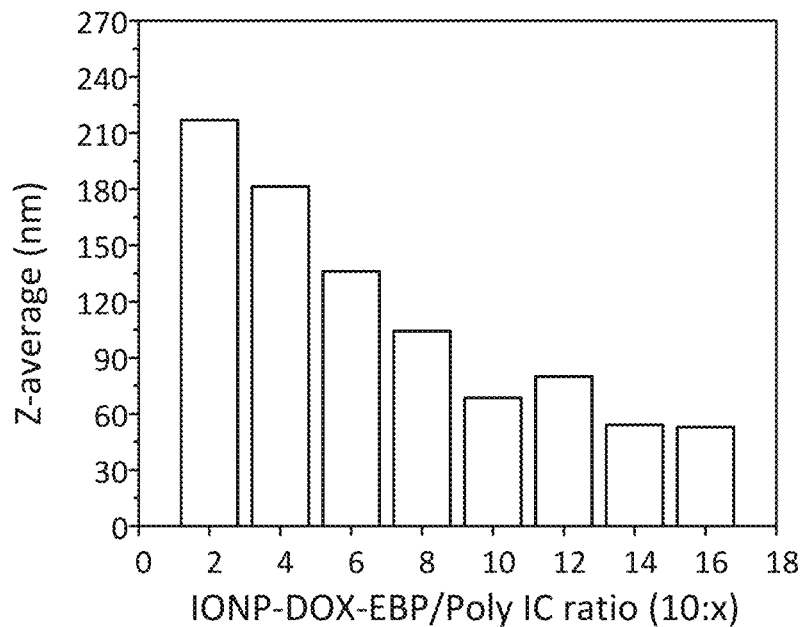

The EBP-conjugated iron oxide NPs (IONP-EBP) had a negative surface charge (about −4.3 mV) that facilitated the loading of positively-charged DOX. A series of NP/DOX ratios (Fe/DOX) were tested to optimize DOX loading. Zeta-potential measurement for IONP-EBP at various NP/DOX ratio showed a gradual change of the surface charge from −4.3 mV to +1.26 mV as NP/DOX ratio varied from 10:0 to 10:16 (FIG. 2A). This change in surface charge also indicated the successful DOX loading. The maximum DOX loading was determined to be Fe/DOX=10:11 (through the ferrozine assay for iron concentration, and UV absorbance at 490 nm for DOX concentration) at reaction ratio of 10:16 where the surface charge was near neutral. Evaluation based on the molar density of about 1.64 nmol NP/mg Fe for IONPs yielded the number of DOX molecules per IONP of about 1156. IONP-DOX-EBP remained small and uniform (z-average=31 nm, PDI=0.15). After removal of free DOX by size-exclusion chromatography, negatively-charged Poly IC was loaded onto IONP-DOX-EBP at different Fe/Poly IC ratios to produce IONP-DOX-Poly IC-EBP. After loading of Poly IC, the surface charge of NPs changed back to negative and reached a plateau of −17.8 mV when the ratio of Fe/Poly IC reached 10:10 (FIG. 2B). Noticeably, the hydrodynamic size of IONP-DOX-Poly IC-EBP increased with the increase in the ratio of IONP-DOX-EBP to Poly IC (e.g., 216.9 nm with Fe/Poly IC 10:2), which may be attributed to the charged-induced aggregation. On the other hand, the increase in Poly IC amount increased the negative charge, which stabilized the NPs. The hydrodynamic diameter of the NP was reduced to a minimum of 53 nm at the Fe/Poly IC ratio of 10:16 (FIG. 2C).

Figure 2D:
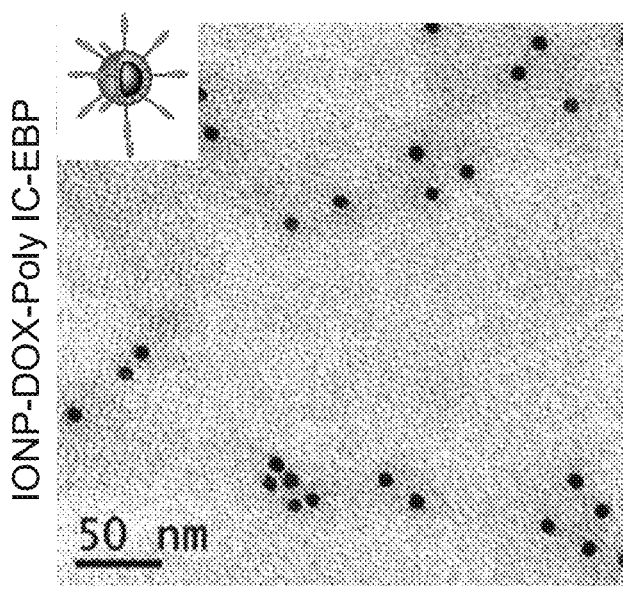
Figure 2E:
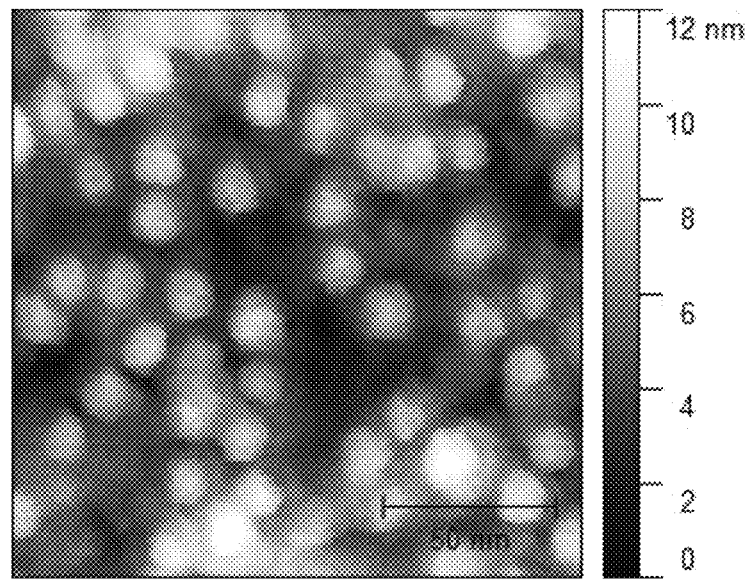
Figure 2F:
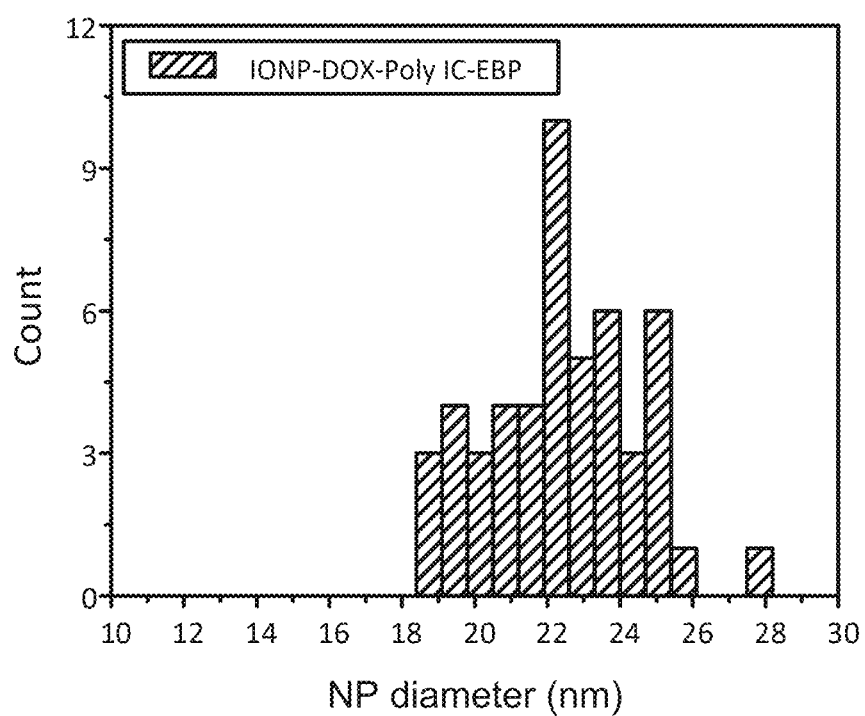

Transmission electron microscopy (TEM) was utilized to characterize the shape and coating of NPs. As shown in the micrographs (FIG. 2D), IONPs have a core size of about 8 nm. As Poly IC is a dsRNA analog and has high electron density, the coating of Poly IC shows as a light-grey envelope around IONP cores (FIG. 2D). AFM was used to further reveal the coating property of IONP-DOX-Poly IC-EBP. FIG. 2E shows the AFM image of the dehydrated NPs deposited on mica surface. Analysis of these AFM images indicates that IONP-DOX-EBP has an average dehydrated diameter of about 18 nm and the Poly IC loading increases the size to about 22.5 nm (FIG. 2F and FIGS. 11A-11C).

Figure 2G:
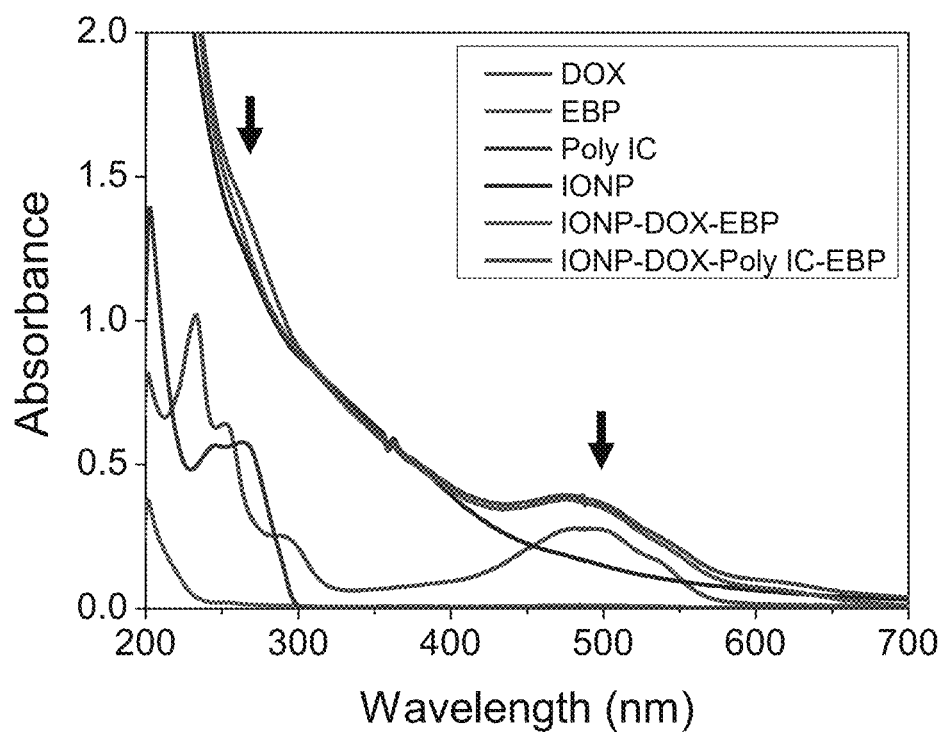
Figure 2H:
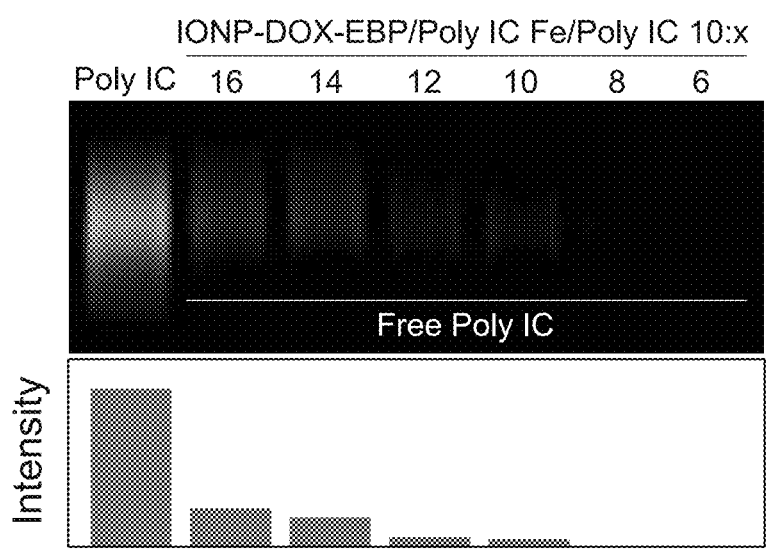

Chemical properties of NPs were further characterized by UV-Vis absorbance (FIG. 2G). The IONPs showed strong absorbance in the UV-Vis region but no characteristic peaks. DOX showed absorbance peaks at 260 nm and 500 nm, Poly IC showed absorbance peaks between 240 and 270 nm, corresponding to their excited states. EBP has no unique characteristic peaks. The spectra for IONP-DOX-EBP and IONP-DOX-Poly IC-EBP show a peak at about 500 nm, characteristic of DOX, confirming the successful loading of DOX in these two NP formulations. An additional peak at about 260 nm in the spectrum of IONP-DOX-Poly IC-EBP further confirms the presence of Poly IC in this NP formulation. To determine how much bound and unbound Poly IC from IONP-DOX-EBP/Poly IC mixtures, unbounded Poly IC was analyzed using agarose gel electrophoresis as free Poly IC could move through the gel and be visualized. The band intensities of Poly IC were evaluated with ImageJ software. Approximately 75% of Poly IC were bound to NPs when IONP-DOX-EBP and Poly IC were mixed at the ratio of Fe/Poly IC=10:16 (FIG. 2H).

Drug Release

Figure 2I:
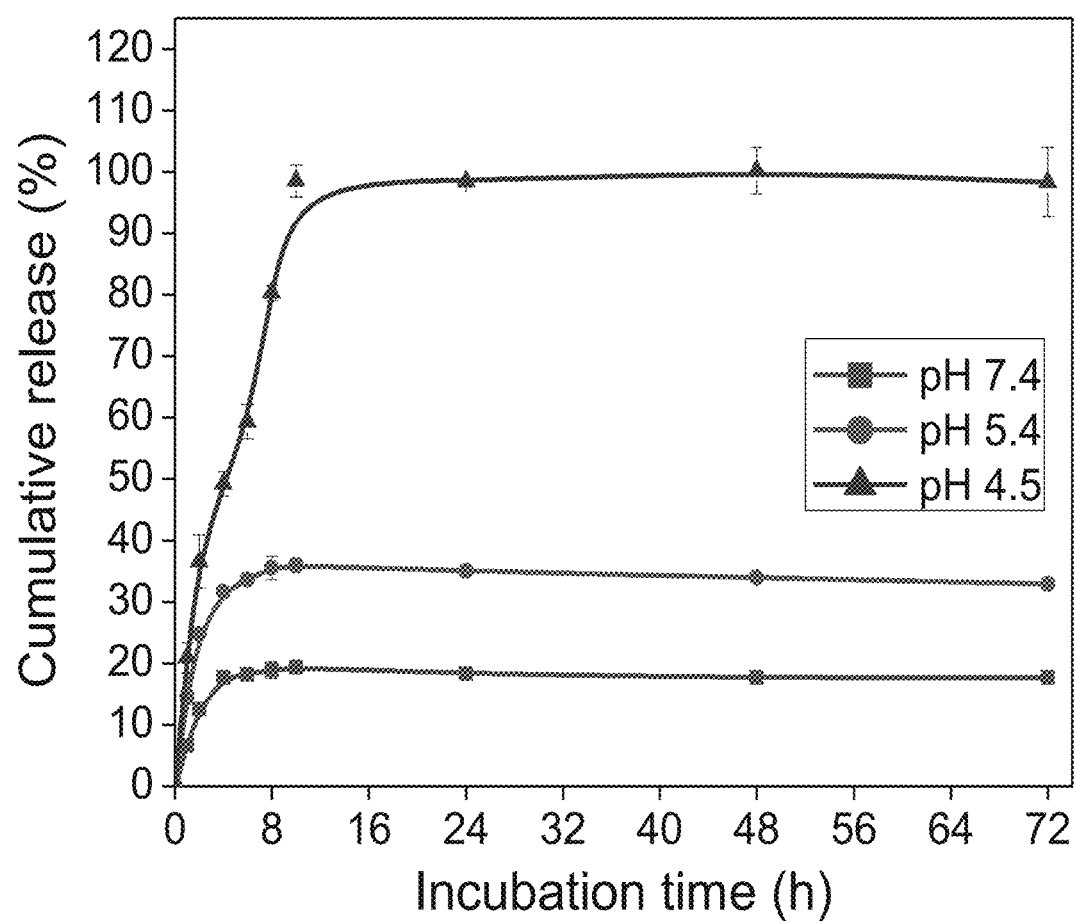

The pH-responsive release of DOX from IONP-DOX-Poly IC-EBP was analyzed using dialysis under three pH conditions, corresponding to those in blood (7.4), cellular endosomes (5.4) and lysosomes (4.5), respectively. The release of DOX under all these conditions were saturated in 10 h (pH 7.4, 4 h; pH 5.4, 8 h; pH 4.5, 10 h). Here a pH-dependent drug release is observed. DOX release is relatively low at high pH values: only 20% of the loaded DOX was finally released at pH 7.4 and 35% of the loaded DOX at pH 5.4; on the contrary, the final release is high at low pH: about 50% of the loaded DOX was released in the first 4 h and about 100% was released in 10 h at pH 4.5 (FIG. 2I). This indicates that when applied in vivo, DOX will be largely released from NPs after the NPs are internalized by target cells and recruited into lysosomes. Combined with the targeted delivery enabled by the tumor-targeting EBP, high-specificity release of DOX from IONP-DOX-Poly IC-EBP in the lysosomes of tumor cells can be achieved to improve therapeutic efficacy and reduce adverse systemic toxicity. Note that DOX and Poly IC were loaded onto NPs through electrostatic interactions. Release of the positively-charged DOX indicates that the negatively-charged Poly IC was released as well because Poly IC and IONP surface were charge repulsive without DOX. Interaction of Poly IC with its receptor TLR3 occurs in endosomes and lysosomes and may not require dissociation of Poly IC from NPs. Therefore, Poly IC can take action as soon as NPs bind to cells and get internalized.

NP Cellular Uptake and Cancer Cell Killing

Figure 3A:
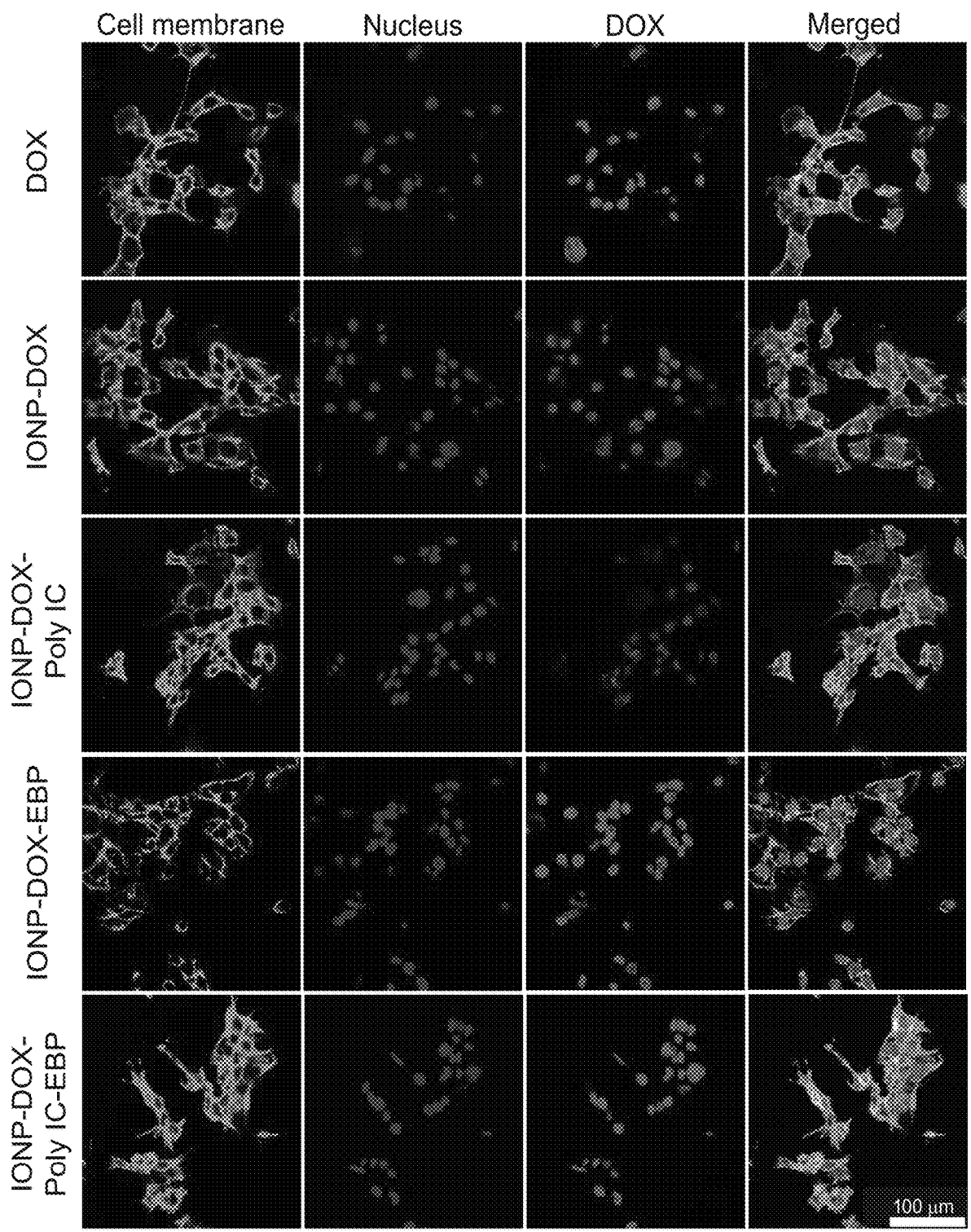
FIGS. 3A-3F show cellular uptake and therapeutic effect of various agents on 4T1 cells. For the cellular uptake study, 10 μg/mL DOX or DOX-equivalent NPs ([Fe] about 9 μg/mL) were incubated with cells for 2 h and analyzed.
Figure 3B:
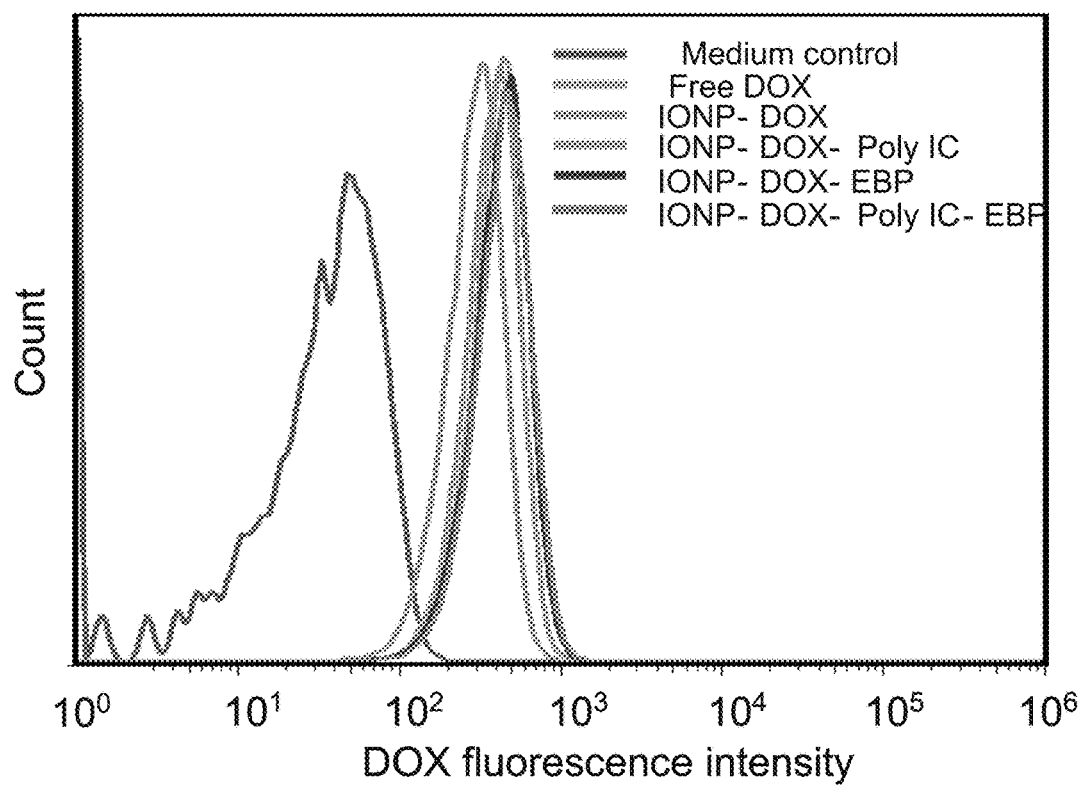
Figure 3C:
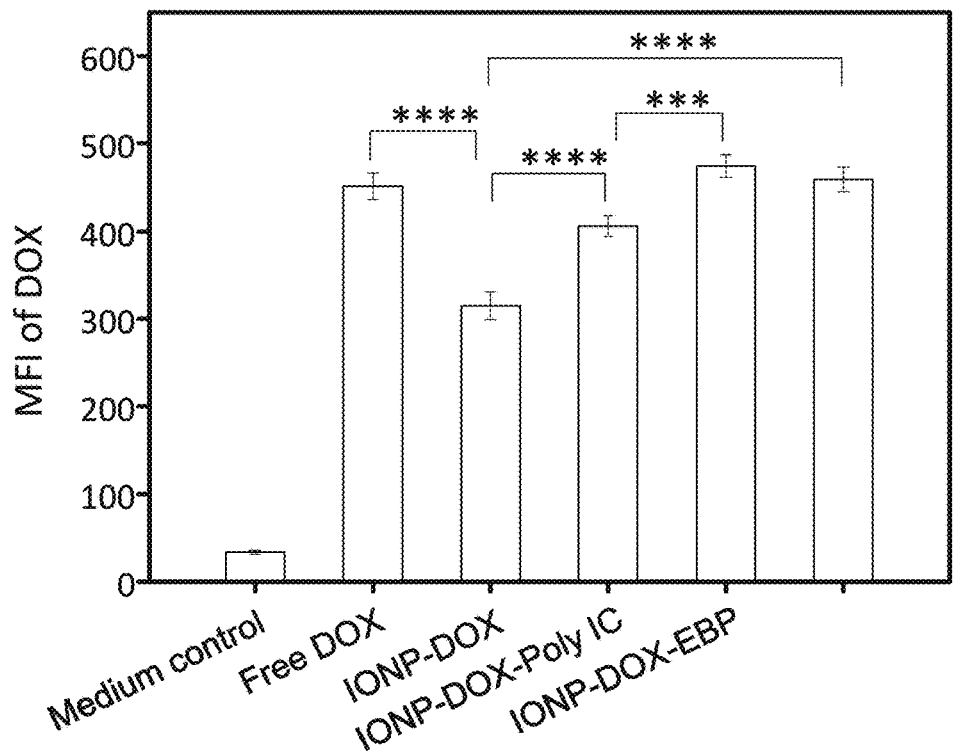

A murine mammary cancer cell line, 4T1, was used to mimic late-stage metastatic breast cancer in human due to its aggressive proliferation and triple negative phenotype. The cellular uptake of IONP-DOX-Poly IC-EBP as well as other agents (for comparison) was characterized by confocal laser scanning microscopy (CLSM) and flow cytometry. For both evaluations, all agents (DOX, IONP-DOX, IONP-DOX-Poly IC and IONP-DOX-Poly IC-EBP) carried the same amount of DOX (10 μg/mL) and were incubated with cells for 2 h. The time point was so selected that the time was sufficient for NPs to enter cells while not causing observable cytotoxic effects. As shown in CLSM images (FIG. 3A), all agents were taken up by cells and were mostly localized in nuclei after 2 h of incubation. However, compared to cells treated with free DOX, cells threated with either IONP-DOX or IONP-DOX-Poly IC (IONPs associated with DOX and Poly IC without EBP ligand) showed decreased fluorescence signals, indicating reduced cellular uptake of these two NP formulations. This was expected because the non-targeting NP-bound DOX enters cells through endocytosis which is slower than free DOX's cell membrane crossing. Cells treated with the targeted NPs (IONP-DOX-EBP or IONP-DOX-Poly IC-EBP), on the other hand, showed similar signal intensities to cells treated with free DOX. EBP targets Endoglin on cell surface and promotes the uptake of NPs. As NPs were not able to freely enter cell nucleus due to their large size for nuclear pore transportation (>5 nm), the observation also indicates that DOX was successfully released from NPs once the NPs entered cells. The result was confirmed quantitatively by flow cytometry measurements. IONP-DOX (MFI=315) showed 30% decrease in signal compared to DOX (MFI=451), while the EBP-conjugated NPs IONP-DOX-EBP (MFI=474) and IONP-DOX-Poly IC-EBP (MFI=459) showed compensation of uptake through targeting effect (FIGS. 3B and 3C). Note that such investigation was based on a single time point.

Figure 3D:
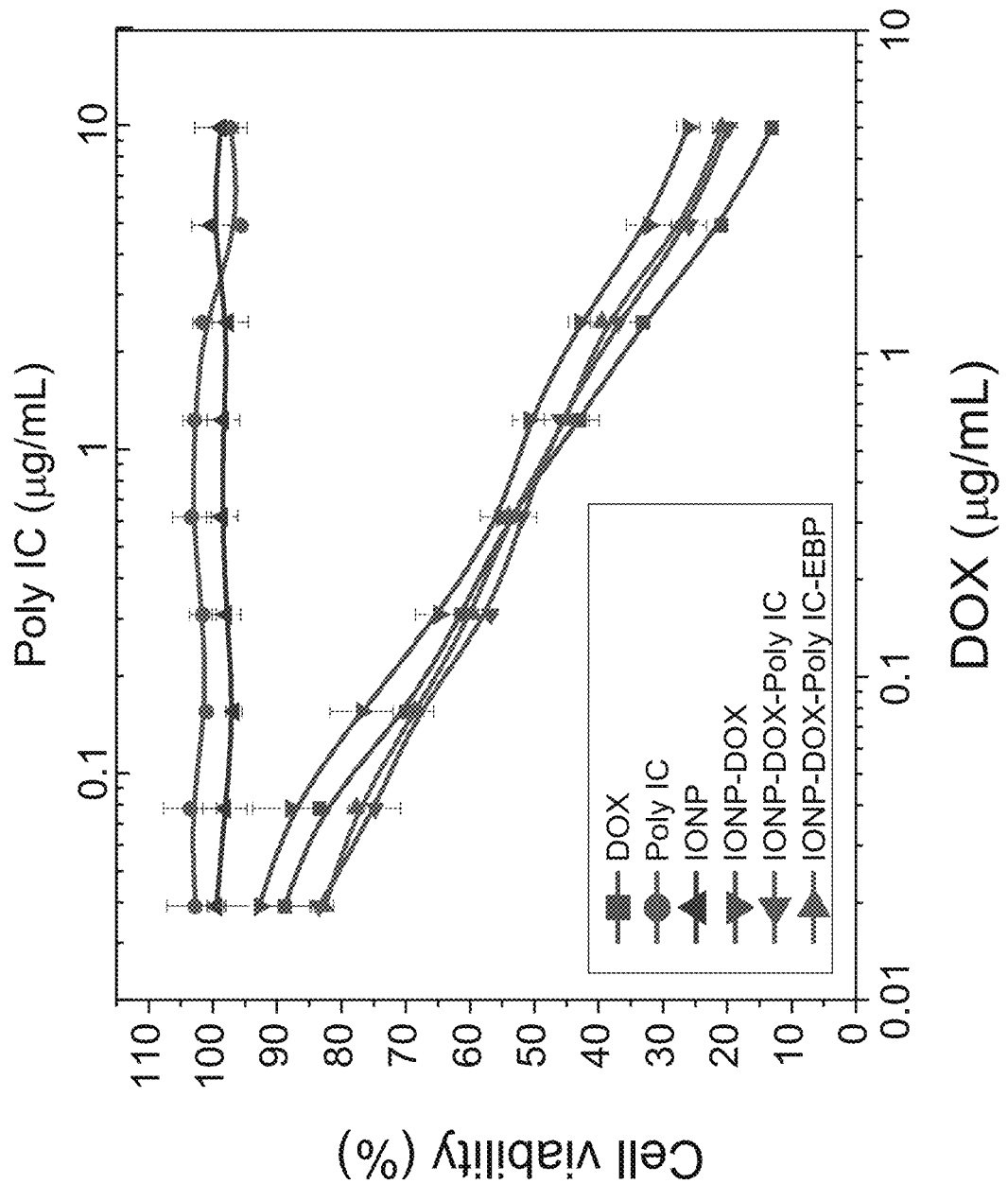

As temperature dependence is an indicator of endocytosis of NPs, a test of cell uptake of free DOX and IONP-DOX-Poly IC-EBP was performed at both 4° C. and 37° C. Significantly, uptake of DOX into cells were mostly inhibited and only 10% of DOX was taken up by cells at 4° C. (FIG. 3D). In contrast, uptake of IONP-DOX-Poly IC-EBP was only partly (about 45%) inhibited at 4° C. The result indicates that, although endocytosis is involved in its uptake, IONP-DOX-Poly IC-EBP may take other pathways to enter cells at low temperature. One possible explanation is that although the NPs had net negative charges, they still had positively charged DOX on the surface. As the molecular structures of coatings on the NP surface could be dynamic rather than rigid, the NP might expose its positively charged regions to the cell membrane during the incubation process, which could facilitate an energy-independent membrane translocation process.

Figure 3E:
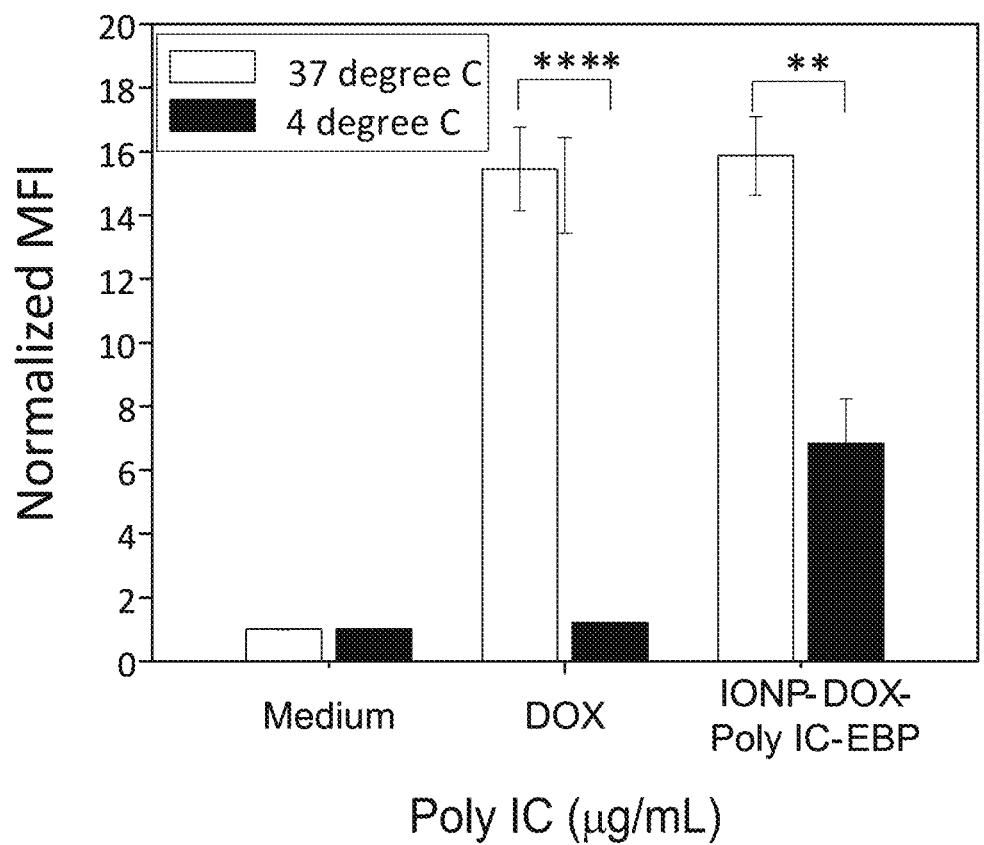
Figure 3F:
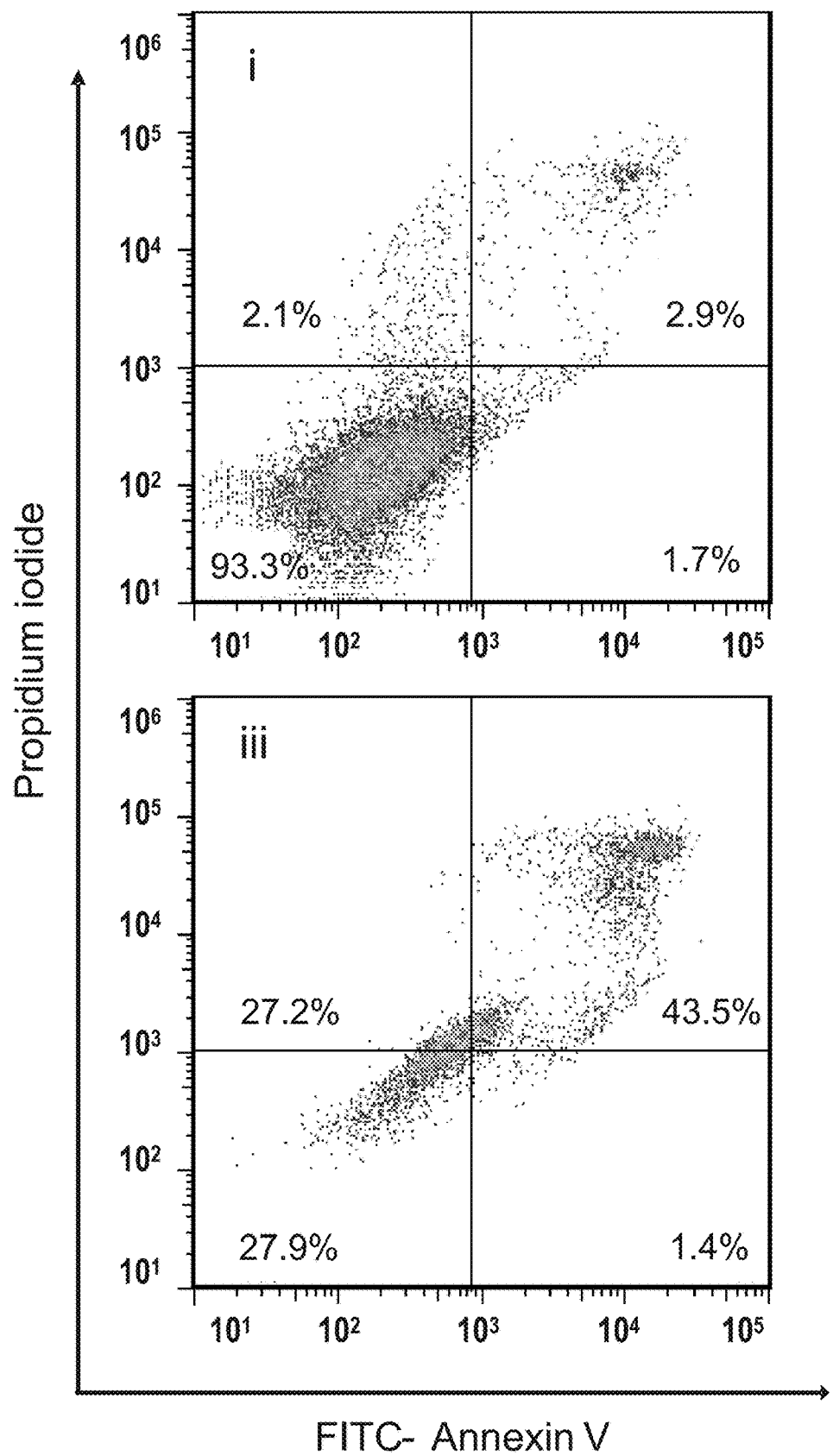
Figure 3F:
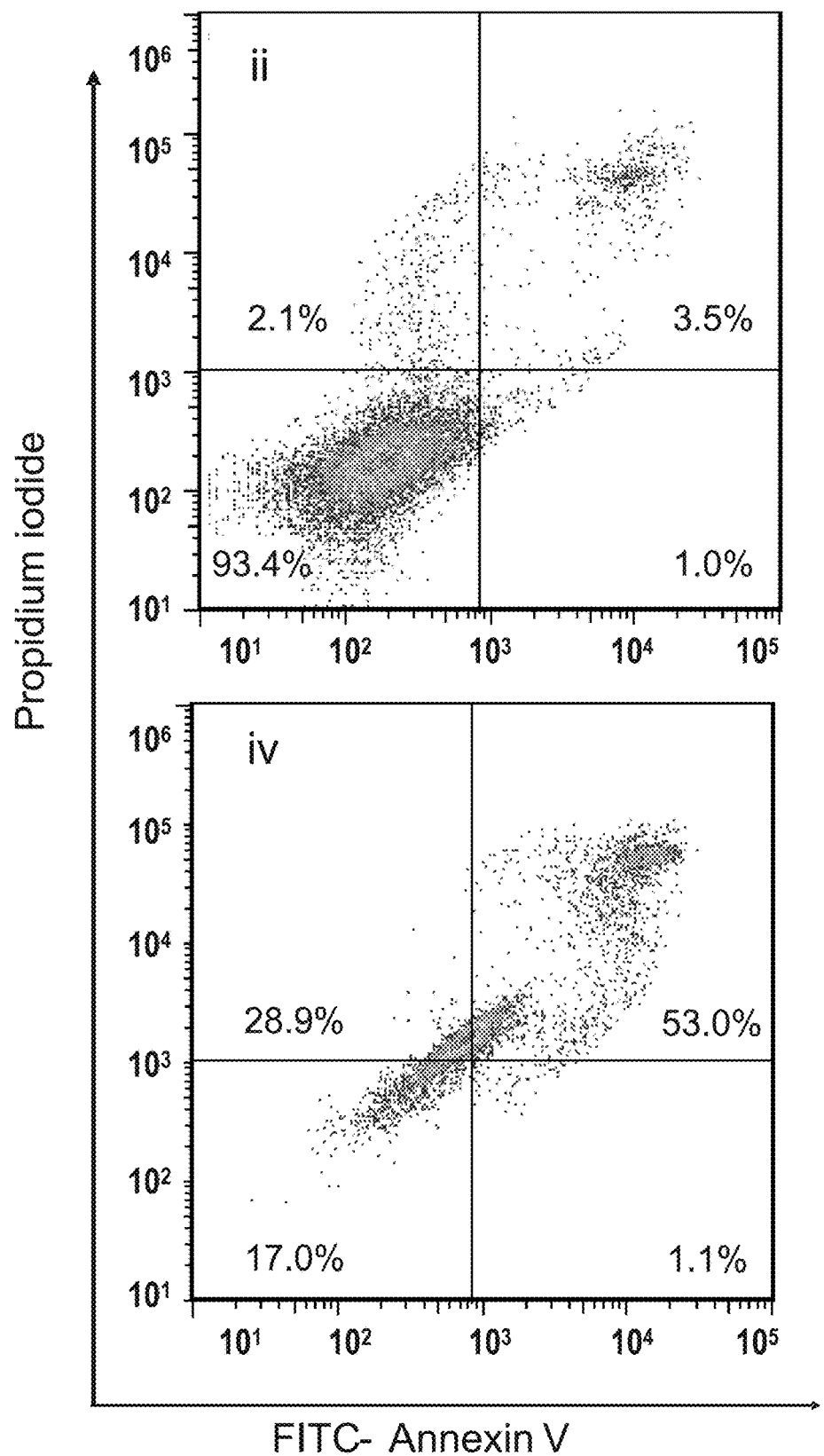

Cellular uptake of these agents determines their therapeutic potency. The viability of cells treated with DOX, Poly IC, IONPs, IONP-DOX, IONP-DOX-Poly IC, and IONP-DOX-Poly IC-EBP, was assessed by the Alamar Blue assay. The results indicate that IONPs were non-toxic to cells. Free Poly IC itself was also non-toxic to cells. The electrostatic repulsion between the negatively charged poly IC and cell membrane significantly limits poly IC's intracellular access so that poly IC alone shows no cell killing effect. Although all DOX-containing NPs showed similar cell-killing profiles, IONP-DOX had slightly lower potency in this regard (IC50 about 0.64 µg/mL) compared to free DOX, IONP-DOX-Poly IC and IONP-DOX-Poly IC-EBP IC50s about 0.36 µg/mL) (FIG. 3E). This result is consistent with cellular uptake study (FIG. 3C), in which the IONP-DOX incurred the least cellular uptake among these agents. Tumor apoptosis assay by Annexin V and PI staining confirmed that the cellular apoptosis induced by IONP-DOX-Poly IC-EBP is comparable to that induced by free DOX (FIG. 3F).

In Vitro Immune Response of Bone Marrow-Derived Dendritic Cells (BMDCs) to NPs

Figure 4A:
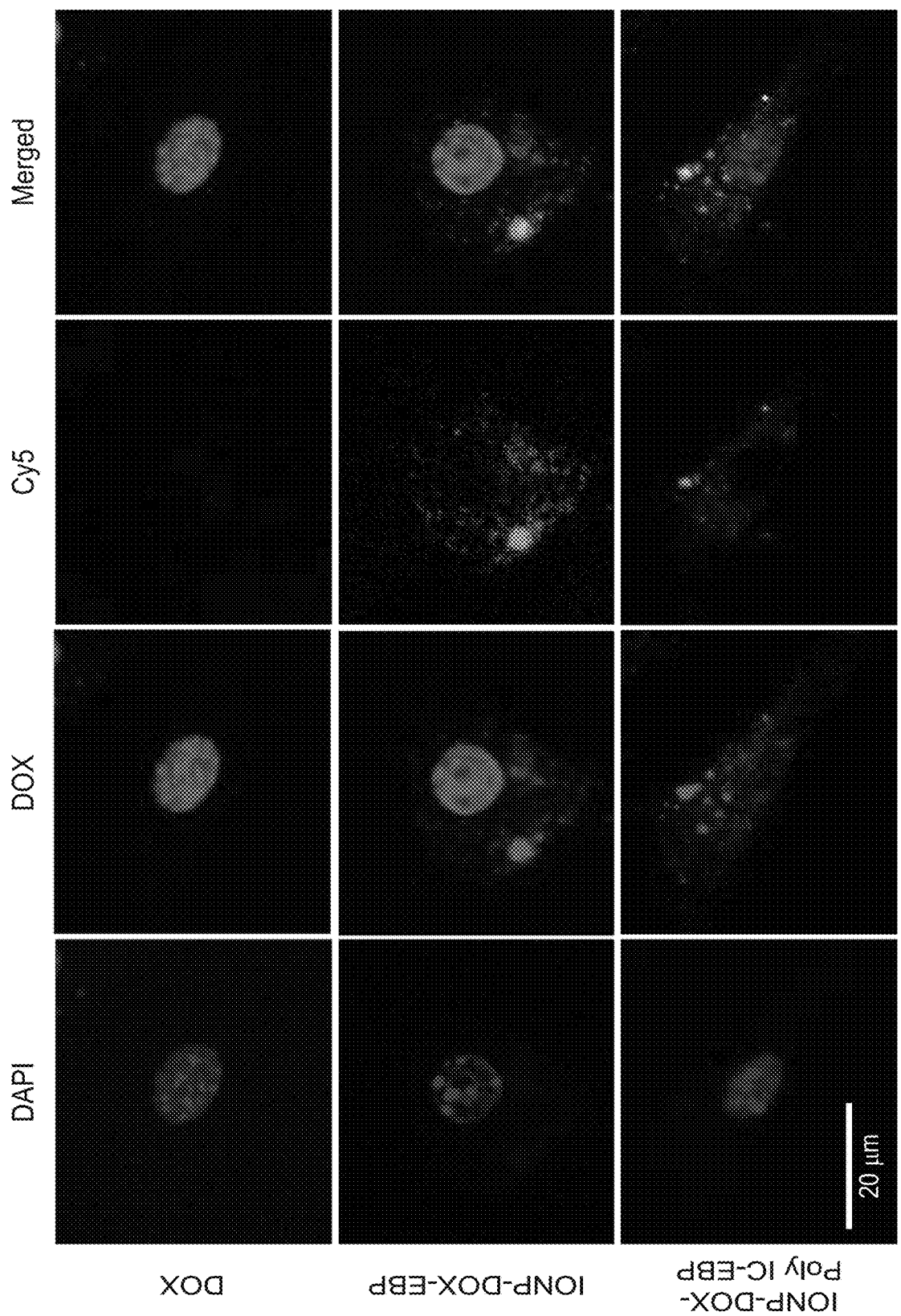
FIGS. 4A-4G show cellular responses of BMDCs to various agents. For all assays, 10 μg/mL Poly IC or an agent carrying equivalent Poly IC was incubated with cells.
Figure 4B:
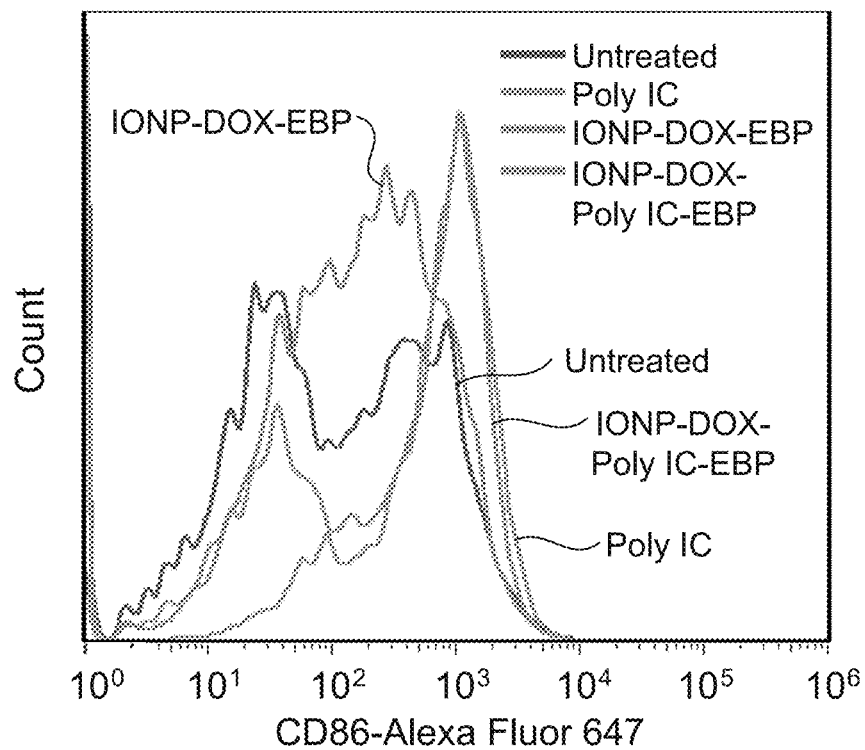
Figure 4C:
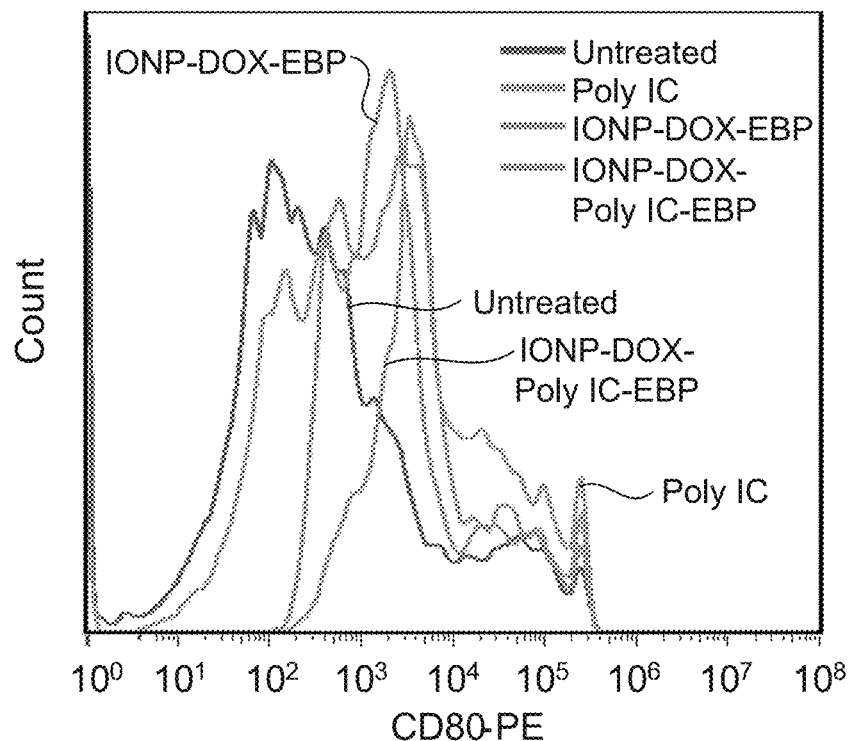
Figure 4D:
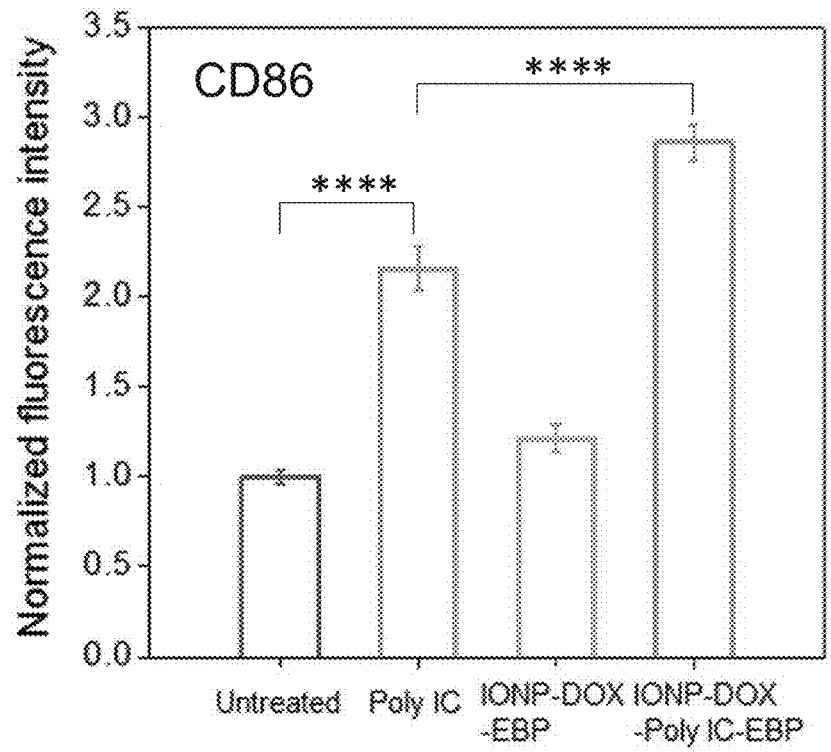
Figure 4E:
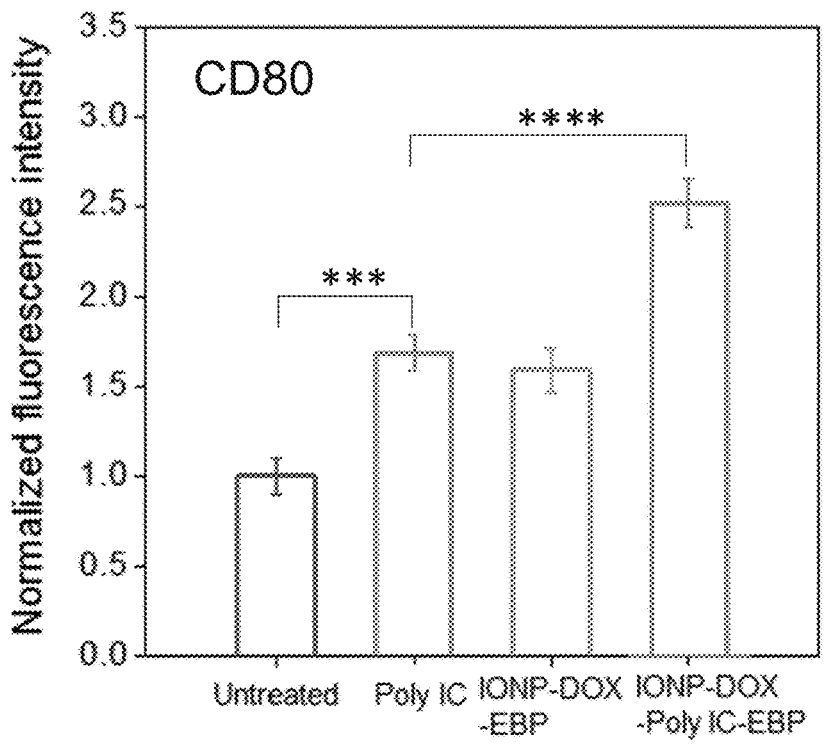
Figure 4F:
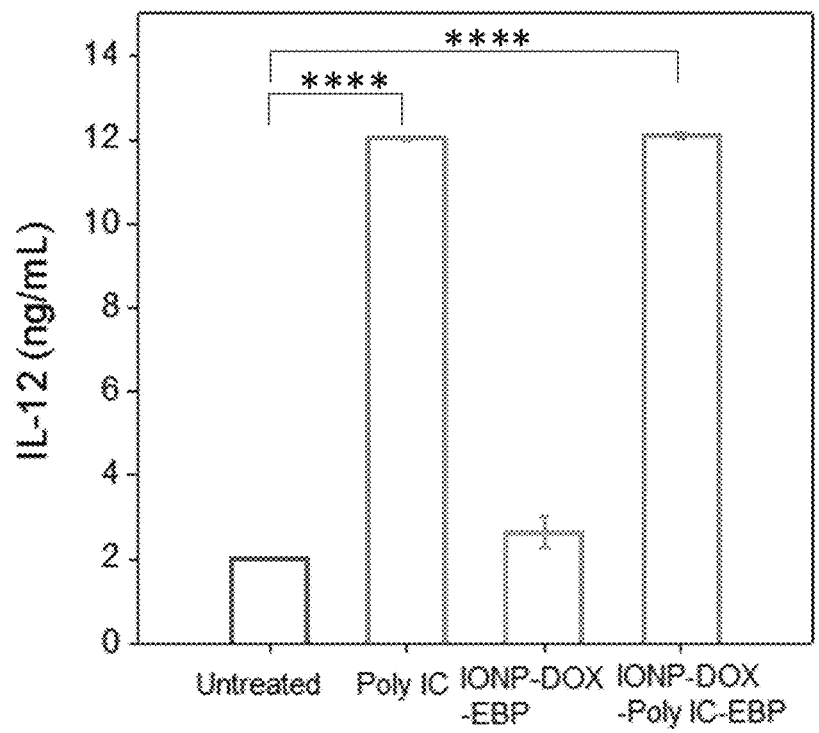
Figure 4G:
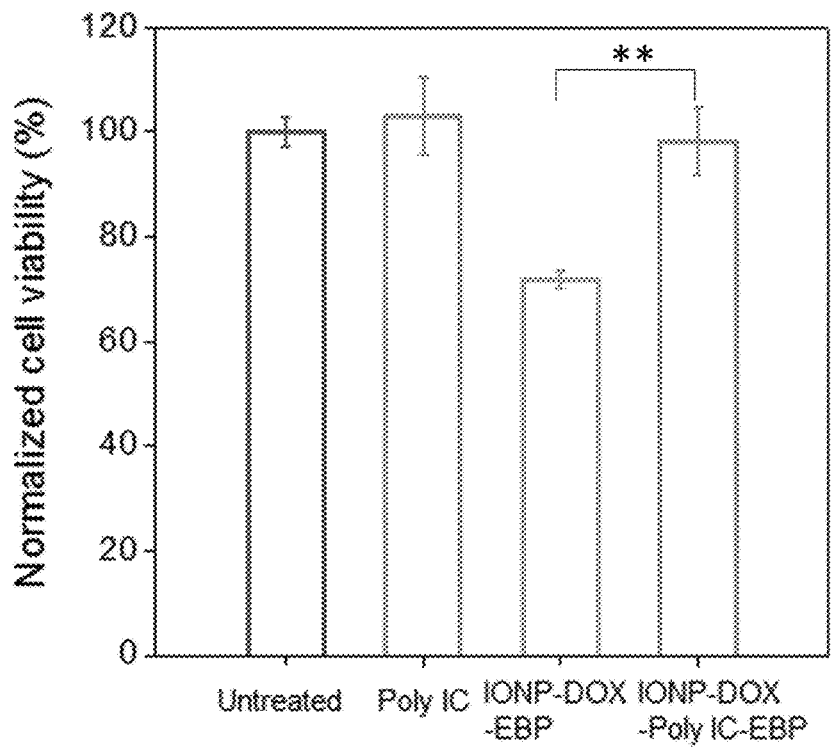

Poly IC exerts anti-cancer immunity through activation of dendritic cells (DCs) and secretion of cytokines. The direct immune response of IONP-DOX-Poly IC-EBP in vitro was examined using bone marrow-derived dendritic cells (BMDCs). All agents were labeled with Cy5 for fluorescence analysis. 10 µg/mL Poly IC or an agent (either IONP-DOX-EBP or IONP-DOX-Poly IC-EBP) carrying equivalent Poly IC was incubated with BMDC cells for 1 h at 37° C. It was seen that although both free DOX and IONP-DOX-EBP can enter BMDCs, DOX from IONP-DOX-Poly IC-EBP remained in cytoplasm without entering nuclei. Although 1 h is not long enough to exclude the likelihood of these NPs to enter the nucleus, the reduced uptake into the nucleus during initial contact suggests the stimulation of BMDCs with reduced cytotoxicity to these cells (FIG. 4A). In fact, DOX is reported to have low toxicity to BMDCs, and does not upregulate their CD80 or CD86 expressions. To examine the maturation of BMDCs, free Poly IC, IONP-DOX-EBP and IONP-DOX-Poly IC-EBP were incubated with cells for 24 h. The expression levels of CD80 and CD86, the BMDC maturation surface markers, were found elevated in cells treated with Poly IC-containing samples (2~2.5× higher than untreated controls). IONP-DOX-Poly IC-EBP showed the strongest therapeutic effect among all the agents as shown by mean fluorescence intensities of anti-CD86 and anti-CD86 quantified by flow cytometry (FIGS. 4B-4E). The enhanced BMDC stimulation by IONP-DOX-Poly IC-EBP is likely due to the NP-mediated Poly IC delivery into endosomes or cytoplasm where TLR3 resides. Further, the production of IL-12 in cellular supernatants was quantified by ELISA. As a product of matured DCs, IL-12 assist in differentiation of naïve T cells into T helper 1 ($T_H1$) effector cells. FIG. 4F indicates that Poly IC and IONP-DOX-Poly IC-EBP induced equivalent production of IL 12. While these agents are expected to have a therapeutic effect on target tumor cells, their potential cytotoxicity is undesirable. The cytotoxicity of these agents was tested against BMDCs. IONP-DOX-EBP showed about 25% of cell killing with a high DOX dose, while the IONP-DOX-Poly IC-EBP had negligible effect to cell viability (FIG. 4G). The low cytotoxicity of IONP-DOX-Poly IC-EBP to DCs is likely due to the combinatory effect of insensitivity of DCs to DOX and reduced NP uptake by the nucleus. These results indicate that IONP-DOX-Poly IC-EBP can both kill cancer cells by DOX and activate immune cells against cancer cells without causing significant toxicity to DCs.

In Vivo Innate and Antigen-Specific T Cell Immune Response

Figure 5A:
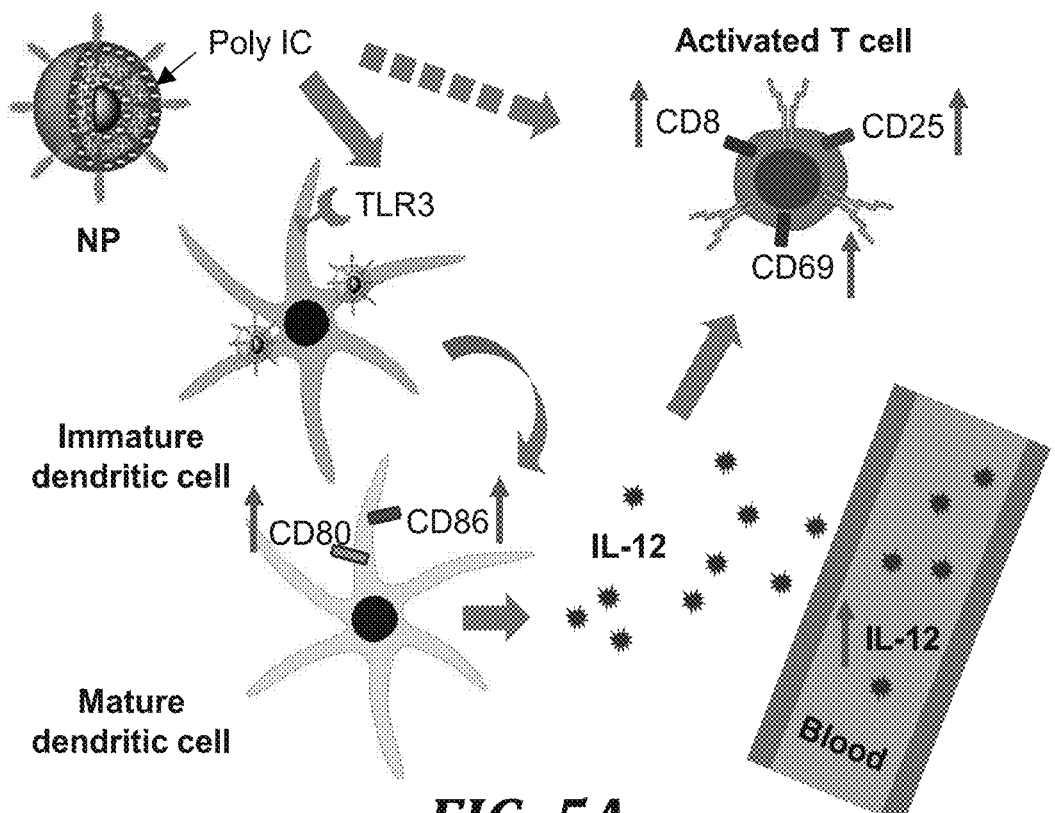
FIGS. 5A-5C show the in vivo assessment of immune response induced by IONP-DOX-Poly IC-EBP.
Figure 5B:
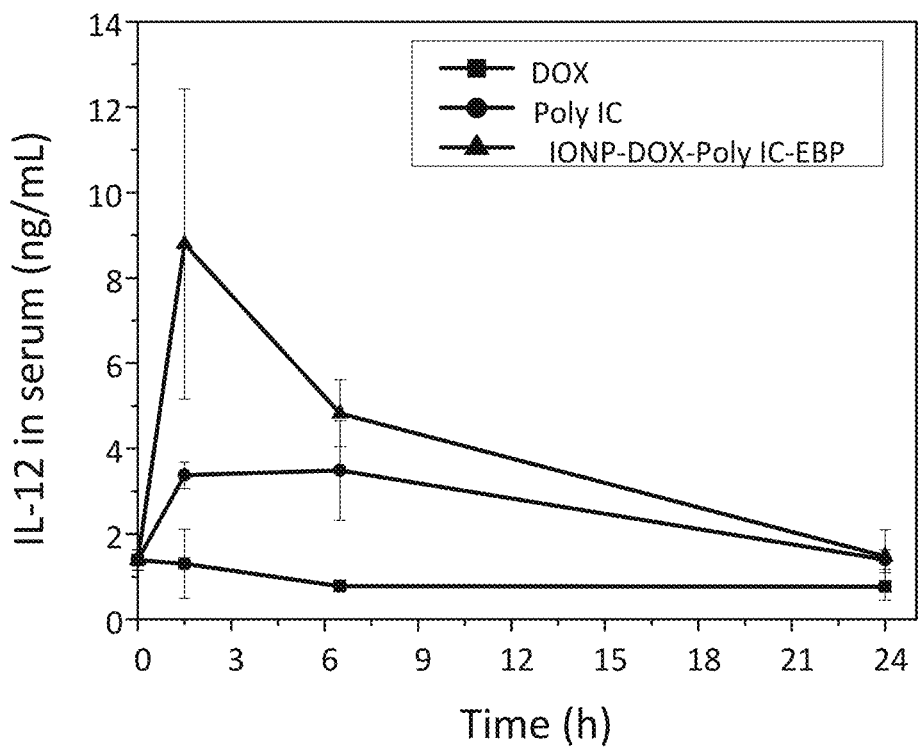

Activation of DCs in mice by Poly IC (i.e., upregulation of CD80 and CD86) would lead to production of IL-12 in blood (FIG. 5A). To confirm if IONP-DOX-Poly IC-EBP can induce IL-12 in vivo, plasma IL-12 levels was quantified in mice after IONP-DOX-Poly IC-EBP, DOX, Poly IC were injected intravenously. 24-h post-injection, blood was drawn from mice and plasma was separated. IL-12 contents in plasma were determined by ELISA assay. The result showed that DOX did not increase the IL-12 level, suggesting that DCs were not activated. In contrast, rapid elevation of the IL-12 level was observed in blood drawn from mice treated with either free Poly IC or IONP-DOX-Poly IC-EBP. The peak of the IL-12 level was reached at 1.5 h post injection and the level then gradually decreased over time. Notably, IONP-DOX-Poly IC-EBP induced a level of IL-12 about 2.6 times higher than free Poly IC (FIG. 5B).

Figure 5C:
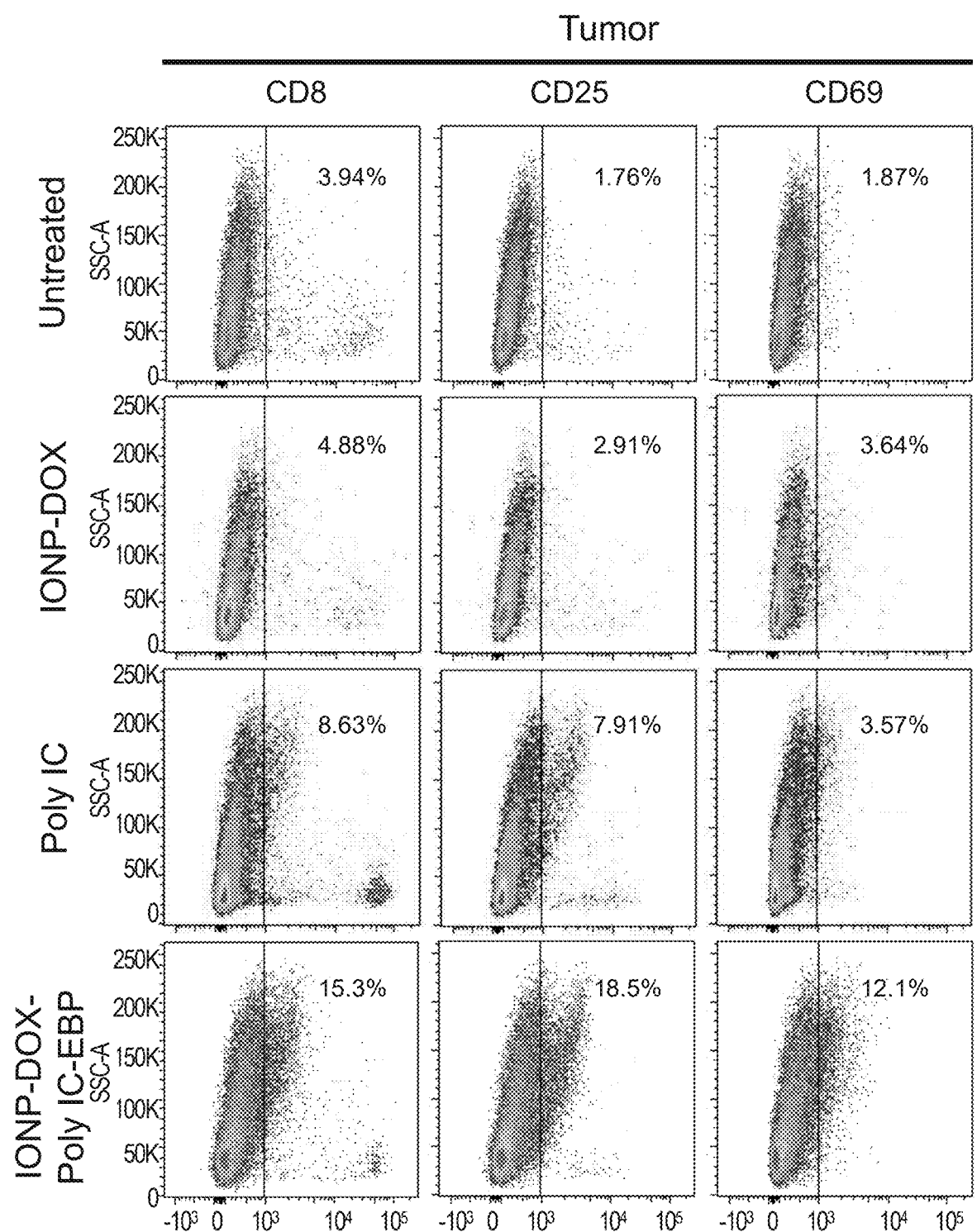
Figure 5C:
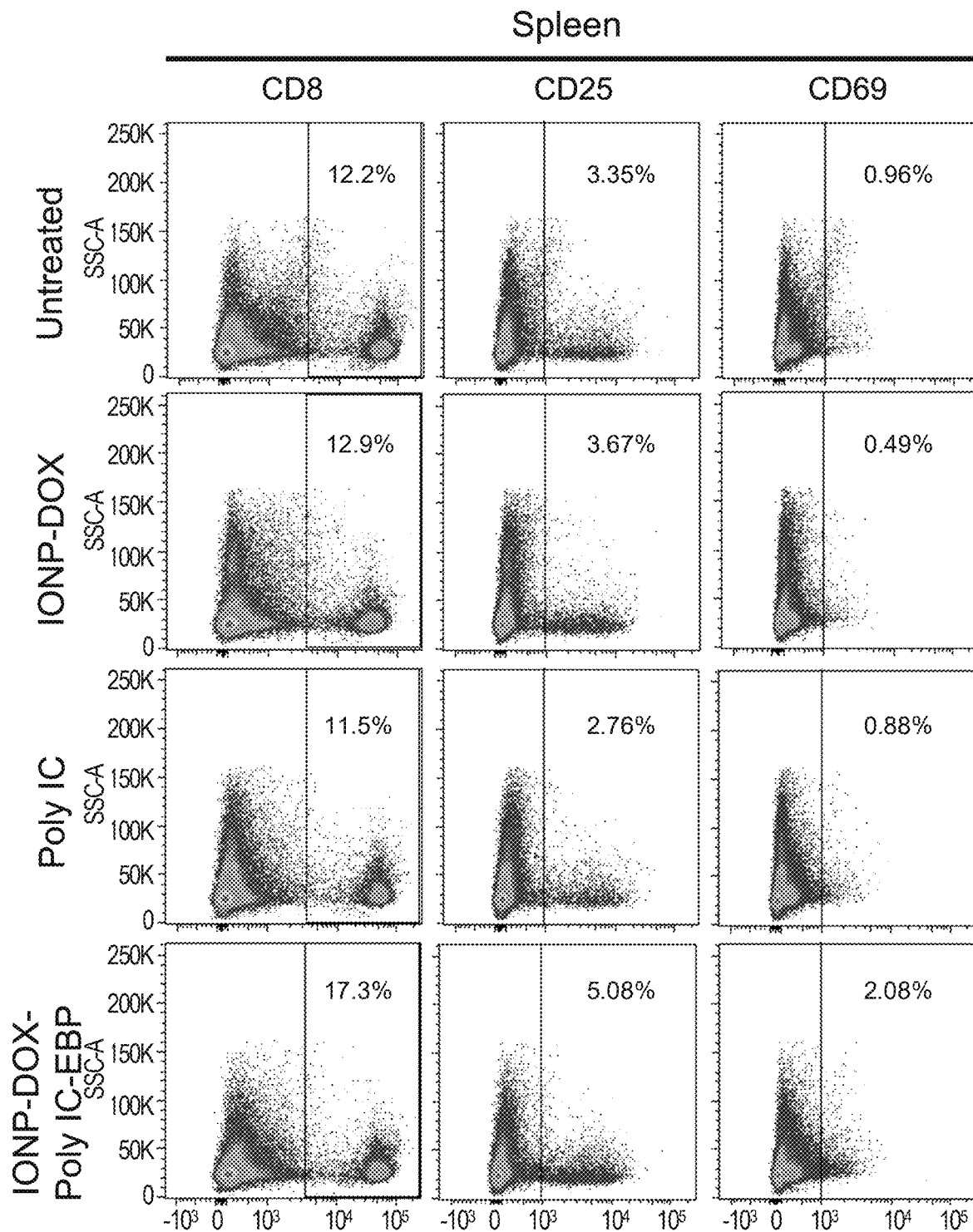

Poly IC has also been shown to directly or indirectly activate T cells and trigger adapted anti-tumor immune response. This process includes the proliferation of cytotoxic T cells (CD8+) and activation of T cells (i.e., upregulation of CD25 and CD69, FIG. 5A). Poly IC containing NPs was tested to determine whether they can activate T cells and kill tumors in tumor-bearing mice. Three days after treatments, tumor bearing mice were euthanized. Tumor and spleen cells were harvested and stained with anti-CD8, anti-CD25, and anti-CD69 antibodies and analyzed by flow cytometry (FIG. 5C). Tumor cells of untreated mice showed low levels of CD8 (3.94%), CD25 (1.76%) and CD69 (1.87%). In contrast, the administration of free Poly IC and IONP-DOX-Poly IC-EBP resulted in a considerable increase of CD8 (8.63% and 15.3%), CD25 (7.91% and 18.5%), and CD69 (3.57% and 12.1%), respectively. Notably, IONP-DOX-Poly IC-EBP was seen to cause more activation of T cells than free Poly IC. In spleen samples, only IONP-DOX-Poly IC-EBP was found to cause a significant increase of activated T cells (CD8: 17.3%, CD25: 5.08%, CD69: 2.08%), which may be attributable to the spleen accumulation of NPs. Free Poly IC is not able to accumulate in spleens with substantial amount. Compared to free Poly IC, IONP-DOX-Poly IC-EBP NPs induced systemic immune response which can produce persistent antitumor effect.

In Vivo MR and NIR Fluorescence Imaging of Tumor-Bearing Mice Treated with IONP-DOX-Poly IC-EBP-Cy5.5

Figure 12A:
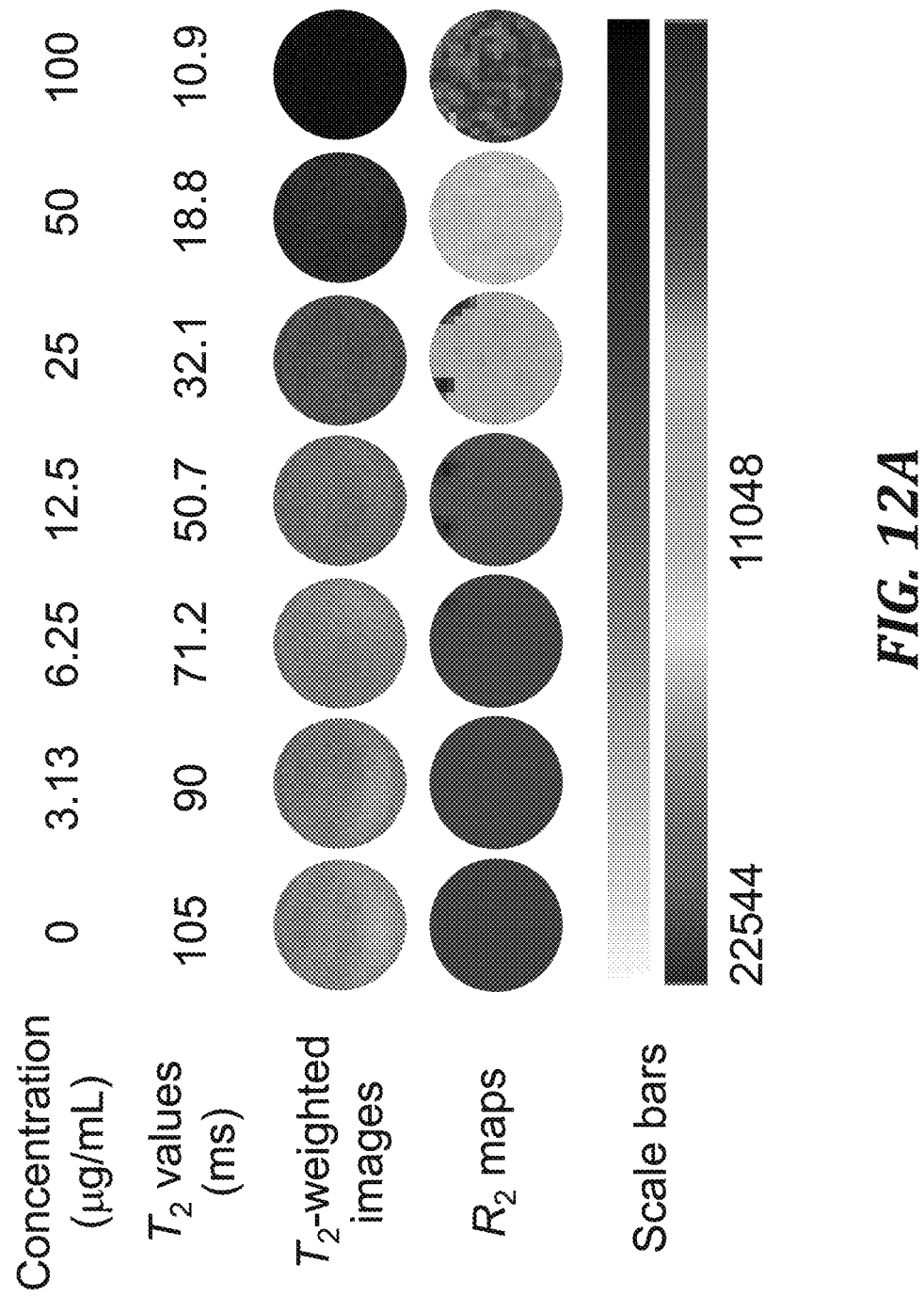
FIG. 12A shows $T_2$-weighted MR images and $R_2$ maps of MRI phantom images of IONP-DOX-Poly IC-EBP at various NP ([Fe]) concentrations.
Figure 12B:
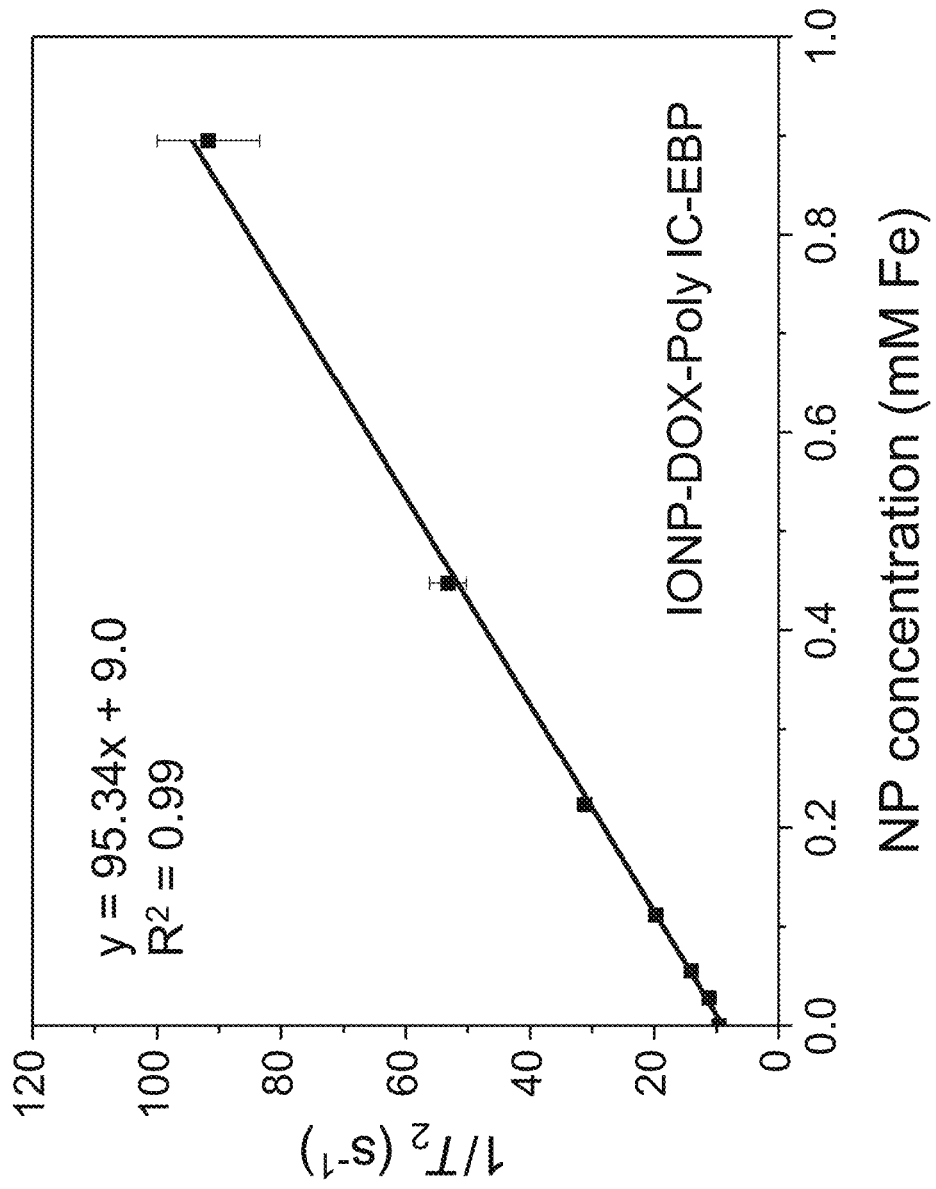
FIG. 12B is a plot of $1/T_2$ as a function of NP ([Fe]) concentration. The slope of the curve is defined as the specific relaxivity of $r_2$.

To further exploit the MRI capability of our multifunctional NP, the magnetic properties of IONP-DOX-Poly IC-EBP were evaluated in solution by MR imaging and then investigated its biodistribution in mice by in vivo MR imaging. As the surface coating may affect the $T_2$ relaxivity of IONPs, the in vitro $T_2$ properties of PEGylated, EBP-conjugated, and DOX/Poly IC co-loaded IONPs were tested. Results showed the $r_2$ value of IONP-DOX-Poly IC-EBP-Cy5.5 is comparable to those reported NPs (FIGS. 12A and 12B).

Figure 6A:
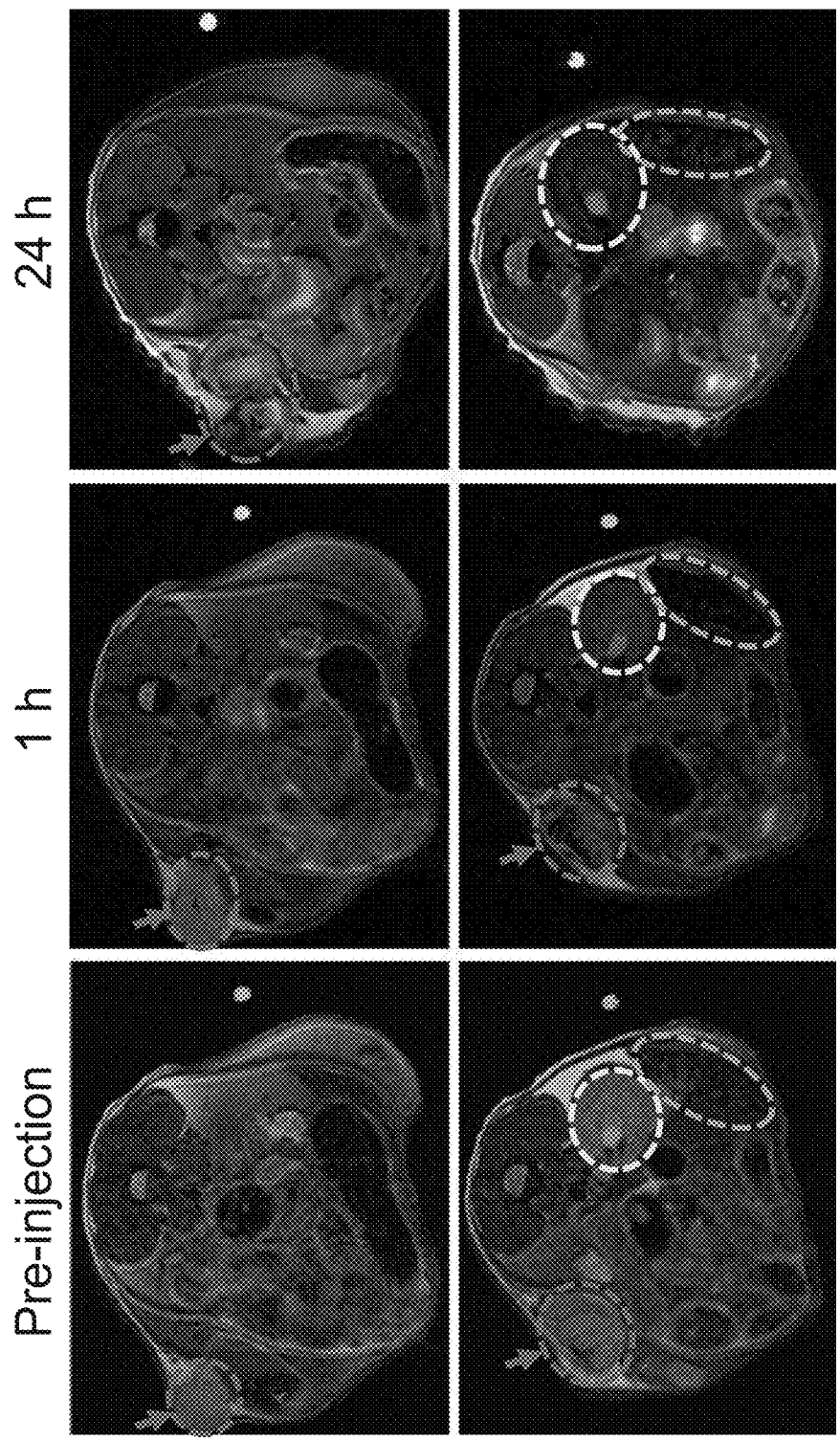
FIGS. 6A-6C show MR and NIR epifluorescence imaging of mice bearing 4T1 tumors and treated using IONP-DOX-Poly IC-EBP-Cy5.5.
Figure 6B:
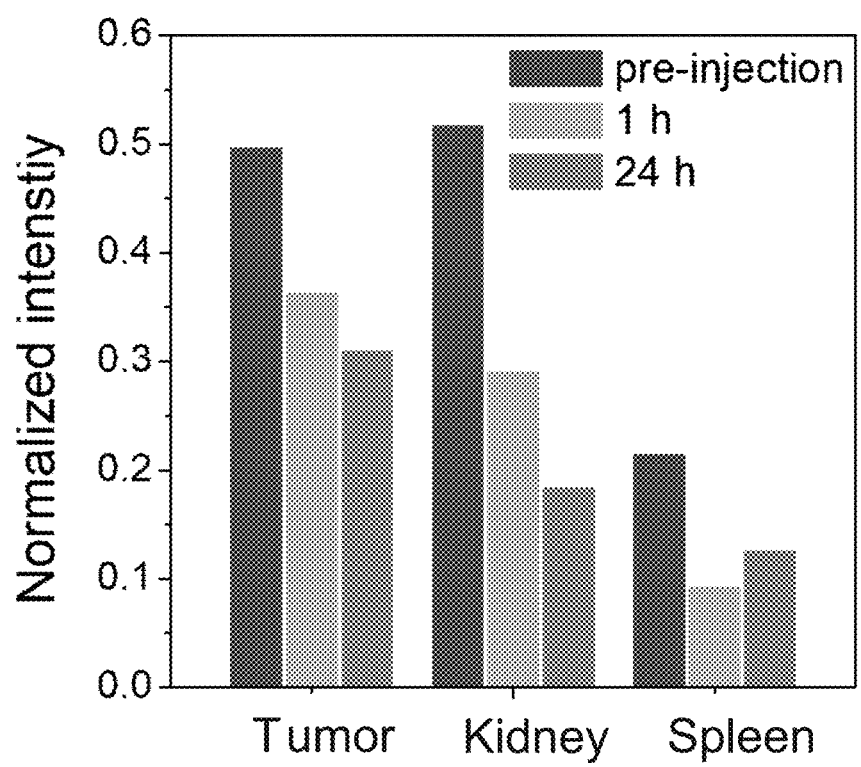

Mice bearing 4T1 tumors were treated with IONP-DOX-Poly IC-EBP-Cy5.5 and MRI images of mice were acquired prior to and one hour post I.V. injection. FIG. 6A shows the images of a representative mouse. One hour after I.V. injection of IONP-DOX-Poly IC-EBP-Cy5.5, darkened areas appeared in tumor, indicating the intratumoral location of the injected NPs. Darkened areas were also found in kidneys and spleen, indicating the accumulation of NPs in these organs. One day after NP administration, more dark areas (increased $T_2$) were observed in tumors, indicating increased NP accumulation. Increased $T_2$ was also observed in kidney, which is apparently due to the renal clearance of NPs. Conversely, the $T_2$ signal intensity in spleen was reduced (FIG. 6B). This observation can be explained as follows. Shortly after injection, NPs were circulating in blood and gradually accumulated in tumor, kidney, and spleen. One day after injection, NPs relocated from spleen to tumors and continuously excreted by the urinary system. The in vivo MRI not only proved the usefulness of these NPs as an effective $T_2$ contrast agent, but also provided information about biodistribution and relocation of NPs in mice.

Figure 6C:
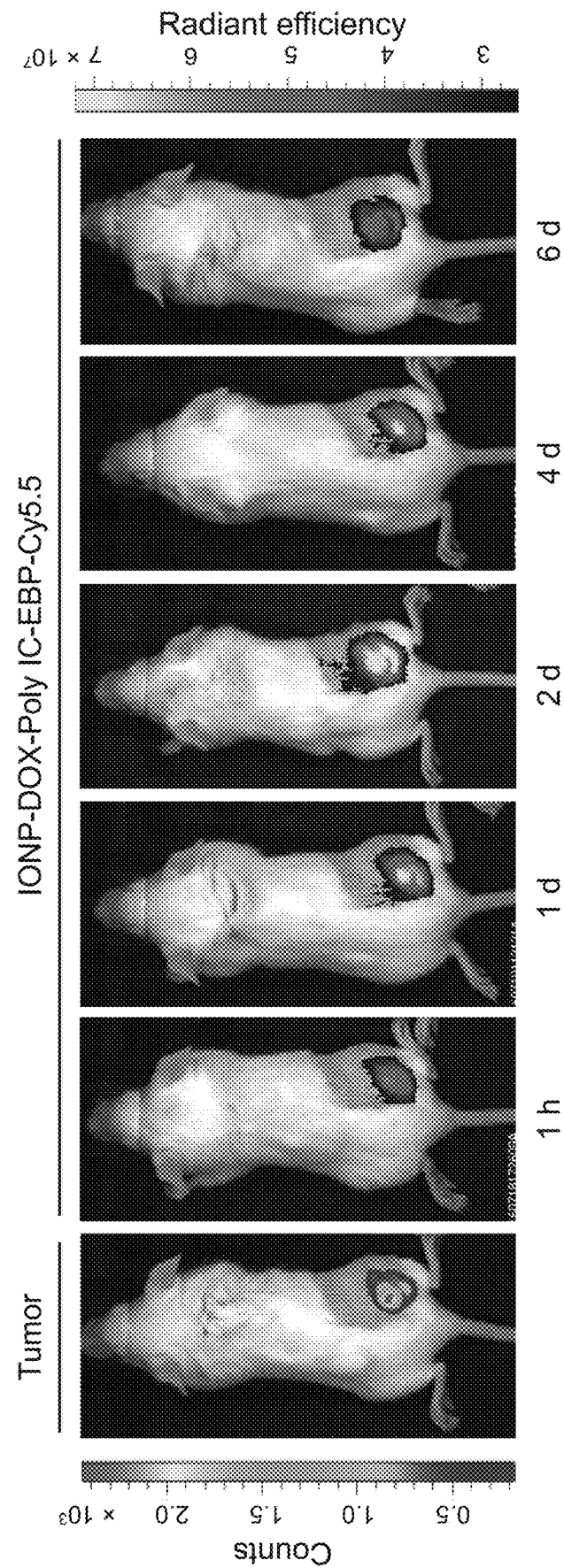

Bioluminescence and fluorescence imaging of live mice was also carried out to validate the in vivo targeting efficacy. IONP-DOX-Poly IC-EBP-Cy5.5 was injected intravenously into 4T1-luc tumor-bearing mice one week after tumor inoculation. The images were taken from 1 h to 6 d after injection. The result showed that the NPs co-localized with tumor at 1 h and continued to accumulate in tumor at 1 d and 2 d, and the accumulation lasted for nearly a week (FIG. 6C). This observation is consistent with cellular uptake studies and in vivo MRI, and confirms targeting of 4T1 cancer cells by EBP both in vitro and in vivo.

Biodistribution and Pharmacokinetics of NPs in a Flank-Tumor Mouse Model

Figure 7A:
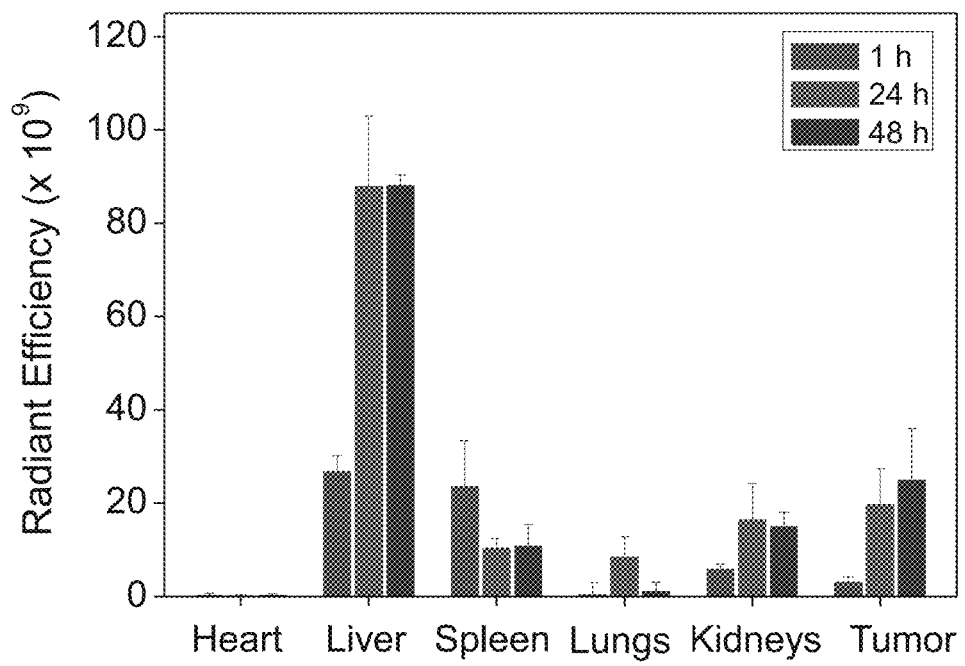
FIGS. 7A and 7B show in vivo biodistribution and pharmacokinetics of IONP-DOX-Poly IC-EBP.

The accumulation of NPs in various organs in tumor-bearing mice was analyzed by quantifying Cy5.5 intensities of Cy5.5-conjugated NPs. Mice were euthanized at 1, 24 and 48 h after NPs injections and organs were harvested. FIG. 7A shows radiant efficiencies (DOX fluence intensity) for various tissues. The results showed that at 1 h, NPs mostly accumulated in liver, spleen, kidneys and started to accumulate in tumor. At 24 h, NPs continued to accumulate in tumor, liver and kidneys, but were being eliminated from spleen. Some NPs were also found in the lungs at 24 h. At 48 h, NP accumulation virtually was unchanged in liver, spleen and kidney remained, but slightly increased in tumor (FIG. 7A). This result agrees well with those obtained by MR imaging (FIGS. 6A and 6B). It should be noted that it is expected that NPs accumulate in the liver in a large quantity as a result of the clearance by the reticuloendothelial system (RES). It is also known that the accumulation of NPs is size-dependent, and the NPs disrobed herein have been prepared with a proper size to minimize the liver accumulation.

Figure 7B:
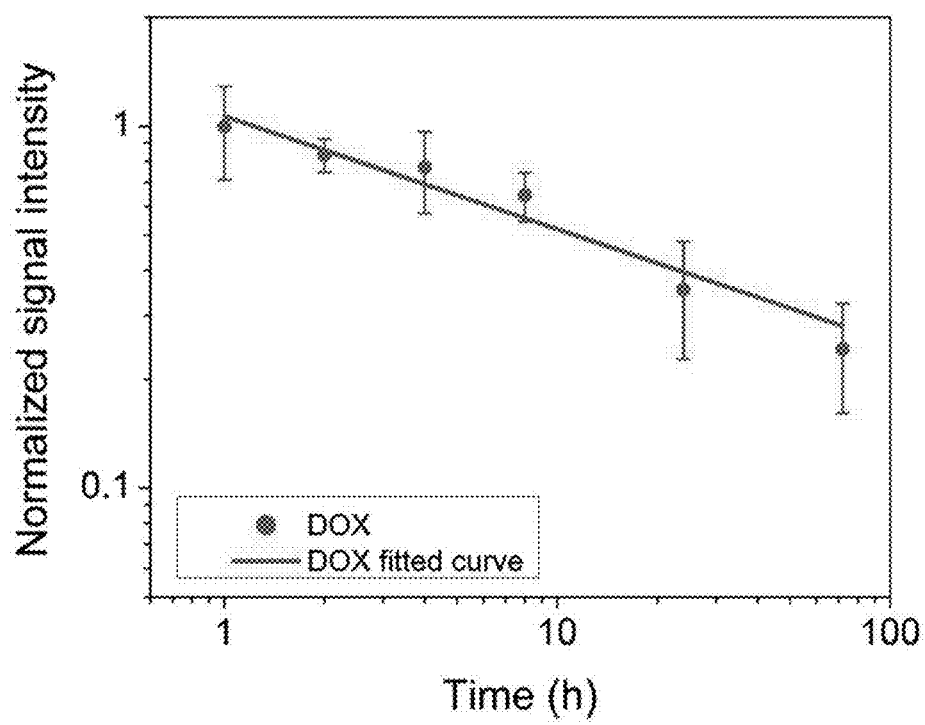

The blood circulation half-time of IONP-DOX-PolyIC-EBP was determined by quantifying DOX fluorescence signals in blood of BALB/c mice over time. The DOX signal intensity versus time relationship is shown in FIG. 7B from which it was determined that the half-lives of IONP-DOX-Poly IC-EBP is 4.8 h. The long blood half-life was primarily attributed to the small and uniform size of NPs, and to the hydrophilic coating of PEG molecules.

Figure 8A:
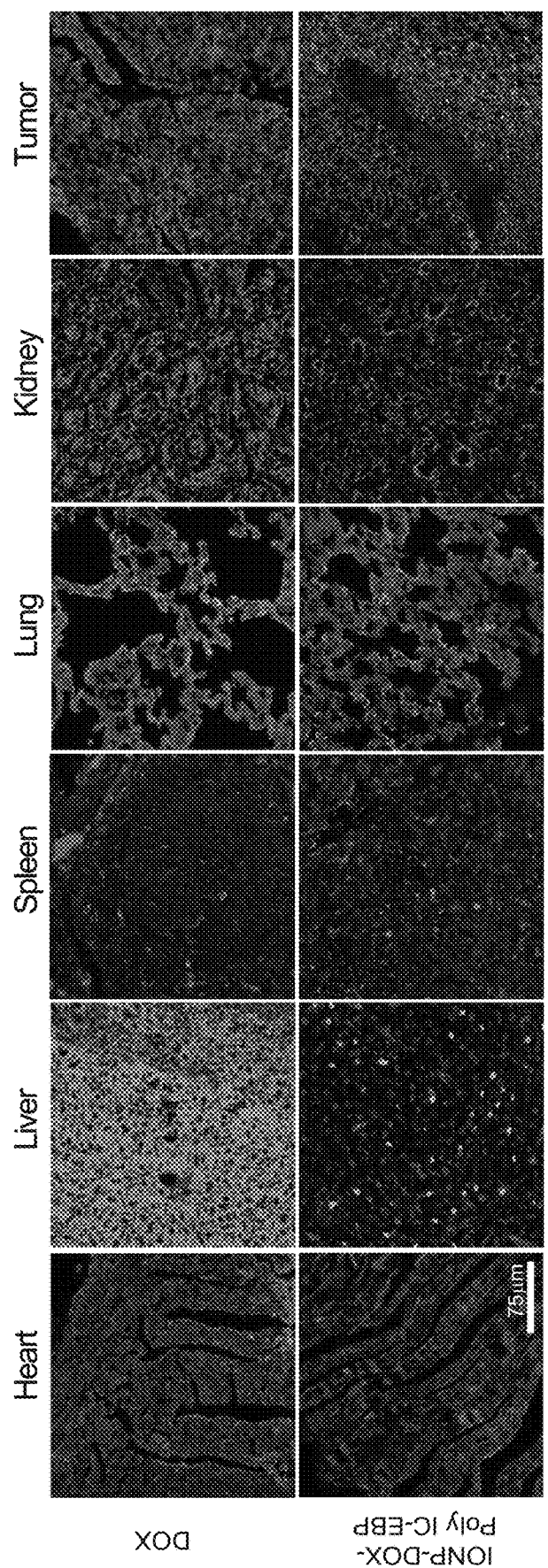
FIGS. 8A and 8B show uptake of DOX into tumor and tissue histology of various organs in mice treated with free DOX or IONP-DOX-Poly IC-EBP. BALB/c mice were treated with saline (negative control), DOX (positive control) or IONP-DOX-Poly IC-EBP (therapeutic agent). DOX dose was 10 mg/kg and Poly IC dose was 18 mg/kg, and tissues were collected 48 h after a single I.V. injection.
Figure 13:
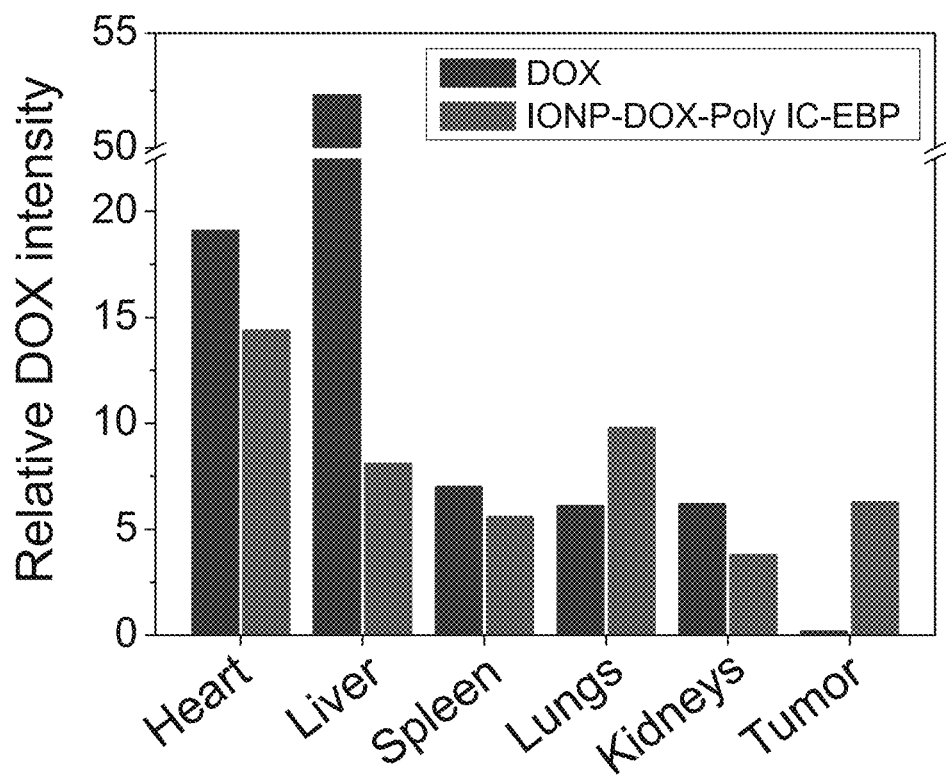
FIG. 13 compares DOX uptake in organs and tumors quantified from FIG. 8A. Relative intensity was calculated by ImageJ software.

Tissue Uptake of DOX and Histopathology in NP and Free DOX Treated Tumor-Bearing Mice To investigate the targeted DOX delivery of IONP-DOX-Poly IC-EBP, the uptake of DOX into various organs of mice administered intravascularly with free DOX or IONP-DOX-Poly IC-EBP (10 mg/kg DOX per mouse) was evaluated. Images of tissue sections of various organs from mice in FIG. 8A shows the deposition of DOX in various organs 48 h post-injection. Significant differences in DOX uptake by liver and tumors were observed. For mice treated with DOX, the liver displayed a strong and evenly distributed fluorescence signal. Previous investigations have suggested that the fluorescence signal might result from original DOX and its fluorescent metabolites by hepatic enzymes. In contrast, the livers from mice treated with IONP-DOX-Poly IC-EBP showed a scattered spot distribution of DOX. No observable DOX signal was found in tumors of mice treated with free DOX. In contrast, strong DOX signals were observed in tumors of mice treated with IONP-DOX-Poly IC-EBP. The DOX was mainly located near blood vessels, likely due to uptake of NPs mediated by overexpressed Endoglin on these vessels. A plot of DOX uptake vs various tissues derived by quantifying fluorescence DOX intensity based on images (FIG. 8A) is shown in FIG. 13. IONP-DOX-Poly IC-EBP has much higher accumulation in tumor than DOX, which explains why IONP-DOX-Poly IC-EBP is much more effective in tumor cell killing than DOX. It is also noted that the distributions of both DOX and IONP-DOX-Poly IC-EBP were heterogenous, presumably due to the heterogenic nature of this type of tumors.

It is worthwhile noting that the 4T1 flank tumor model was used by design for studying the in vivo immune response, tumor targeting, NP biodistribution as well as pathological analysis. The flank tumor model of 4T1 is localized and has little chance to metastasize into other organs compared to the orthotopic model, which facilitates the investigation and interpretation of in vivo targeting and biodistribution (e.g., no tumor metastasizing into lung/liver/kidney to complicate biodistribution and pathological analysis). The orthotopic tumor model, on the other hand, is more clinically relevant and tends to metastasize; thus, it was used for studying the metastasis inhibition and survival analysis.

Figure 8B:
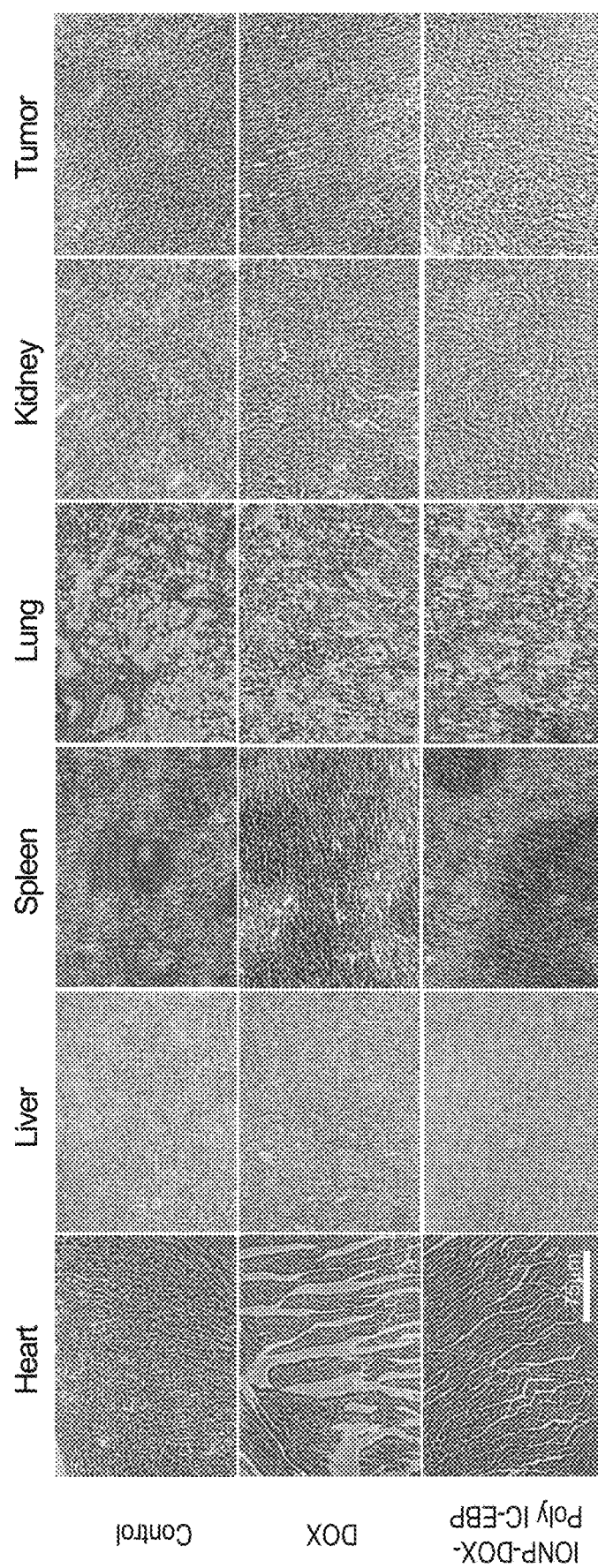

To assess systemic toxicity and DOX uptake in various organs and tumors, mice were treated with DOX or IONP-DOX-Poly IC-EBP. One week after mice were inoculated with cancer cells, a single intravenous injection of DOX or IONP-DOX-Poly IC-EBP (10 mg/kg DOX equivalent per mouse) was given to each mouse. Forty-eight hours post-injection, mice were sacrificed, and organs/tumors were collected and processed for H&E analysis. The H&E-stained images of heart tissue sections indicate that a severe heart damage was incurred in mice treated with DOX as evidenced by appearance of stripped spaces in myocardium, whereas minimal or no apparent heart damage was found in mice treated with IONP-DOX-Poly IC-EBP (FIG. 8B, first column). No pathological changes in organs other than heart were found in mice treated with either DOX or IONP-DOX-Poly IC-EBP. The cardiac toxicity of DOX has been well known, which is due to complex mechanisms. These results indicate that by loading DOX into the NP formulation, the cardiotoxicity of DOX may be reduced or eliminated.

Figure 9A:
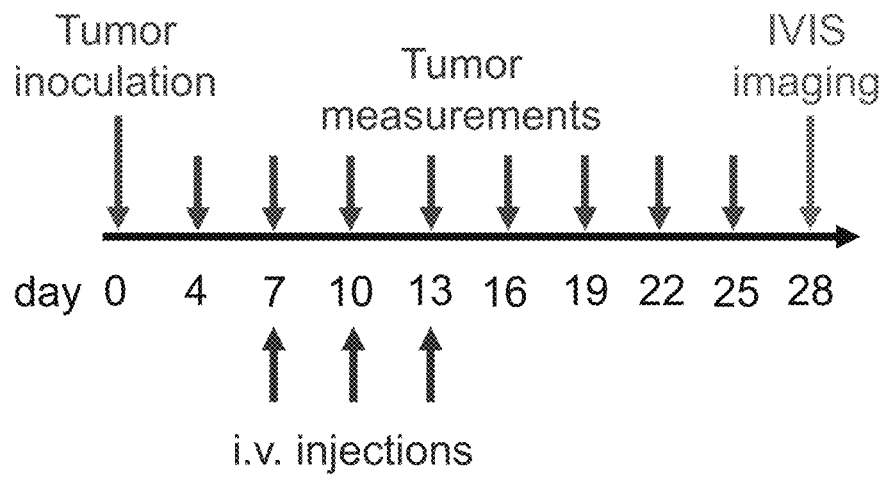
FIGS. 9A-9D show in vivo evaluation of NPs in a 4T1-luc flank tumor model of wild-type BALB/c mice.
Figure 9B:
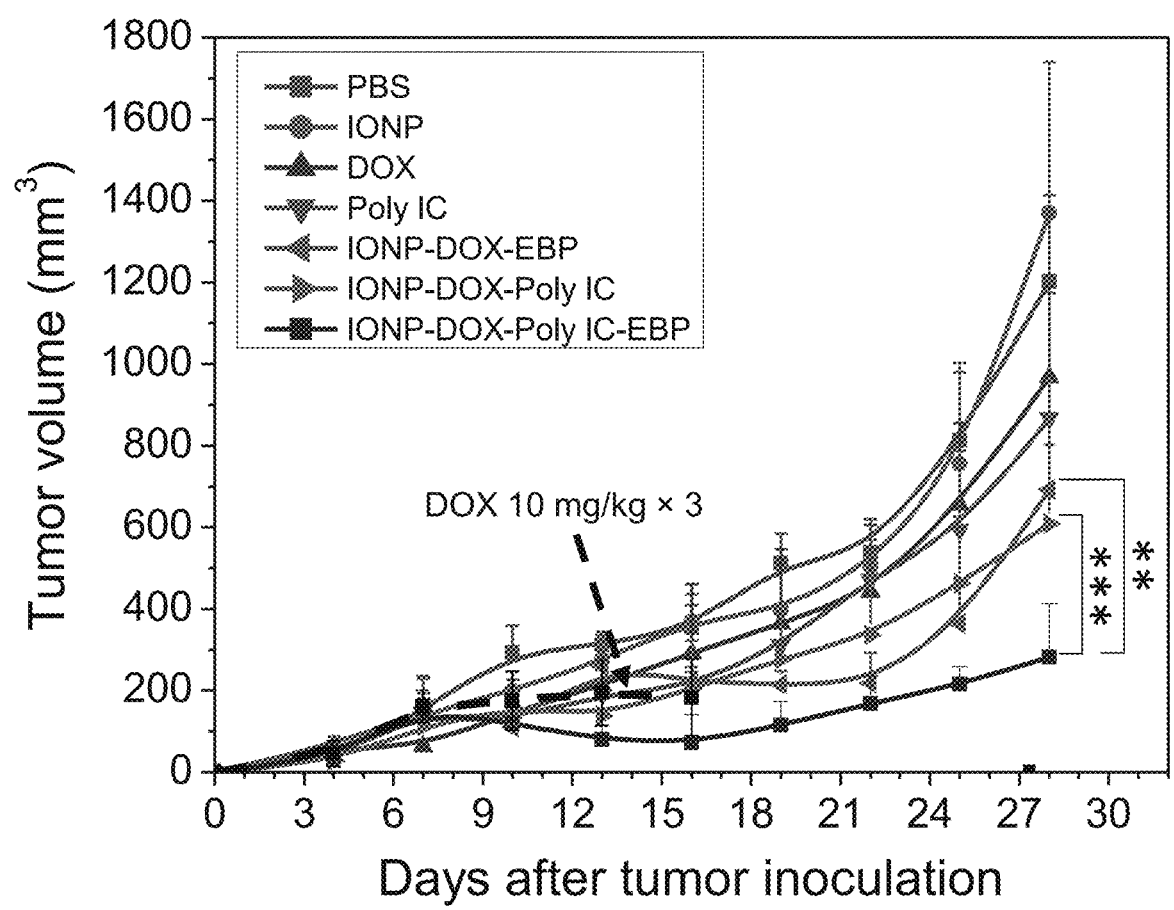
Figure 9C:
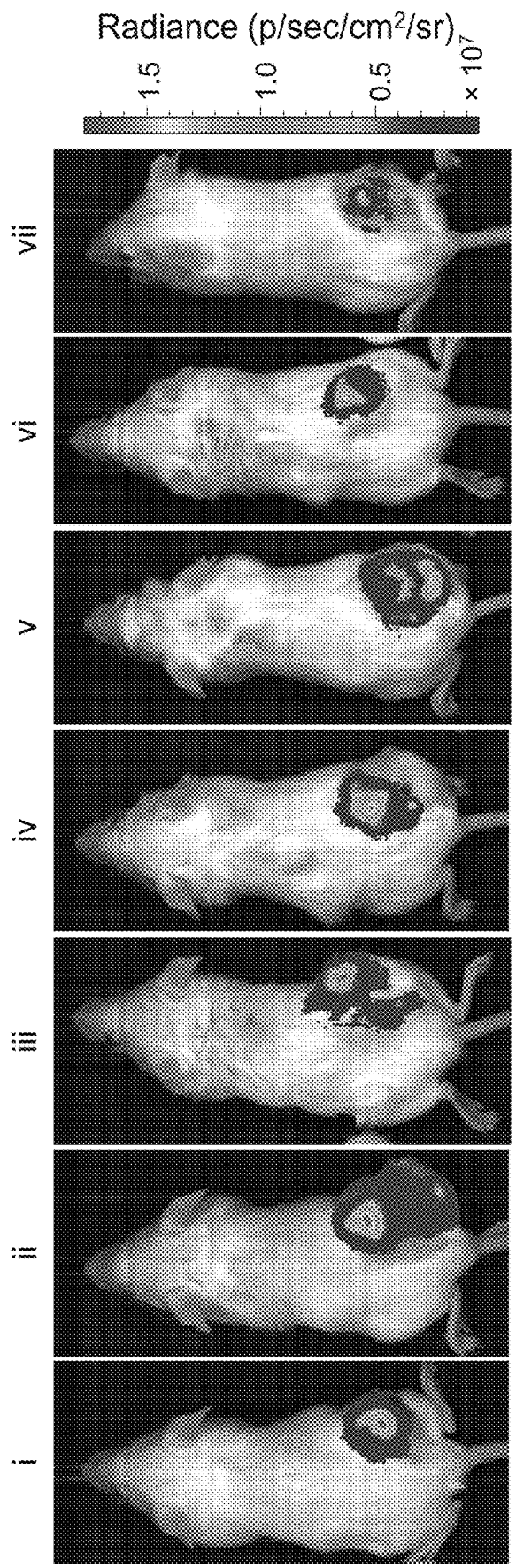
Figure 14A:
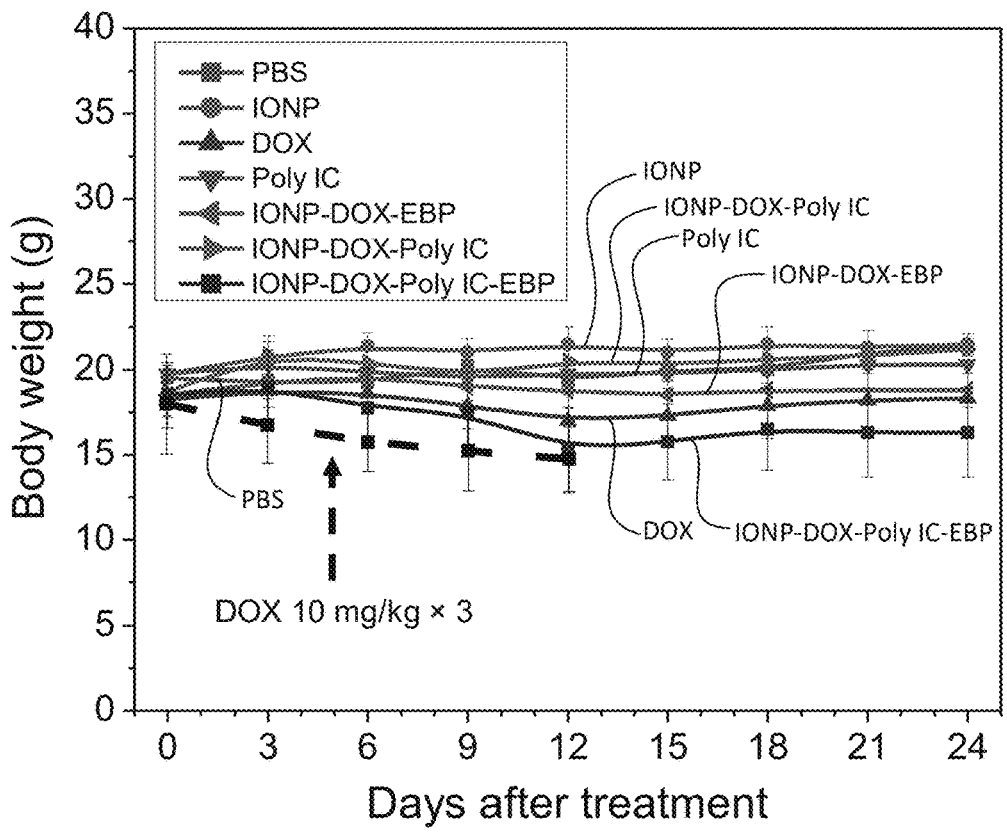
FIG. 14A compares body weights of mice from various treatment groups (n=4 per group). The agents administered were PBS, IONPs, DOX (5 mg/kg), Poly IC (18 mg/kg), IONP-DOX-EBP (DOX 10 mg/kg), IONP-DOX-Poly IC (DOX 10 mg/kg, Poly IC 18 mg/kg), and IONP-DOX-Poly IC-EBP (DOX 10 mg/kg, Poly IC 18 mg/kg). The dashed arrow curve indicates the treatment with free DOX (10 mg/kg; mice euthanized on day 12).
Figure 14B:
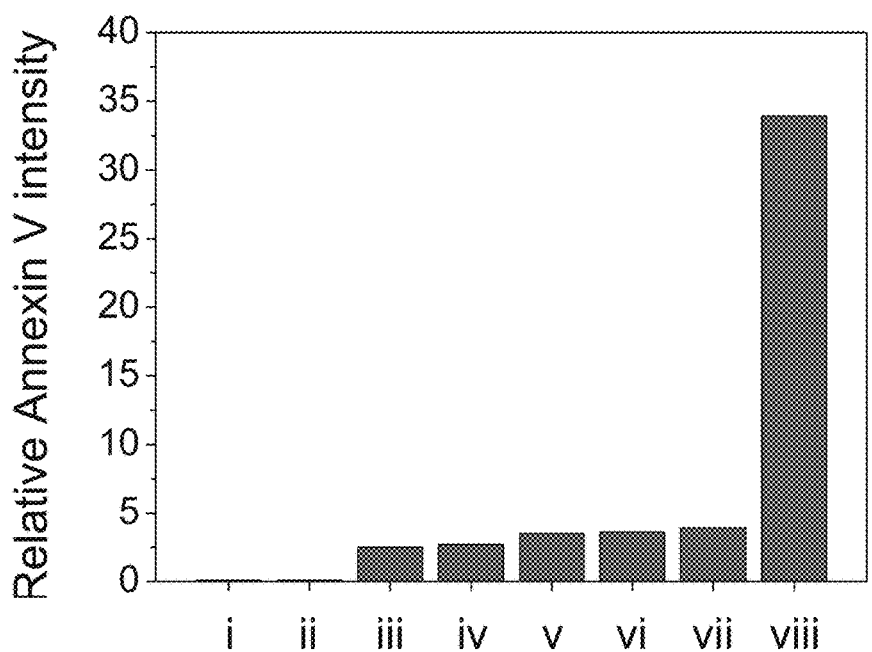
FIG. 14B shows apoptotic cells quantified from FIG. 8A. Annexin V intensity was calculated by ImageJ software. Treatment conditions: (i) PBS, (ii) IONPs, (iii) DOX 5 mg/kg, (iv) DOX 10 mg/kg, (v) Poly IC (18 mg/kg), (vi) IONP-DOX-EBP (DOX 10 mg/kg), (vii) IONP-DOX-Poly IC (DOX 10 mg/kg, Poly IC 18 mg/kg), and (viii) IONP-DOX-Poly IC-EBP (DOX 10 mg/kg, Poly IC 18 mg/kg).

Therapeutic Efficacy in Tumor Growth Inhibition and Inducing Apoptosis in Flank Tumor Model The luciferase-transfected 4T1 cells (4T1-luc) were inoculated into flanks of female wild-type BALB/c mice. This mouse model is appropriate for targeted chemo-immuno combinatorial therapy because it has an aggressive tumor proliferation profile and triple negative phenotypes. Particularly, the syngeneic mice have uncompromised immune systems which is ideal to test immuno-therapeutics. To evaluate the treatment efficacy, tumor growth in mice was monitored over time before and after treatment. Each group of mice were administered with one of following agents via I.V. injection: PBS, drug-free IONPs, DOX, Poly IC, IONP-DOX-EBP and IONP-DOX-Poly IC-EBP. The treatment started 7 days after tumor inoculation and three dosages were given in every three days: DOX, 10 mg/kg in NP formulations and free form, 3 d interval; Poly IC, 18 mg/kg, 3 d interval (FIG. 9A). It should be noted that we also used a lower dosage (5 mg/kg) for free DOX than the dosage for the NP formulations (10 mg/kg) because the severe toxicity incurred by free DOX at 10 mg/kg caused mouse death in less than 2 weeks (FIG. 14A). In contrast, mice administered with NPs at a dose of 10 mg/kg DOX survived with some weight loss, indicating an increased maximum tolerable dose (MTD) when DOX is incorporated into our NP formulation (FIG. 14B). FIG. 9B shows the average tumor volume measured over time for each mouse group with the treatment started at day 7 and completed at day 13 (3 doses). The tumor growth inhibition by a therapeutic agent is defined as the reduction in tumor volume when compared to the average tumor volume of the mouse group treated with PBS. Treating mice with bare IONPs, free DOX or free Poly IC showed no (e.g., IONPs) or small (e.g., free DOX, free Poly IC) inhibition to tumor growth as compared to PBS-treated mice (FIG. 9B). Comparatively, IONP-DOX-EBP and IONP-DOX-Poly IC showed substantial tumor inhibition. Significantly, IONP-DOX-Poly IC-EBP showed strongest tumor growth inhibition among all the treatment options (about 85%). FIG. 9C shows images of mice bearing 4T1-luc tumors 48 h after intravascular administration of various agents with IVIS. The bioluminescence generated from luciferase in cancer cells in mice was weakest in IONP-DOX-Poly IC-EBP treated ones among all treatments (FIG. 9C). This result showed its robust efficacy in a preclinical model due to the effects from targeted and combined chemo-immuno therapeutics.

Figure 9D:
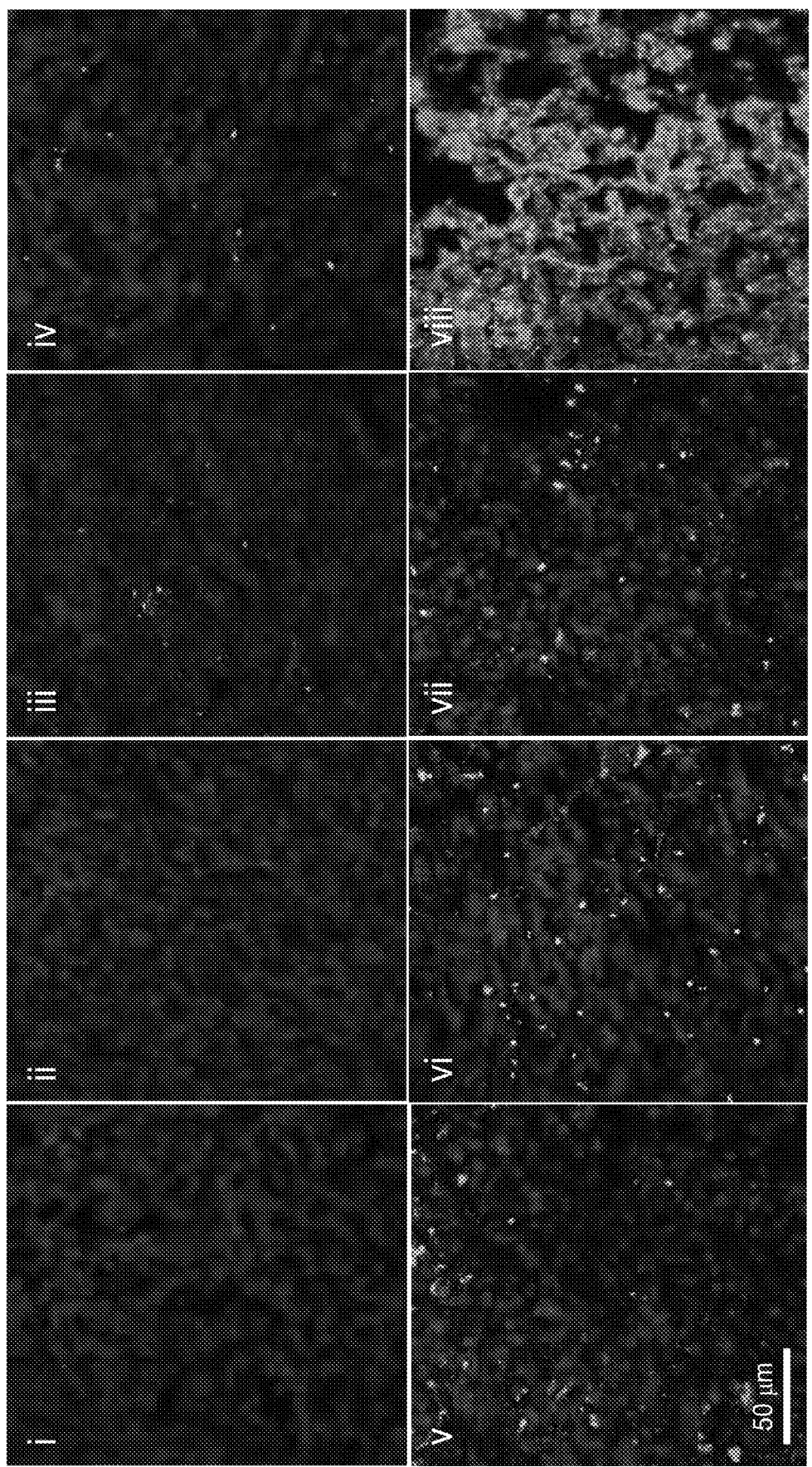

To investigate whether tumor cells underwent apoptosis in mice treated with various agents, each mouse was administered via I.V. injection with one of the following agents (i) PBS, (ii) IONPs, (iii) DOX 5 mg/kg, (iv) DOX 10 mg/kg, (v) Poly IC (18 mg/kg), (vi) IONP-DOX-EBP (DOX 10 mg/kg), (vii) IONP-DOX-Poly IC (DOX 10 mg/kg, Poly IC 18 mg/kg), and (viii) IONP-DOX-Poly IC-EBP (DOX 10 mg/kg, Poly IC 18 mg/kg). Tumor tissues were collected 48 h post injection and stained with Annexin V-Alexa Fluor 647 for apoptotic cells and propidium iodide (PI) for nucleic acids. Confocal microscopic images of these tumor sections showed that treatment of IONP-DOX-Poly IC-EBP induced massive apoptosis in tumor (FIG. 9D, viii). Tumors in mice that underwent other treatment options showed only minor apoptosis of various degrees (FIGS. 9B-9G and 14B). DOX induces DNA damage and apoptosis through inhibiting DNA topoisomerase II. Direct activation of TLR3 on breast cancer cells by Poly IC can also trigger apoptosis. Furthermore, the anti-tumor immunity induced by interaction between Poly IC and DCs can cause tumor death through apoptosis. Together, the multifunctional NP-mediated multiple attack to cancer cells, combined with targeted delivery, achieved the maximum tumor inhibition compared to any of the single-agent treatment options.

Inhibition of Tumor Growth and Metastasis in Orthotropic Tumor Model

Figure 10A:
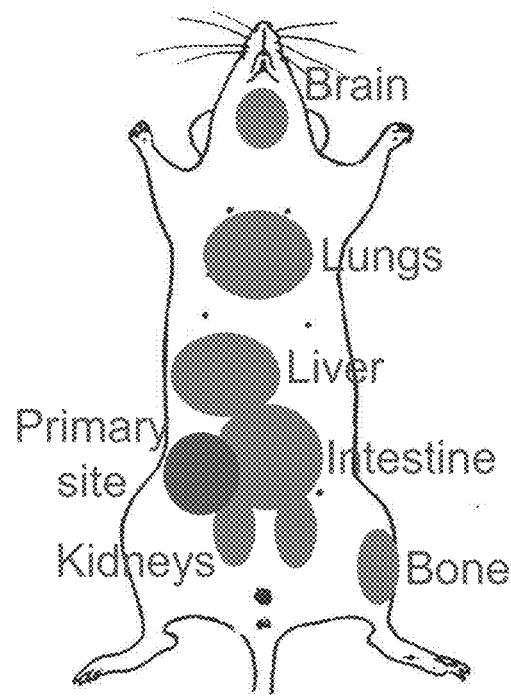
FIGS. 10A-10F show tumor growth and metastasis in a 4T1-luc primary tumor model.
Figure 10B:
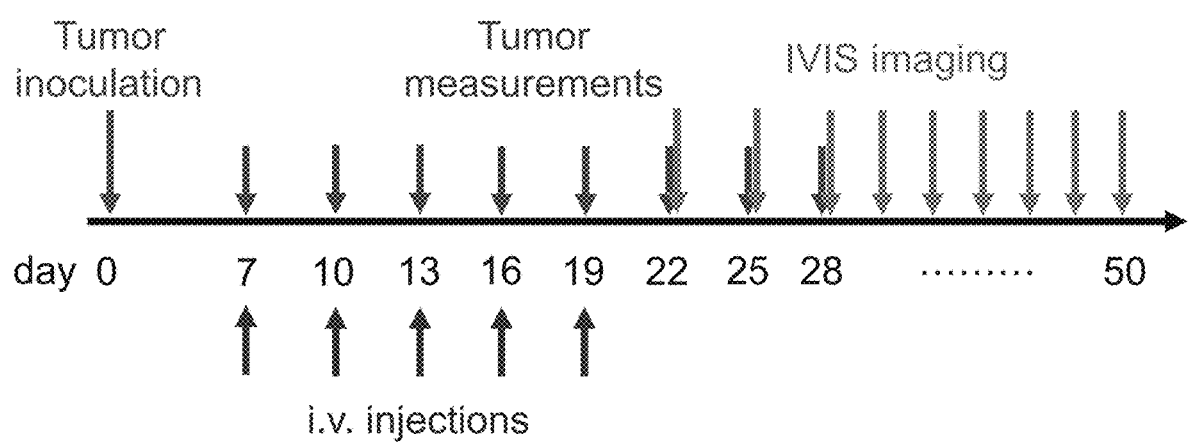
Figure 10C:
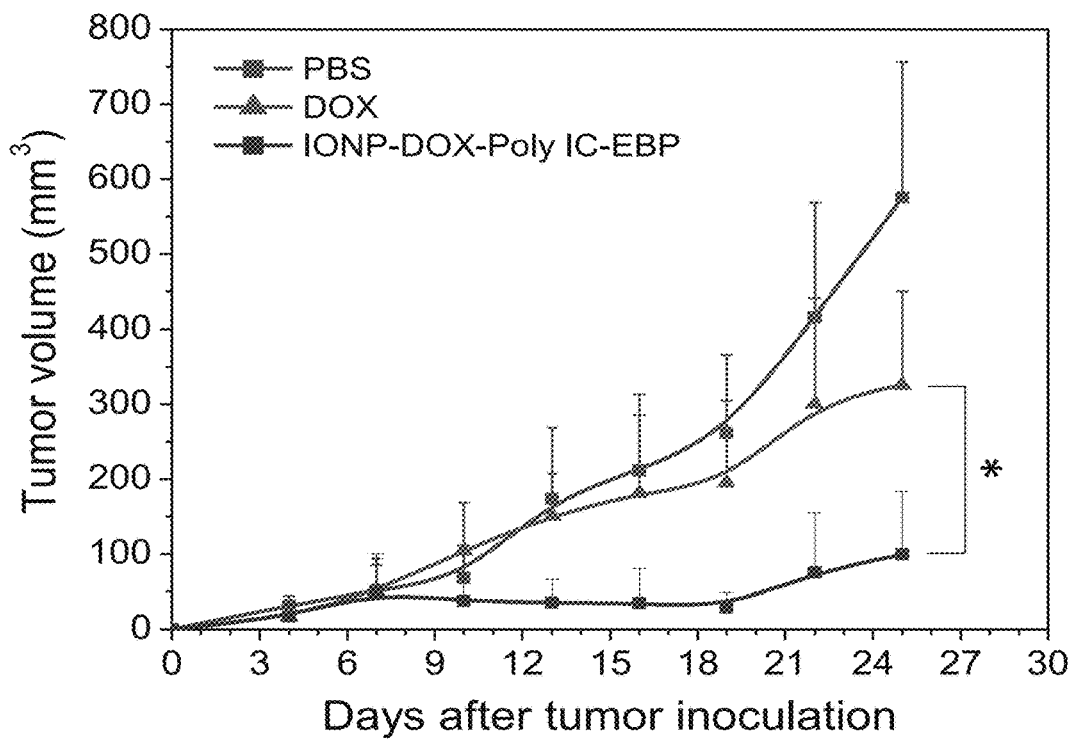
Figure 10D:
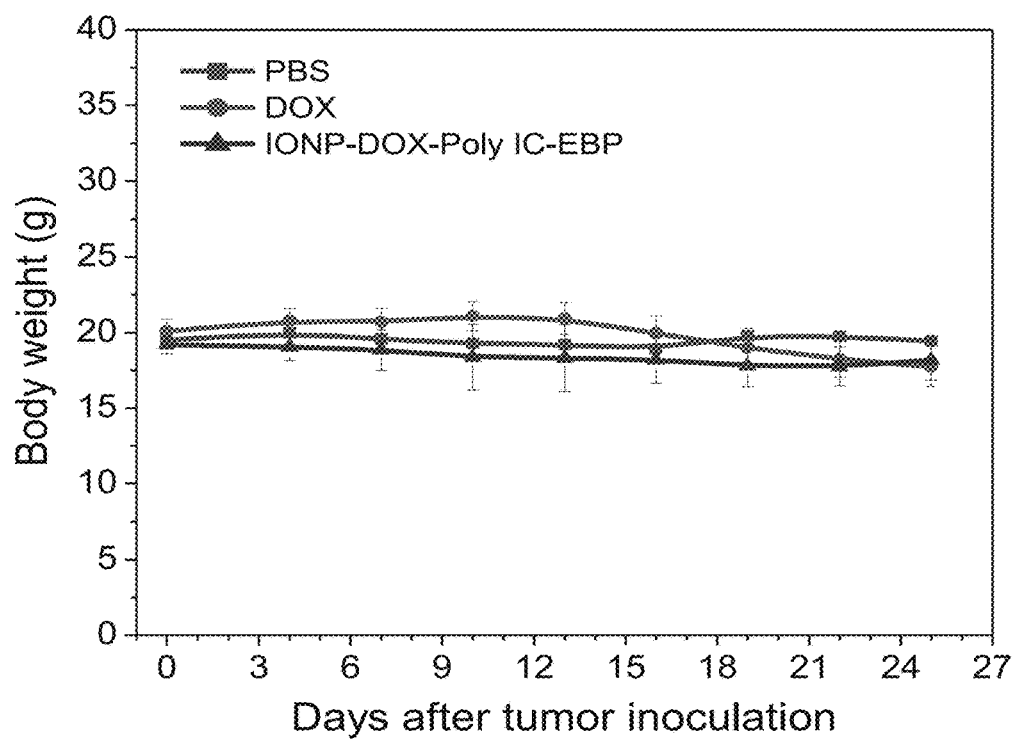
Figure 10E:
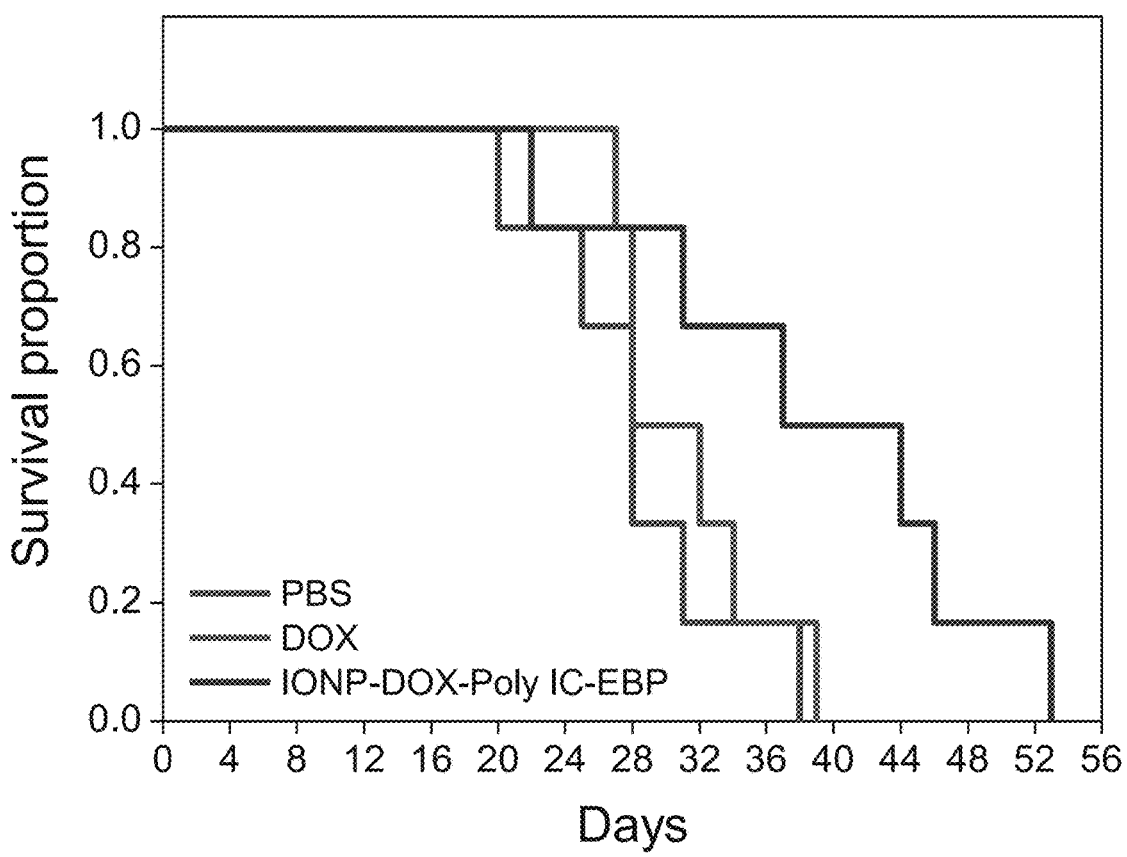
Figure 15:
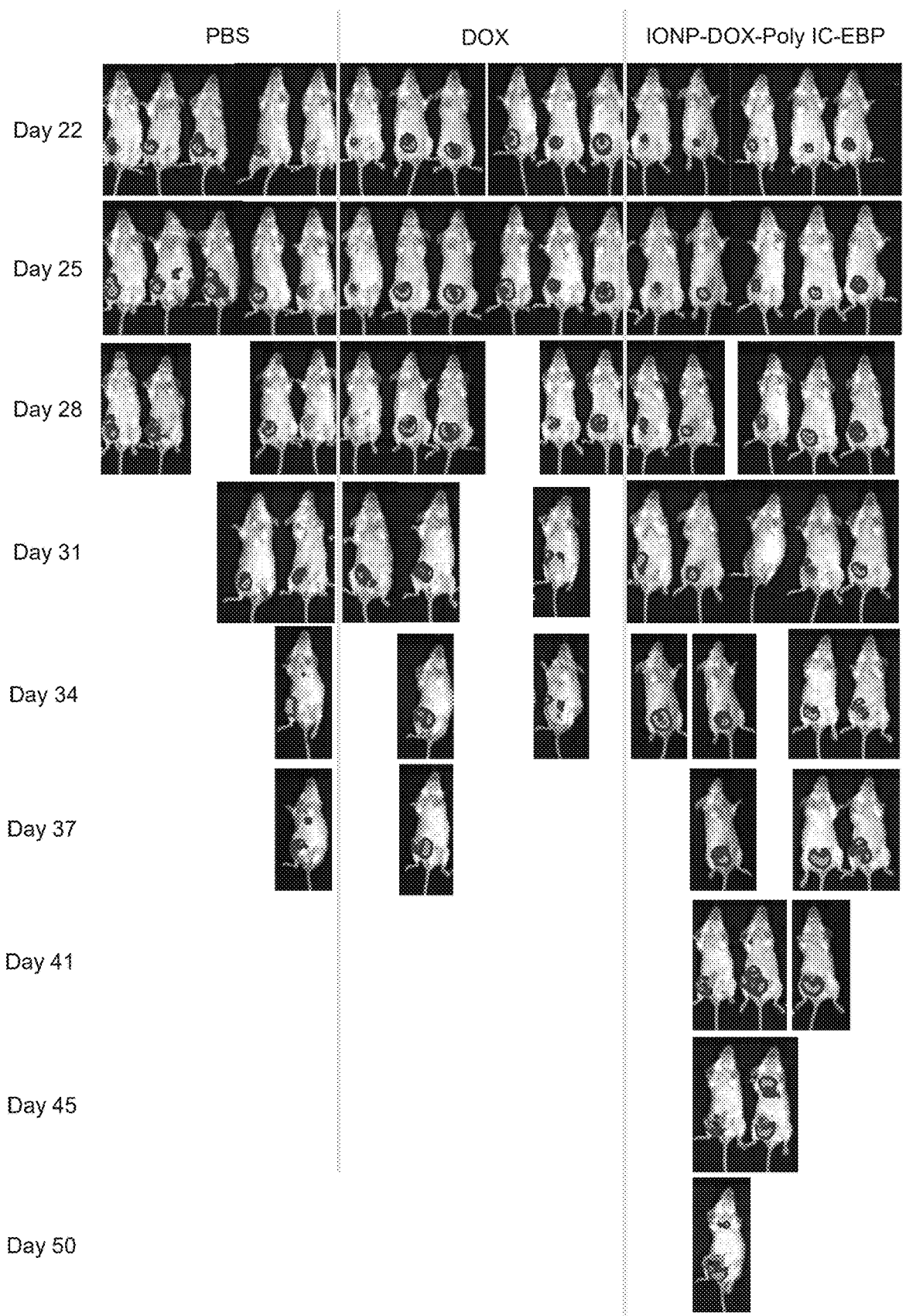
FIG. 15 shows metastasis of 4T1 tumors in mice treated with PBS, free DOX, or IONP-DOX-Poly IC-EBP and monitored by bioluminescence (IVIS Xenogen).

The therapeutic efficacy of IONP-DOX-Poly IC-EBP was evaluated in a second mouse model: a 4T1-luc orthotopic tumor model. Unlike in the flank tumor model where tumor cells were inoculated in the flank, 4T1-luc cells were directly implanted subcutaneously at mammary gland, the same anatomical site of breast cancer in human. Cancer cells grown in mammary gland have the tendency to metastasize to various organs (FIG. 10A). Thus, this model allows the examination of the capability of the NPs in inhibiting tumor metastasis in addition to tumor growth. Based on the investigation conducted in the flank tumor model above, two treatment options were selected for study in the second mouse model: free DOX 5 mg/kg and IONP-DOX-Poly IC-EBP (DOX 10 mg/kg, Poly IC 18 mg/kg), with each treatment including 5 instead of 3 sequential I.V. injections 3 days apart. Tumor volumes were measured over time using a caliper, and mice survival and tumor metastasis were monitored throughout the experiment (FIG. 10B). Treatment with IONP-DOX-Poly IC-EBP resulted in greater and more sustainable inhibition to tumor growth as shown by a flat growth curve lasting until 19 days (in contrast to 16 days with only 3 injections) (FIG. 10C). Tumor growth was monitored for 25 days. No treatment caused weight loss in mice during this period (FIG. 10D). Overall survival was continuously monitored till all mice were euthanized (FIG. 10E). The median survival times were 28.5, 32.5 and 37 d for PBS, free DOX, and IONP-DOX-Poly IC-EPB treated mice, respectively. Twenty-two days after tumor inoculation, metastasis was monitored by IVIS bioluminescence imaging. Un-treated mice showed metastasis as early as day 22 after tumor inoculation (FIG. 9F). Metastasis was found in liver (day 22), kidneys (day 22) and lungs (day 34) as shown by bioluminescence in PBS treated mice (FIG. 15). Free DOX treatment delayed the metastasis to day 31. Kidney metastasis was observed and marked with red arrow. IONP-DOX-Poly IC-EBP showed the potent treatment and delayed the metastasis to day 45 until lung metastasis was observed (FIG. 15).

Multifunctional Nanoparticle Performance and Uses

Chemotherapy has been shown to play a role in positive tumor immune response modulation by enhancing tumor antigenicity and adjuvanticity. Chemo-immuno-therapy could be a promising option in treating TNBC as shown by the recent approval of the combination of Atezolizumab (anti-PD-L1) with paclitaxel. However, those combinatorial therapies show improved efficacy only in a small subset patients. The promise of combined chemo- and immune-therapy for TNBC has been shadowed by the lack of an effective means to circumvent a number of obstacles including physiological and cellular barriers to the delivery of sufficient amounts of chemo- and immune-therapeutic agents to tumors.

The present disclosure provides a multifunctional nanoparticle: an EBP-conjugated and DOX/Poly IC co-loaded IONP for targeted delivery of chemo-immuno therapy for treating TNBC. The IONP-DOX-Poly IC-EBP is designed to circumvent common limitations of therapeutic agent delivery and endowed with many favorable attributes beyond those provided by existing carriers. The design has the following unique features: (1) a new assembly method to make a small and stable NPs by electrolyte-free layer-by-layer deposition, such method can be applied not only to DOX and Poly IC, but also to other charged therapeutic molecules in general; (2) a targeted, chemo-immuno combinatory therapy for metastatic TNBC, the targeting ligand enhances the delivery of both DOX and Poly IC on IONP into tumor microenvironments including tumor cells and immature DCs; and (3) superparamagnetic properties of IONPs render them detectable by MRI, thus enabling non-invasive tumor diagnosis and treatment response monitoring.

The targeting of triple negative breast cancer has been challenging due to the lack of cell surface receptors. Several cancer-specific cell surface targets were investigated such as PD-L1, CD44, CXCR4, uPAR, $\alpha_v\beta_3$ integrin, LIV-1, etc. Targeting these receptors has shown several limitations including (a) high dependence of cancer cell expression, (b) conjugation of antibodies which are bulky, showing side effects, and expensive, and (c) high systemic background of targets. Among several potential TNBC targets, endoglin is a co-receptor of transforming growth factor-beta and plays a crucial role in vasculature development and angiogenesis of breast cancer. Endoglin is involved in the proliferation and invasion of breast cancer cells, and high endoglin expression is correlated with a high risk for metastasis in patients. Monoclonal antibodies against endoglin have been used to target TNBC in mice models using NPs as a carrier and have shown a specific targeting effect. As described herein, the present disclosure utilizes an endoglin-specific small peptide that is much less bulky and allows for increased loading of therapeutic molecules. The NPs described herein are able to enter cancer cells effectively both in vitro (FIG. 4A) and in vivo (FIGS. 6A-6C).

Co-loading of both chemotherapeutics and immuno-therapeutics on a single NP had been technically challenging because of their diametrically different physicochemical properties that precluded co-loading. In previous studies, NPs have been employed to simultaneously deliver both chemo- and immuno-therapeutic antigens and/or adjuvants to tumors through active targeting or through enhanced permeability and retention effects. Most of these NPs were large in size (much greater than 100 nm), and as a result, experienced a short half-life in blood, which led to low drug accumulation in tumors. Although the alternative of loading immuno- and chemo-therapeutics on different NPs for separate delivery can avoid oversized NP, the fact that immuno- and chemo-drugs cannot reach the same cell at the same time could drastically impair their therapeutic synergy. On the contrary, the NP's LBL design described herein directly deposits positively charged DOX and negatively charged Poly IC on the surface of negatively charged ultra-small and stable PEG-coated IONP, eliminating the need for additional polyelectrolytes that could otherwise cause confounding immune responses for encapsulation and stabilization. Through modular surface engineering, the NP described herein exhibits efficient DOX/poly IC co-loading and tunable physicochemical properties including size and surface charge (FIGS. 2A-2F). The final NP bearing targeting peptide is spherical in shape and ultrasmall in size with a hydrodynamic diameter of about 53 nm. The NP demonstrates a long circulation time in blood (4.8 h) (FIG. 7B) and releases drug payload in an acidic environment and induces, concurrently, dendritic cell-mediated innate and T cell-mediated adaptive immune responses. The NP triggers DC maturation as confirmed by upregulation of BMDC surface markers (CD80 and CD86) (FIGS. 4D and 4E) without inflicting significant cytotoxicity on BMDCs, likely due to the insensitivity of DCs to DOX and the reduced drug uptake by the nucleus. It is reported that DCs in the 4T1 tumor microenvironment are functionally defective and exhibit a characteristic of immature phenotype, which is responsible for immunosuppression of 4T1. As a result of DC activation, both tumor and spleen generated antigen-specific immune response (FIG. 5C), and a higher level of production of IL-12 was observed by systemic injection of IONP-DOX-Poly IC-EBP as compared to injection of free Poly IC (FIG. 5B). Although several approaches had been introduced to deliver IL-12 gene to tumors, the delivery and transfection efficiency were limited and the gene carriers (e.g., PEI) showed severe toxicity to biological system. In tumor-bearing mice, the NP described herein effectively activates antigen-specific T cell response (CD8+, CD25+, CD69+) more than free Poly IC through systemic injections. This is likely due to the targeted delivery enabled by EBP and the small size of the NP described herein. Systemic injection of IONP-DOX-Poly IC-EBP resulted in the greatest tumor growth inhibition in the flank tumor model among all the treatment options (FIGS. 9A-9C). Further, the NP described herein is non-toxic to liver, spleen, lung and kidney (FIGS. 8A and 8B), and markedly reduced the cardiotoxicity of DOX and enabled the use of higher DOX dosing through targeted delivery to tumor sites (FIG. 9B).

Figure 10F:
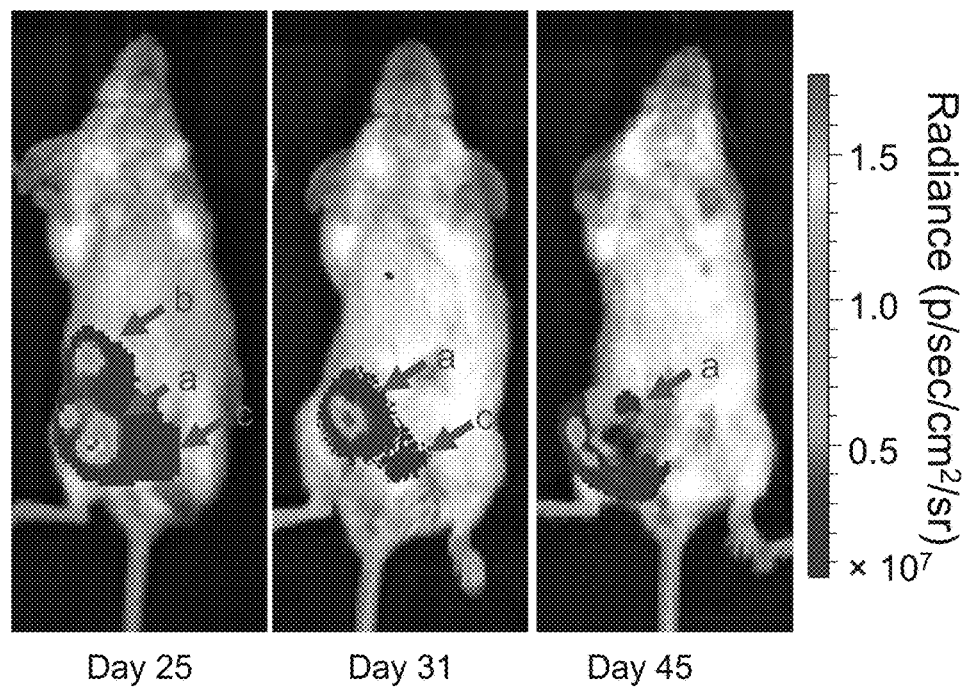
Figure 11A:
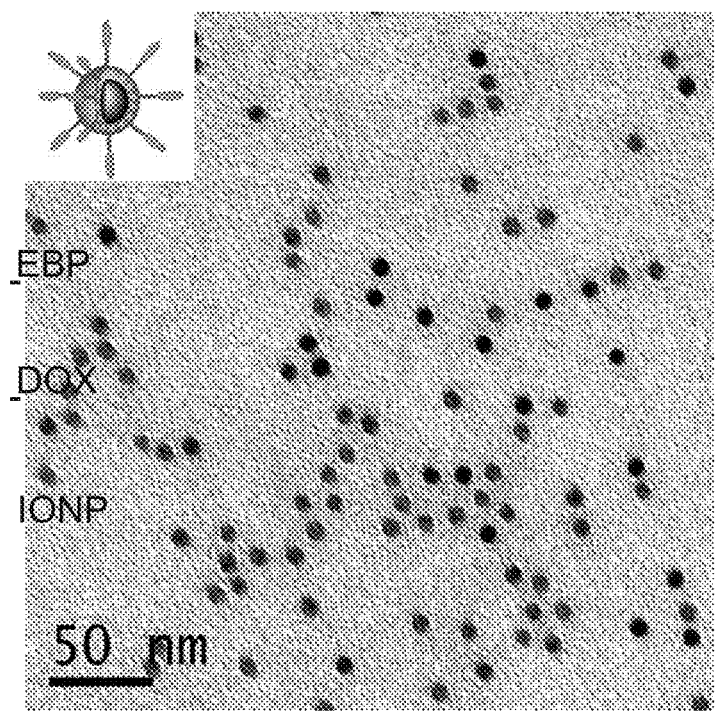
FIGS. 11A and 11B show TEM and AFM micrographs, respectively, of IONP-DOX-EBP (Fe/DOX ratio=10:16). Scale bars represent 50 nm.
Figure 11B:
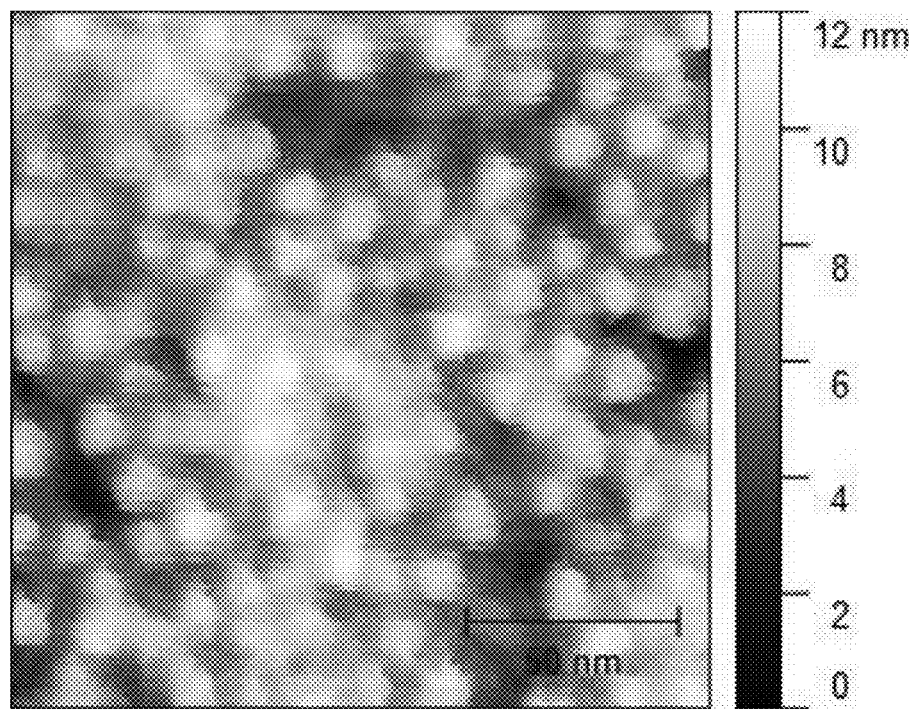
Figure 11C:
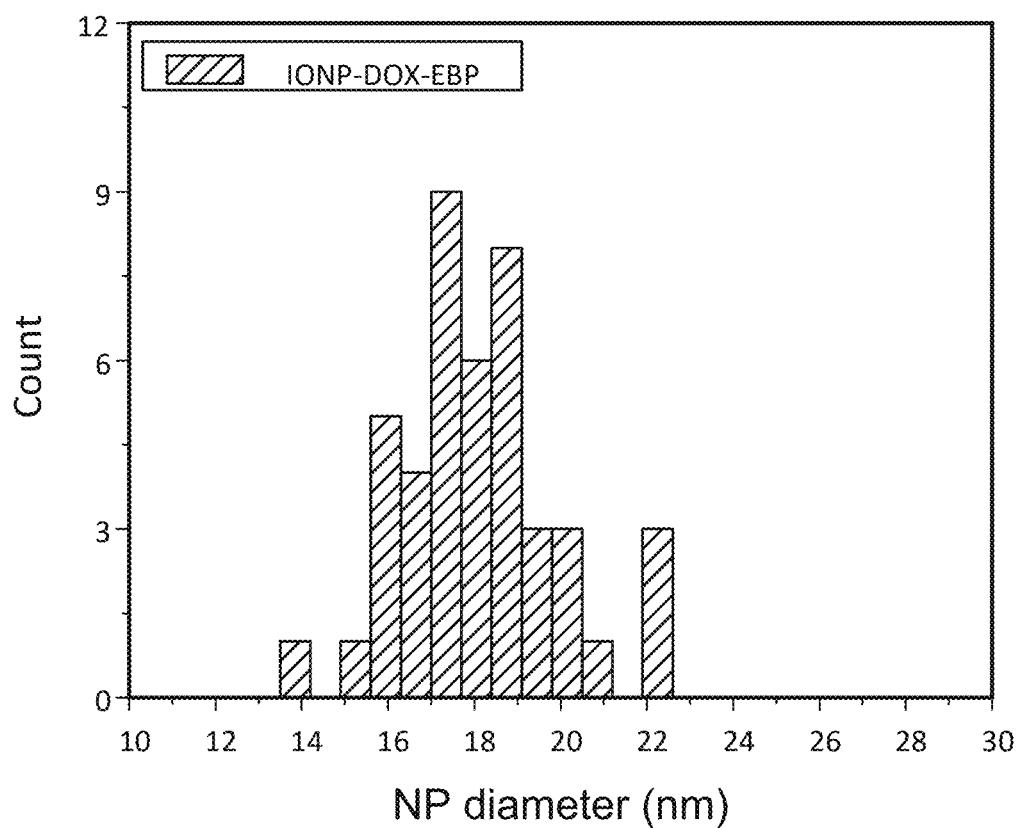
FIG. 11C shows histograms of diameters of IONP-DOX-EBP evaluated from AFM images.

The clinical potential of IONP-DOX-Poly IC-EBP was evaluated in the aggressive 4T1 breast cancer mouse model by systemic injection. 4T1 breast adenocarcinoma cells were used to mimic stage IV metastatic human breast cancer. 4T1 cells are highly aggressive and can spontaneously metastasize to various organs when injected into BALB/c mice. The 4T1 cells also have a "triple negative" phenotype (lack of ER, PR and HER2 receptors on cell surface) and are resistant to DOX treatment by expression of P-glycoprotein (efflux transporter of DOX). Various combinations of treatment options have been investigated to treat 4T1 tumors, including radio-immunotherapy, multi-agent chemotherapy, and multi-antibody therapy. But no effective treatment has been identified for the 4T1 induced breast metastasis. The NP described herein also demonstrated tumor targeting capability, and markedly increased the therapeutic efficacy against tumor growth and metastasis as compared to the treatment with DOX alone (FIGS. 10F and 15). In addition to the therapeutic function, the NP described herein provides MRI and optical imaging capability enabled by IONP core and near-IR fluorophore, respectively, allowing examination of NP localization in vivo (FIGS. 6A-6C).

The present disclosure provides a multifunctional NP formulation that can deliver chemo- and immuno-therapeutic agents simultaneously targeting breast cancer cells in a synchronous fashion. The NP demonstrates physicochemical properties favorable for in vivo application. The NP induces tumor apoptosis by multiple mechanisms including direct tumor cell killing, dendritic cell-mediated innate response and T cell-mediated adaptive immune response. The NP demonstrates a potent ability to inhibit tumor growth and metastasis, and to extend survival in an aggressive and metastatic mouse model of triple negative breast cancer (TNBC). The non-invasive image-guided approaches is useful in the clinic to enable monitoring of therapeutic response and improve the success rate of cancer treatment.

As used herein the term "about" refers to ±5% of the specified value.

EXPERIMENTAL DESCRIPTION

Materials and Methods

Materials 3-(Triethoxysilyl)propyl succinic anhydride (SATES) was purchased from Gelest (Arlington, VA). 2000 MW monoamine functionalized poly(ethylene) glycol (mPEG2K-$NH_2$) was purchased from Laysan Bio (Arab, AL). EBP was customized from GenScript (Piscataway, NJ). The 2-iminothiolane (Traut's reagent) was purchased from Molecular Biosciences (Boulder, CO). NHS-$PEG_{24}$-maleimide, Annexin V-Alexa Fluor 647 and Wheat germ agglutinin-Alexa Fluor 647 were purchased from Thermo Fisher Scientific (Rockford, IL). DOX was purchased from LC Laboratories (Woburn, MA). Annexin V-FITC was purchased from BD Biosciences (San Diego, CA). NHS-Cy5 was purchased from Lumiprobe Corp. (Hallandale Beach, FL). Anti-mouse antibodies CD86-Alexa Fluor 647 (GL-1) and CD80-PE (16-10A1) were purchased from BioLegend (San Diego, CA). The mouse IL-12 P40/70 ELISA kit was purchased from Raybiotech Inc. (Norcross, GA). D-Luciferin was purchased from PerkinElmer Inc. (Waltham, MA). All other chemical reagents were purchased from Sigma-Aldrich (St. Louis, MO).

NP Synthesis and Surface PEGylation

Oleic acid-stabilized iron oxide NPs with an 8-nm core were synthesized following the method described in Park, J., et al., *Nat Mater* (2004) 3 (12), 891. Coating these NPs with silane-PEG2000-$NH_2$ was adapted from the method described in Mu, Q., et al., *Journal of materials chemistry. B, Materials for biology and medicine* (2016) 4 (1), 32. For a typical batch, 50 mg of iron oxide NPs was suspended in 43 mL of anhydrous toluene followed by addition of 70 μL of triethylamine in a 3-neck round-bottom flask fitted with a Graham condenser. The flask was sealed with a rubber septum and purged with nitrogen. The solution was heated to 100° C. and 0.15 mL of SATES was added to the flask. 281.25 mg of mPEG2K-$NH_2$ was dissolved in 7 mL of anhydrous toluene and the resultant solution was added to the flask 15 minutes later. An additional 75 μL of SATES was injected 1 h after the mPEG2K-$NH_2$ injection, and the solution was allowed to react for an additional 6.75 h. The solution was transferred to a single-neck round-bottom flask and NPs were precipitated with hexane. The NP precipitate was dispersed in tetrahydrofuran (THF), sonicated for 10 min, and precipitated with hexane. The resulting NP pellet was suspended in 10 mL anhydrous THF and sonicated for 10 min. 93.75 mg of mPEG2K-$NH_2$ and 281.25 mg of mPEG2K-$NH_2$ were dissolved in 12 mL anhydrous THF and added to the NP solution. The flask was then sealed with a septum and purged with nitrogen. 18.75 mg of N, N'-dicyclohexylcarbodiimide (DCC) was dissolved in 2 mL anhydrous THF and added to the flask, and the reaction solution was placed in a sonication bath at 25° C. and allowed to react for 16 h. Fully PEGylated NPs were precipitated with hexane, redispersed in 20 mL of ethanol, sonicated for 10 min, and precipitated again with hexane. The pellet was fully dried and dispersed in deionized water under sonication for 10 min. The NPs were purified through size exclusion gel chromatography (Sephacryl S-200).

NP Conjugations

EBP (CAHKHVHHVPVRL) (SEQ ID NO: 1) was conjugated onto IONPs by NHS-PEG-maleimide crosslinking chemistry. The EBP has a cysteine modification at N-terminal to introduce a thiol group which is maleimide reactive. For conjugation of IONP with PEG, 1 mL of 3 mg of IONPs (the amount of NPs was determined by [Fe] concentration) in PBS buffer was first incubated with 2.13 μL of SM(PEG)$_{24}$ (250 mM in DMSO) for 30 min on a rocker. Free SM(PEG)$_{24}$ was removed by purification through a PD-10 desalting column (GE Healthcare, Piscataway, NJ) equilibrated with PBS. PEG-maleimide modified IONPs were then mixed with the EBP and allowed to react for 30 min, and unreacted EBP was removed using S-200 sephacryl resin equilibrated with PBS to obtain IONP-EBP. Fe concentration was determined by a ferrozine assay. To optimize DOX loading onto IONP-EBP, different Fe/DOX ratios (10:2 to 10:16, w/w) were tested. DOX (5 mg/mL in deionized water) and IONP-EBP were mixed in PBS and incubated overnight on a rocker. Unbound DOX was removed by passing samples through sephacryl S-200 columns to get IONP-DOX-EBP. Fe concentration was quantified by a ferrozine assay (Riemer, J., et al., *Anal Biochem* (2004) 331 (2), 370) and DOX concentrations were quantified by UV absorbance at 500 nm. Poly IC (10 mg/mL in deionized water) was then mixed with IONP-DOX-EBP with various ratios of Fe to Poly IC (10:2~10:16, w/w) and incubated for 20 min to make IONP-DOX-Poly IC-EBP. IONP-DOX-Poly IC-EBP was freshly made for all assays.

To make Cy5.5-labeled NPs, IONP-DOX-EBP (3 mg) was incubated for 1 h with NHS-Cy5.5 (7.2 μL, 5 mg/mL in DMSO) in PBS before purification by an S-200 sephacryl column in PBS. For NPs used in animal studies, the sample preparations were scaled up proportionally.

NP Characterizations

To prepare NP samples for TEM imaging, NP solution (4 μL) was transferred onto a TEM grid (copper grid, 300-mesh, coated with carbon and Formvar film). After drying the solution in air using a filter paper, TEM images were acquired on a Tecnai G2 F20 electron microscope (FEI, Hillsboro, OR) operating at a voltage of 200 kV.

The hydrodynamic size and ζ-potential of NPs were characterized using a Zetasizer Nano-ZS (Malvern Instruments, Worcestershire, UK). The analyses were performed at the room temperature. The pH value of all NP solutions for ζ-potential measurements was 7.4 (20 mM HEPES buffer).

Samples for AFM were prepared by dropping and drying a low concentration of NP solution on freshly cleaved mica. The samples were then imaged using a Bruker Dimension Icon AFM (Madison, WI, USA) in tapping mode in air, with an antimony-doped silicon cantilever (FESP, Bruker, Madison, WI, USA). This cantilever has a nominal spring constant of 2.8 N/m, a resonant frequency of 75 kHz, a length of 225 μm, and a tip radius of 8 nm. Resulting images were processed with Gwyddion software. The absorbance of different solutions was recorded by a UV-Vis spectrometer (Agilent Technologies, Santa Clara, CA). For agarose gel electrophoresis, free Poly IC and different NP-Poly IC mixtures were loaded onto a 0.8% agarose gel (premixed with ethidium bromide) and ran for 30 min at a voltage of 100 V. Gel was imaged by a Gel Doc XR imaging system (Bio-Rad).

pH-responsive DOX release was assessed by a dialysis method. IONP-DOX-Poly IC-EBP solution (PBS, pH 7.4) was loaded into three dialysis tubes (1 mL each, 14 kDa MW cutoff). Sealed dialysis tubes were then immersed in 30 mL of different buffers (PBS, pH 7.4; sodium acetate buffer, pH 5.4; MES buffer, pH 4.5) in a 37° C. water bath and stirred for 72 h. The DOX released was sampled (0.5 mL each) at different time points (1, 2, 4, 6, 8, 10, 24, 48 and 72 h) and quantified by fluorescence reading (SpectraMax i3 multimode microplate reader, Molecular Devices). Cumulative release was calculated through DOX concentration and converted to total percentage of drug released over time.

Cellular Studies in 4T1 Breast Cancer Cells

Cell culture. 4T1 and 4T1-luc cells were provided by Stanley Riddell laboratory in Fred Hutchinson Cancer Research Center. Cells were grown in RPMI-1640 medium supplemented with 10% fetal bovine serum and 1% antibiotic-antimycotic (Thermo Fisher Scientific, Rockford, IL). Cells were cultured in an incubator maintained at 37° C., 5% $CO_2$ and 95% humidity.

Characterization of cellular uptake by confocal laser scanning microscopy. 4T1 cells were seeded onto glass-bottom petri dishes (Mattech). After overnight incubation, cells were incubated with different agents (10 µg/mL DOX or DOX equivalent NPs) for 2 h at either 37° C. or 4° C. Cells were washed 3 times with cold PBS, fixed with 4% paraformaldehyde for 15 min at 37° C. and stained with 5 µg mL WGA-Alexa Fluor 647 for 5 min at 37° C., followed by 3 times of PBS washing (5 min each). Cells were then incubated with DAPI for 5 min at 37° C., followed by PBS washing. Cells were then mounted with VECTASHIELD mounting medium (Vector Laboratories, Inc. Burlingame, CA). The images of cells were acquired using a Leica SP8X confocal laser scanning microscope (Leica, Germany).

Cell uptake assay by flow cytometry. 4T1 cells were incubated with different agents for 2 h (10 µg/mL DOX or DOX equivalent NPs) at either 37° C. or 4° C., followed by washing with cold PBS for 3 times. Cells were then trypsinized and resuspended in cold PBS and analyzed by flow cytometry (FACSCanto II, BD Biosciences). Each condition was triplicated.

Alamar Blue cell viability assay. Cells were seeded in a 96-well plate and incubated overnight. The following day, the medium was replaced with medium containing various agents. The cells were then incubated for 72 h. Cell viability was assessed using the Alamar Blue assay. Briefly, the medium was replaced with cell culture medium containing the reagent and allowed to incubate for 2 h. Following the incubation, a microplate reader (SpectraMax i3 multimode microplate reader, Molecular Devices) was used to determine the fluorescence intensity of the dye (550ex/590em). The fluorescence intensity from NP or free drug treated cells was compared to those from untreated control cells to determine percent viability. Each condition was triplicated.

Cell apoptosis assay by flow cytometry. 4T1 cells were seeded into 6-well plates and incubated overnight. DOX or DOX-equivalent NPs were added into cells (1 µg/mL DOX final concentration). Cells were incubated with NPs for 48 h. Cells were then trypsinized, aspirated, and washed once with PBS. Cells were then counted and suspended in 0.1 mL Annexin V binding buffer containing 50 µg/mL propidium iodide and 5 µL FITC-Annexin V reagent. Cells were further incubated for 15 min at room temperature in dark. 0.4 mL Annexin V binding buffer was added prior to analysis by flow cytometry. Data acquisition was performed on FACSCanto II and analyzed by FlowJo software (Treestar, Inc., San Carlos, CA). Each condition was triplicated.

Cellular Studies of Bone Marrow-Derived Dendritic Cells (BMDCs)

BMDCs preparation. BMDC were generated from female BALB/c mice of 6-8 weeks old. The isolation of bone marrow cells was carried out following the method described in Madaan, A., et al., *Journal of Biological Methods* (2014) 1 (1). Cells were resuspended in RPMI-1640 supplemented with 10% FBS, 20 ng/mL recombinant murine GM-CSF (Shenandoah Biotechnology, Inc, Warwick, PA), and antibiotics (Pen Strep). Cells were allowed to differentiate for 7 d with one addition of fresh media at day 3. At day 7, cells were aspirated and counted for assays. Medium containing 10 ng/mL GM-CSF was used in assays.

Confocal microscopic imaging of cellular uptake. Cells were seeded onto a chamber slide (Nunc™ Lab-Tek™ II Chamber Slide™ System, Thermo Fisher Scientific Rockford, IL) with a density of 50,000 per well and incubated overnight. DOX, IONP-DOX-EBP-Cy5, or IONP-DOX-Poly IC-EBP-Cy5 was added into cells at a concentration of 10 µg/mL Poly IC-equivalency and incubated for 1 h. Cells were then washed and imaged with a Leica SP8X confocal laser scanning microscope.

BMDCs maturation. Cells were seeded onto a 6-well plate at a density of 300,000 per well and incubated overnight. Poly IC, IONP-DOX-EBP or IONP-DOX-Poly IC-EBP was added into cells at a concentration of 10 µg/mL Poly IC-equivalency and incubated for 24 h. Cells only in medium were used as control. Cells were then trypsinized, aspirated and co-stained with CD80-PE and CD86-AF647 according to manufacturer's instruction. Cells were then analyzed by flow cytometry on FACSCanto II. All experiments were performed in triplication.

BMDC viability. Cells were seeded onto a 96-well plate at a density of 30,000 per well and incubated overnight. Poly IC, IONP-DOX-EBP or IONP-DOX-Poly IC-EBP was incubated with cells at a concentration of 10 µg/mL Poly IC-equivalency for 24 h. Cells only in medium were used as control. Cell viability was then assessed by aforementioned Alamar blue assay. Each condition was triplicated.

IL-12 production by ELISA assay. All conditions used were same as those for viability assay. Twenty-four hours after addition of agents into cell medium, supernatants were collected and IL-12 levels in medium were assessed by an ELISA assay kit following the manufacturer's protocol. Each condition was triplicated.

Animal Studies

All animal studies were conducted in accordance with University of Washington Institute of Animal Care and Use Committee (IACUC) approved protocols as well as with federal guidelines. Five-week-old female BALB/c mice were purchased from The Jackson Laboratory (Bar Harbor, ME) and housed in the animal research facility.

Pharmacokinetics of IONP-DOX-Poly IC-EBP-Cy5

Six-week-old mice were administered with IONP-DOX-Poly IC-EBP-Cy5 through I.V. injection (dosage: 10 mg/kg DOX or equivalent). At 1, 2, 4, 8, 24 and 72 h post-injection, blood (5-25 µL) was collected from tail vein. The total amount of blood withdrawn from each mouse never exceeded one percent of the total body weight of the animal during the experiment. Whole blood was diluted with PBS and spun using a benchtop centrifuge for 2 min at 5000 g to separate the plasma. The diluted plasma was added to a 96-well black plate. The plate was scanned on a SpectraMax i3 plate reader (fluorescence mode) to measure Cy5 (ex, 646 nm; em, 676 nm) and DOX (ex, 500 nm; em, 600 nm) fluorescence signals. Three mice were used for each group.

Serum IL-12 Determination

The same conditions in pharmacokinetics study were used here except that blood was collected before agent administration and 2, 6.5 and 24 h after administration. IL-12 in plasma was assessed using an ELISA kit following the manufacturer's instruction and quantified with a SpectraMax i3 plate reader.

Antigen-Specific T Cell Response by Flow Cytometry

Twelve 6-week-old female BALB/c mice were used. 4T1 cells ($10^5$ cells per mouse) were inoculated subcutaneously into #9 mammary glands. The tumors were allowed to grow into palpable masses. Ten days after tumor inoculation, the 12 mice were separated into 4 treatment groups. Four treatments, including IONP-DOX-EBP-Poly IC (10 mg/kg DOX and Poly IC), IONP-DOX-EBP (10 mg/kg DOX), free Poly IC (10 mg/kg Poly IC) and PBS, were administered intravenously into four groups of mice bearing tumors (200 µL per mouse), respectively. Three days after administration, mice were euthanized, and tumors and spleens were harvested.

Harvested tumors and spleens were then sectioned, squeezed through 70 µm cell strainers and washed with PBS w/1% v/v ratio of FBS to obtain single cell suspensions. Cells were spun down with a centrifuge at 1500 rpm for 4 min and resuspended in 750 µL PBS w/1% v/v FBS. Anti-CD8-PE, anti-CD25-APC, and anti-CD69-FITC (Biolegend Inc.) solutions (3 µL each) were then mixed with 241 µL of PBS w/1% v/v FBS (total antibody solution volume for each single cell suspension was 250 µL). The cell/antibody suspension was then incubated in dark at room temperature for 30 mins. After incubation, 11 mL of PBS w/1% v/v FBS was added to all cell/antibody suspensions followed by centrifuging at 1500 rpm for 4 mins. Finally, all cell pellets were resuspended in 500 µL PBS w/1% v/v FBS and analyzed by flow cytometry (FACSCanto II).

Near-IR Fluorescence and Bioluminescence Imaging

Accumulation of IONP-DOX-Poly IC-EBP-Cy5.5 in tumor was assessed by near-IR fluorescence imaging. One week after tumor inoculation, IONP-DOX-Poly IC-EBP-Cy5.5 was administered into mice through I.V. injection. At 0.5 h, 6 h, 1 d, 2 d, 4 d and 7 d post-injection, fluorescence and/or bioluminescence images, as well as optical photographs, were taken by a XENOGEN IVIS 200 imaging system (PerkinElmer Inc.) with imaging parameters: excitation wavelength: 710 nm; emission filter: ICG; exposure time: 1 second; binning factor: 2; f/stop: 4. For bioluminescence imaging of tumors, mice were injected with 150 mg $kg^{-1}$ luciferin intraperitoneally at day 24 after first administrations and imaged with an IVIS system. Imaging parameters are emission filter: open; exposure time: 30 seconds; binning factor: 2; f/stop: 4.

Tumor Growth Inhibition Study in 4T1-luc Flank Tumor Model

6-Week-old female BALB/c mice were used. 4T1-luc cells were transfected to stably express luciferase so that bioluminescence imaging could be used to monitor tumor growth. 4T1-luc cells were trypsinized and suspended in PBS ($10^7$ cells/mL) and injected subcutaneously into the right flanks of mice (0.1 mL per mouse). Seven days after tumor inoculation, twenty-eight mice were randomly divided into 7 groups and each group was administered through intravenous injection with three doses of one of the following agents: PBS, IONPs, DOX, Poly IC, IONP-DOX-EBP, IONP-DOX-Poly IC, and IONP-DOX-Poly IC-EBP. For free DOX injection, the dose was 5 mg/kg. For all NP agents, doses of DOX and Poly IC were 10 mg/kg and 18 mg/kg, respectively. Each mouse received an injection at day 7, 10 and 13 after tumor inoculation. The tumor size was measured by a caliper and the tumor volume was calculated by equation: $V = width^2 \times length/2$. The tumor size was measured every 3 days starting at day 4 after tumor cell inoculation. The body weight was also monitored after first agent administration.

Tumor Growth Inhibition, Survival and Metastasis Study in 4T1-luc Primary Tumor Model 6-Week-old female BALB/c mice were used in this study. 4T1-luc cells were injected subcutaneously into the #9 mammary glands ($10^6$ cells in 0.05 mL PBS per mouse). Seven days after tumor inoculation, eighteen mice were randomly divided into 3 groups and each group was administered through intravenous injection with five doses of one of the following agents: PBS, DOX, and IONP-DOX-Poly IC-EBP. For free DOX, dose was 5 mg/kg per injection. For IONP-DOX-Poly IC-EBP, doses of DOX and Poly IC were 10 mg/kg and 18 mg/kg, respectively. Each mouse received an injection at day 7, 10, 13, 16 and 19 after tumor inoculation. The tumor size and body weight were monitored after first administration. Metastasis was monitored by IVIS imaging starting at day 22 after tumor inoculation. Mice were imaged at day 22, 25, 28, 31, 34, 37, 41, 45 and 50. Mice were euthanized following the approved animal protocol.

Processing and Imaging of Sectioned Organs and Tumors

One week after inoculated with 4T1-luc cells, mice were injected with various agents intravenously. Forty-eight hours later, mice were euthanized and organs (heart, kidney, liver, lung, and spleen) and tumors were harvested and pre-served in 10% formalin for 48 h. Formalin-fixed tissue samples were first transferred from PBS to 70% ethanol and maintained for 2 hours, and then were transferred into 95% ethanol/5% methanol and maintained for an additional 2 hours. The samples were transferred in absolute ethanol and maintained for 1 hour, and then transferred again into 3 consecutive absolute xylene solutions and maintained in each for 1 hour. The samples were dehydrated and then placed in 2 consecutive melted paraffin baths and maintained in each for 2 hours. The tissue samples were then embedded in paraffin blocks and sectioned at 10 um thickness and loaded onto microscope slides. The loaded slides were heated to remove excess paraffin and adhere the samples to the slides. The samples were then deparaffinized by a series of xylene, ethanol and PBS baths.

Tumor Apoptosis Test by Annexin-V and Confocal Microscopic Imaging

The deparaffinized tissue samples from the above process were stained with PI and Annexin V-Alexa Fluor 647, mounted with Prolong Gold mounting medium, and imaged with a Leica SP8X confocal microscope. Annexin V stained cells are apoptotic.

H&E Staining and Imaging for Histopathology

The deparaffinized samples were stained with haemotoxylin and eosin, and mounted with Prolong Gold mounting medium. Microscopic images of tissues were acquired using a Nikon ECLIPSE TE 2000-S microscope.

DOX Uptake in Organs and Tumors by Confocal Microscopic Imaging

The deparaffinized tissue samples were stained with DAPI and WGA-AF647 and mounted with Prolong Gold mounting medium. Samples were imaged with a Leica SP8X confocal microscope.

MR Imaging

In vitro MR imaging. Magnetic properties of IONP-DOX-Poly IC-EBP were assessed using MR Imaging. Quantitative $T_2$ and $T_2$-weighted scan sequences were used to determine $R_2$ relaxivity values and $T_2$-weighted signal changes as a function of Fe concentration, respectively. MR imaging was performed using a Bruker Avance III 600 MHz 14 T vertical-bore spectrometer. NPs in phosphate buffered saline were pipetted into glass vials (3.25 mm I.D., 5 mm O.D., 200 µL volume). The vials were fixed in place inside a water reservoir; the water served as a homogeneous background signal to minimize magnetic susceptibility variations near the samples. The secured vials were placed in a 25-mm single-channel $^1$H radiofrequency receive coil (PB Micro 2.5). Relaxation properties of NPs were evaluated with a quantitative $T_2$ multi-spin multi-echo (MSME) pulse sequence with TR=2500 ms, TE=6.7+6n ms (n=0-16), and 78×156 µm$^2$ in-plane resolution with 0.5 mm slice thickness for 14 slices. $T_2$-weighted images were acquired with a rapid acquisition with refocused echoes (RARE) pulse sequence with TR=4000 ms, TE=6.78 ms, and 78×52 µm$^2$ in-plane resolution with 0.5 mm slice thickness for 14 slices. Analysis of MRI data was accomplished with the FMRIB software library (FSL), Paravision 5.1 analysis package (Bruker), and ImageJ (NIH). $T_2$ values were determined within a circular, 100-voxel region of interest.

In vivo MR imaging. In vivo MR imaging was performed using the same imaging system used for in vitro MR imaging. A $T_2$-weighted scan sequence was used to acquire MR images prior to and following tail-vein injection of IONP-DOX-Poly IC-EBP. A mouse was anesthetized with isoflurane (Piramal Healthcare) and attached to a coil-integrated respiratory monitoring system (SA Instruments; MR-compatible small animal monitoring and gating system) with nose-cone for oxygen/anesthetic, ear-bar head holder, circulating temperature control bath, and residual gas extraction. Abdominal scans were acquired using a RARE $T_2$-weighted scan sequence (TR=4000 ms, TE=27 ms, in-plane resolution=62×94 µm2, matrix=384×256) with slices oriented in the transverse plane with 0.5 mm slice thickness and 0.75 mm interslice. Analysis of in vivo MR images was performed using the Paravision 5.1 analysis package (Bruker) and ImageJ (NIH).

Statistical Analysis

Student's unpaired t-tests were performed for comparison between treatment groups. One-way and two-way analyses of variance (ANOVA) followed by Turkey's post-hoc multiple comparison tests were used for comparison of multiple groups. Statistical analyses were performed in Microsoft Excel or GraphPad Prism software.

While illustrative embodiments have been illustrated and described, it will be appreciated that various changes can be made therein without departing from the spirit and scope of the invention.

The embodiments of the invention in which an exclusive property or privilege is claimed are defined as follows:

1. A nanoparticle for targeted therapeutic drug delivery, comprising:
   (a) an iron oxide core having silica-polyethylene glycol coupled thereto to provide an iron oxide coated core;
   (b) a cytotoxic agent reversibly associated with the coated core;
   (c) an immunomodulating agent reversibly associated with the coated core; and
   (d) a tumor targeting agent associated with the coated core, wherein the nanoparticle has a dehydrated diameter in a range of about 18 nm to about 28 nm, and wherein the nanoparticle has an average hydrodynamic diameter in a range of about 50 nm to about 80 nm.

2. The nanoparticle of claim 1, wherein the cytotoxic agent forms a first layer surrounding the coated core.

3. The nanoparticle of claim 1, wherein the immunomodulating agent forms a second layer surrounding the first layer.

4. The nanoparticle of claim 1, wherein the cytotoxic agent is a chemotherapeutic drug.

5. The nanoparticle of claim 1, wherein the cytotoxic agent is selected from the group consisting of doxorubicin, daunorubicin, epirubicin, idarubicin, irinotecan, topotecan, mitoxantrone, vinblastine, cisplatin, and mixtures thereof.

6. The nanoparticle of claim 1, wherein the immunomodulating agent is an agonist of a receptor in innate or adaptive immune response.

7. The nanoparticle of claim 1, wherein the immunomodulating agent is polyinosinic: polycytidylic acid (PolyIC).

8. The nanoparticle of claim 1, wherein the tumor targeting agent is a tumor target ligand or peptide against triple negative breast cancer, a tumor target ligand against tumor vasculature endothelia cells, a tumor target ligand folic acid against folate receptor, or a transferrin against transferrin receptors overexpressed by breast cancer.

9. The nanoparticle of claim 1, wherein the cytotoxic agent is doxorubicin, the immunomodulating agent is polyinosinic: polycytidylic acid (PolyIC), and the tumor targeting agent is endoglin-binding peptide (EBP).

10. A pharmaceutical composition comprising the nanoparticle of claim 1 and a pharmaceutically acceptable carrier.

11. A method for treating breast cancer, comprising administering a therapeutically effective amount of a nanoparticle of claim 1 to a subject in need thereof.

12. The method of claim 11, wherein the breast cancer is metastatic breast cancer.

13. The method of claim 11, wherein the breast cancer is triple negative breast cancer (TNBC).

14. The method of claim 11, wherein administering a therapeutically effective amount of the nanoparticle results in direct tumor cell killing.

15. The method of claim 11, wherein administering a therapeutically effective amount of the nanoparticle results in dendritic cell-initiated innate immune response.

16. The method of claim 11, wherein administering a therapeutically effective amount of the nanoparticle results in T cell-mediated adaptive immune response.

17. The method of claim 11, wherein administering a therapeutically effective amount of the nanoparticle results in direct tumor cell killing, dendritic cell-initiated innate immune response, and T cell-mediated adaptive immune response.

18. A method for inhibiting breast cancer tumor growth, comprising administering to a subject in need thereof an amount of a nanoparticle of claim 1 effective to inhibit tumor growth.

19. A method for inhibiting breast cancer metastasis, comprising administering to a subject in need thereof an amount of a nanoparticle of claim 1 effective to inhibit metastasis.

20. A method for making the nanoparticle of claim 1, comprising:
   (a) forming a layer of silica-polyethylene glycol surrounding an iron oxide core to provide a coated iron oxide core;
   (b) associating a tumor targeting agent to the coated core;
   (c) forming a first layer of a cytotoxic agent surrounding the coated core; and
   (d) forming a second layer of an immunomodulating agent surrounding the first layer to provide a nanoparticle comprising a tumor targeting agent, a cytotoxic agent, and an immunomodulating agent.

* * * * *

SEQUENCE LISTING

```
Sequence total quantity: 1
SEQ ID NO: 1            moltype = AA  length = 13
FEATURE                 Location/Qualifiers
source                  1..13
                        mol_type = protein
                        organism = synthetic construct
SEQUENCE: 1
CAHKHVHHVP VRL                                                       13
```